US012668597B2

(12) United States Patent
Guo et al.

(10) Patent No.: US 12,668,597 B2
(45) Date of Patent: Jun. 30, 2026

(54) HIGH-PURITY THIENOPYRIMIDINE COMPOUND AND PREPARATION METHOD THEREFOR

(71) Applicants: AURISCO PHARMACEUTICAL (TIANJIN) INC., Tianjin (CN); AURISCO PHARMACEUTICAL CO., LTD., Taizhou (CN)

(72) Inventors: Wancheng Guo, Tianjin (CN); Fuchang Zhang, Tianjin (CN); Yongli Duan, Tianjin (CN); Xiongpeng Duan, Tianjin (CN); Guoping Wang, Tianjin (CN)

(73) Assignees: AURISCO PHARMACEUTICAL (TIANJIN) INC., Tianjin (CN); AURISCO PHARMACEUTICAL CO., LTD., Taizhou (CN)

( * ) Notice: Subject to any disclaimer, the term of this patent is extended or adjusted under 35 U.S.C. 154(b) by 414 days.

(21) Appl. No.: 18/546,049

(22) PCT Filed: Sep. 6, 2021

(86) PCT No.: PCT/CN2021/107295
§ 371 (c)(1),
(2) Date: Aug. 10, 2023

(87) PCT Pub. No.: WO2022/170737
PCT Pub. Date: Aug. 18, 2022

(65) Prior Publication Data

US 2024/0317773 A1 Sep. 26, 2024

(30) Foreign Application Priority Data

Feb. 10, 2021 (CN) ......................... 202110185444.7

(51) Int. Cl.
*C07D 495/04* (2006.01)
*G01N 33/15* (2006.01)

(52) U.S. Cl.
CPC ........... *C07D 495/04* (2013.01); *G01N 33/15* (2013.01)

(58) Field of Classification Search
CPC .. C07D 495/04; C07D 519/00; C07D 409/12; C07D 333/38; G01N 33/15; G01N 30/02;
(Continued)

(56) References Cited

U.S. PATENT DOCUMENTS

2013/0012381 A1 1/2013 Le Vezouet et al.

FOREIGN PATENT DOCUMENTS

CN 110194776 A 9/2019
CN 111333633 A * 6/2020 ........... C07D 409/12

(Continued)

OTHER PUBLICATIONS

Joullié, Madeleine M. et al., "Evolution of amide bond formation", Arkivoc: Archive for Organic Chemistry, Jun. 30, 2010, vol. 2010, No. 08, pp. 189-250, ISSN: 1551-7012.

(Continued)

*Primary Examiner* — Dennis White
(74) *Attorney, Agent, or Firm* — NKL Law; Bin Lu; Allen Xue

(57) ABSTRACT

A thienopyrimidine compound (a compound of formula N) and a preparation method therefor are provided. Specifically, the preparation method includes the steps of: (a) in a solvent A, reacting, in the presence of an organic base and acyl chloride, a compound of formula N-2 with 3-amino-6-methoxypyridazine to obtain a compound of formula N-1; and (b) in a solvent B, converting, in the presence of a base, the compound of formula N-1 into the compound of formula N. The preparation method does not require toxic and (Continued)

expensive reagents, has mild reaction conditions and a high product purity, and is suitable for industrial production.

15 Claims, 14 Drawing Sheets

(58) Field of Classification Search
CPC ... G01N 30/04; G01N 30/06; G01N 2030/042
See application file for complete search history.

(56) References Cited

FOREIGN PATENT DOCUMENTS

| | | | | | |
|---|---|---|---|---|---|
| CN | 111423452 | A | | 7/2020 | |
| CN | 112745304 | A | | 5/2021 | |
| CN | 113135934 | A | | 7/2021 | |
| CN | 113429423 | A | | 9/2021 | |
| CN | 113563303 | A | | 10/2021 | |
| CN | 113563304 | A | | 10/2021 | |
| CN | 113563363 | A | | 10/2021 | |
| CN | 111423452 | B | * | 8/2023 | ........... C07D 495/04 |
| WO | 2004067535 | A1 | | 8/2004 | |
| WO | 2014051164 | A2 | | 4/2014 | |

OTHER PUBLICATIONS

Singh, Dilip Kumar et al., "Critical review on establishment and availability of impurity and degradation product reference standards, challenges faced by the users, recent developments, and trends", Trends in Analytical Chemistry, Apr. 2018, vol. 101, pp. 85-107.

* cited by examiner

HIGH-PURITY THIENOPYRIMIDINE COMPOUND AND PREPARATION METHOD THEREFOR

CROSS-REFERENCE TO RELATED APPLICATIONS

The present application is a U.S. national stage entry of PCT international application no. PCT/CN2021/107295, filed on Sep. 6, 2021, which claims the priority of Chinese patent application CN202110185444.7 filed on Feb. 10, 2021, the content of each is incorporated herein by reference in its entirety.

TECHNICAL FIELD

The present invention belongs to the technical field of pharmaceutical chemistry, and specifically relates to a high-purity Relugolix and preparation method therefor.

BACKGROUND

Relugolix, also known as RVT-601 and TAK-385, is a once-daily, oral gonadotropin-releasing hormone (GnRH) receptor antagonist that is able to inhibit the production of testosterone which can stimulate the growth of prostate cancer. In addition, Relugolix can also reduce the production of ovarian estradiol and the release of luteinizing hormone (LH) and follicle stimulating hormone (FSH) by blocking the GnRH receptor in the pituitary gland, thereby reducing the levels of estrogen produced by the female ovaries and the production of male testosterone. The structural formula thereof is as follows:

N-a

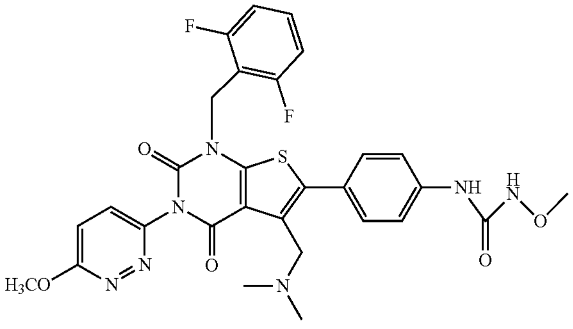

Relugolix was approved for sale by the Japan Pharmaceuticals and Medical Devices Agency (PMDA) on Jan. 8, 2019, and is marketed by Takeda and Aska Pharmaceuticals with the trade name of Relumina® (40 mg/tablet) approved for the treatment and symptom relief of myoma of uterus; and Relugolix was approved by U.S. Food and Drug Administration (FDA) for marketing on Dec. 18, 2020 with the trade name of ORGOVYX (120 mg/tablet).

Currently, multiple literatures reported methods for preparing Relugolix, wherein the preparation method disclosed in WO2004067535 is shown in Route 1:

Route 1

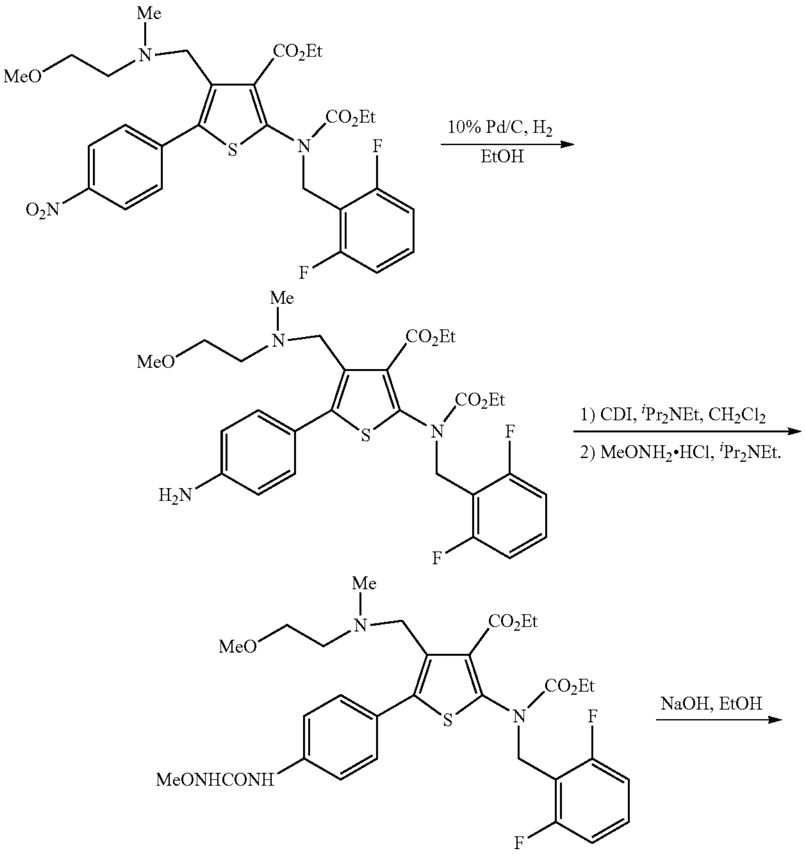

-continued
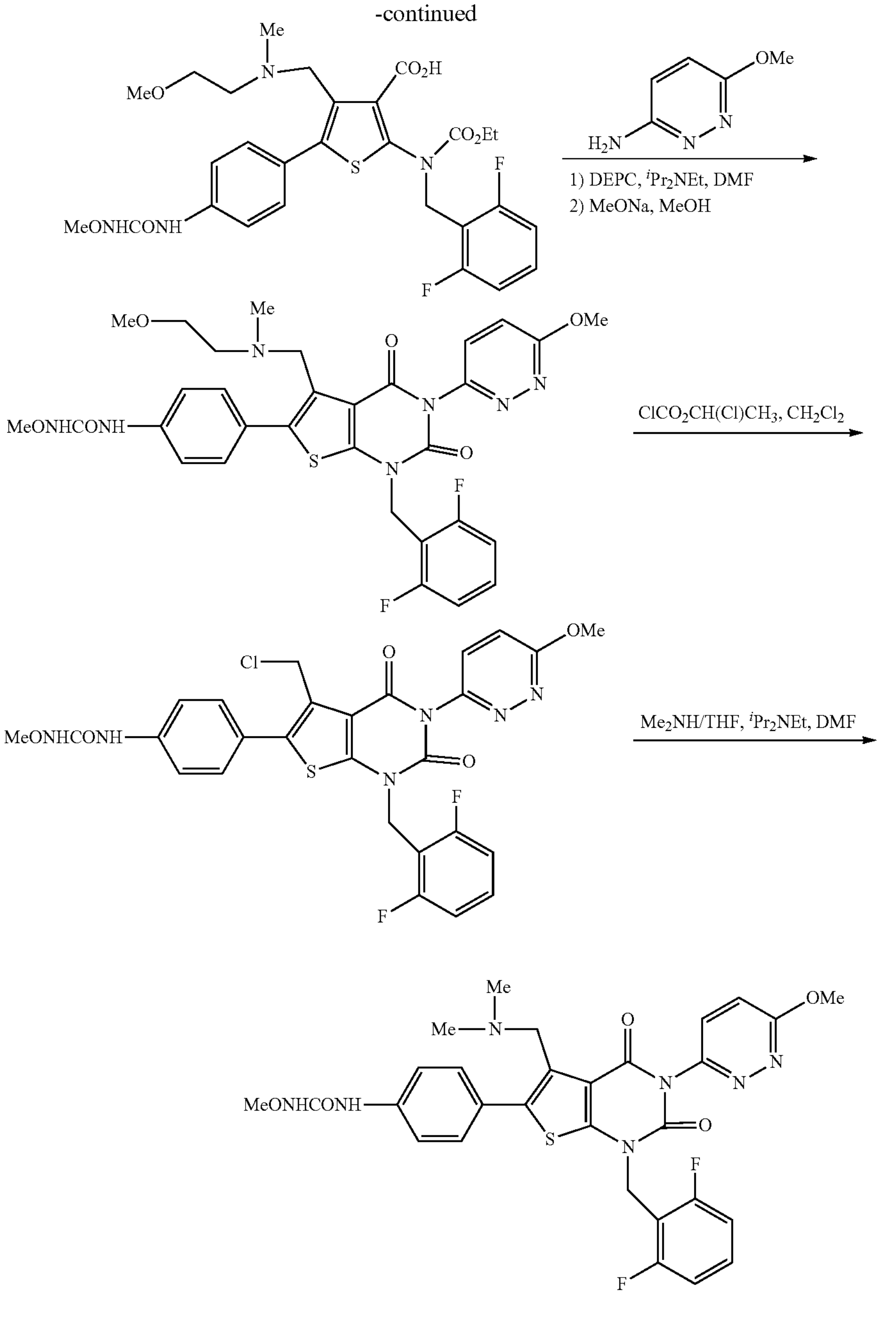
The preparation method disclosed in WO2014051164 is shown in Route 2:
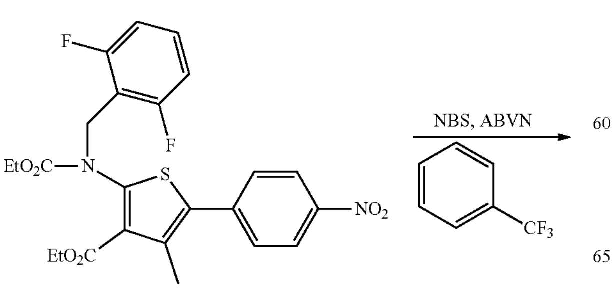
-continued
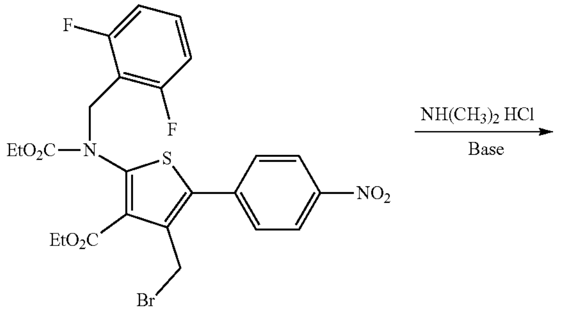

-continued
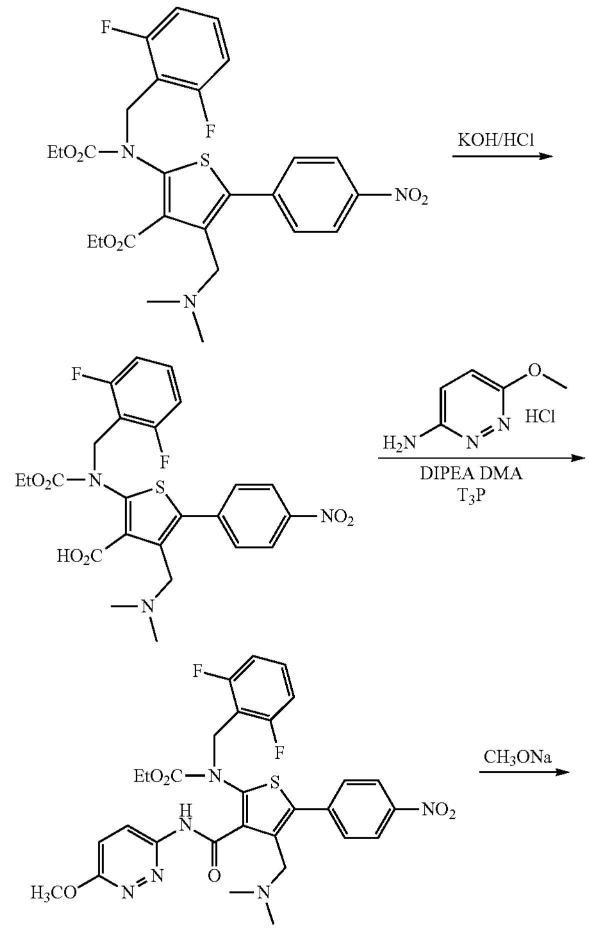
-continued
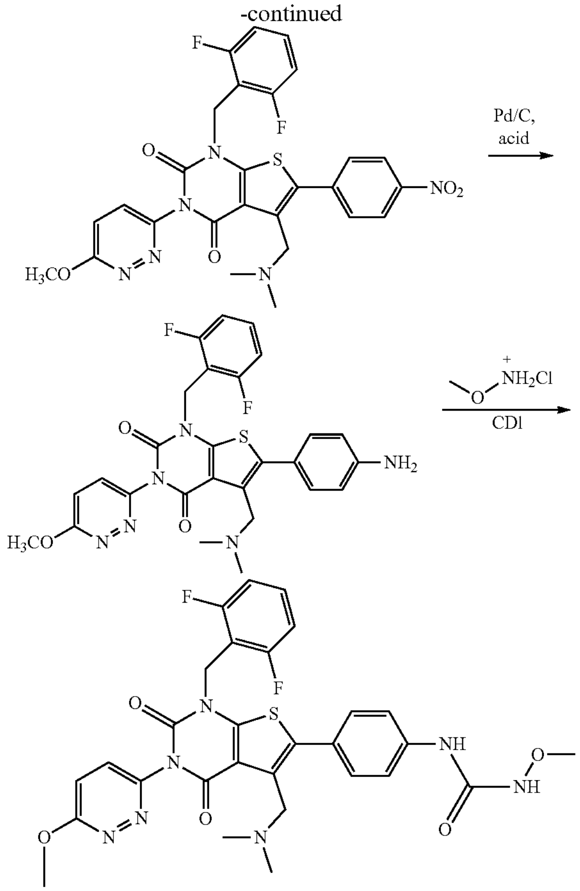
The preparation method disclosed in CN111333633A is shown in Route 3:
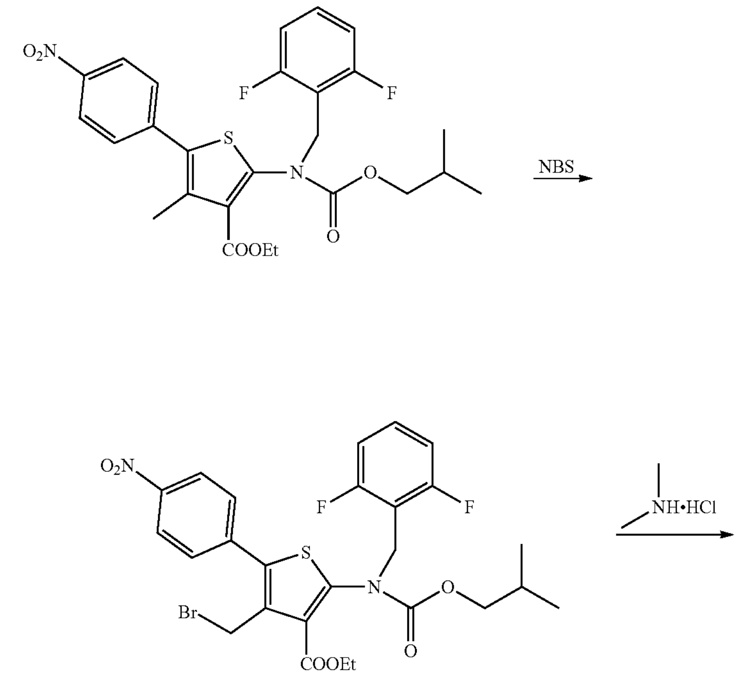

-continued
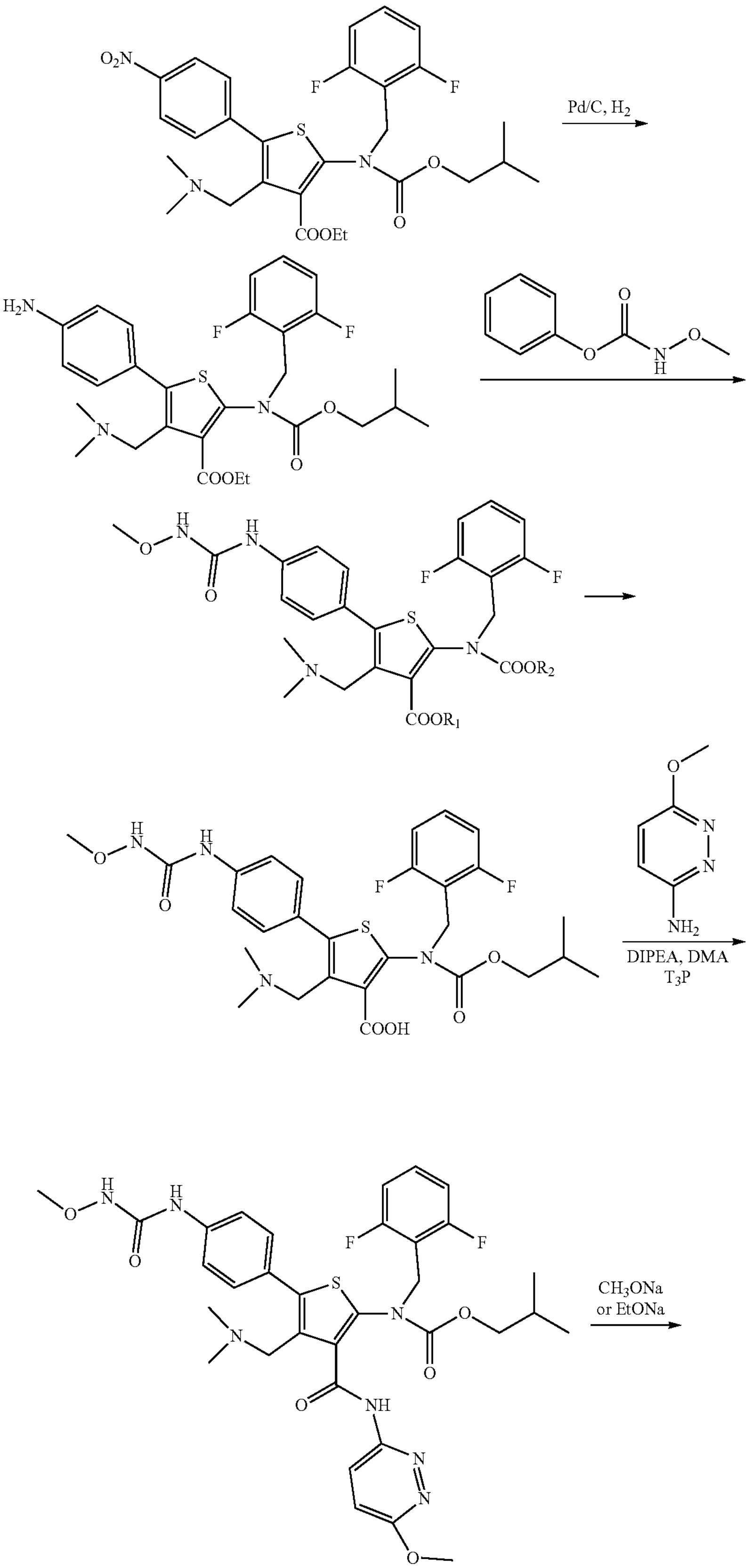

-continued

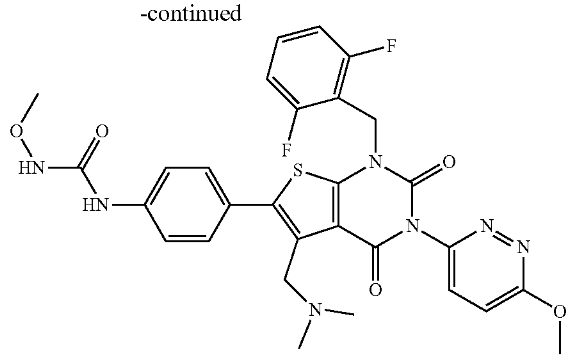

In route 1, the condensation reaction of the intermediate obtained in step 3 with 3-amino-6-methoxy pyridazine uses a condensating agent of diethyl cyanophosphate (DEPC), the corresponding condensation reaction of route 2 and route 3 with 3-amino-6-methoxy pyridazine uses the condensating agent of propyl phosphoanhydride (T3P). Both DEPC and T3P are both highly toxic and expensive.

In addition, all of the bases that used in the ring-closing reaction after the condensation reaction in the above three routes are strong alkaline sodium alcohol, which makes the ring-closing product dark in color and has many reaction by-products. According to the reaction conditions of patent CN111333633A, the proportion of raw materials converted into impurities is very high, resulting in a decline in yield, an increase in the difficulty of purifying the product, and a tendency for the content of impurities in the product to exceed the standard. Therefore, there is an urgent need in the prior art to develop a new method that is environmentally friendly, cost-effective and has better quality control for preparing thienopyrimidine compound such as Relugolix.

SUMMARY OF THE INVENTION

The purpose of the present invention is to provide a thienopyrimidine compound (such as Relugolix) and the preparation method therefor and relevant impurity reference for quality control.

In the first aspect of the present application, provided is a method for preparing a compound of formula N, comprising the following steps:

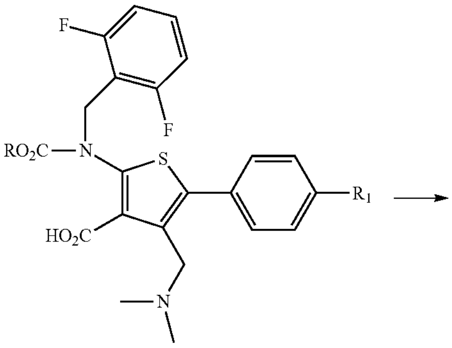

N-2

-continued

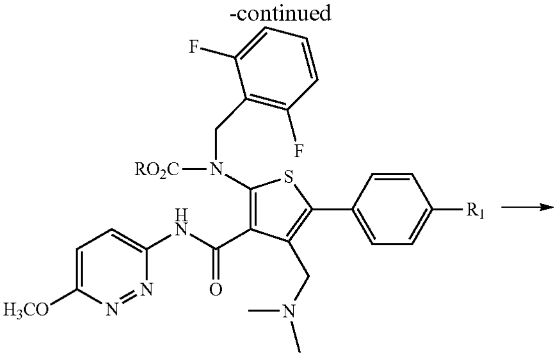

N-1

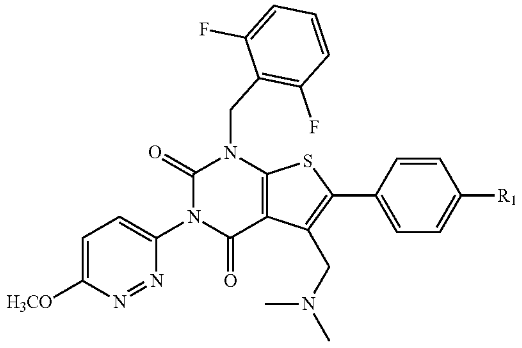

N (a) in inert solvent A, in the presence of an organic base and an acyl chloride, subjecting a compound of formula N-2 and 3-amino-6-methoxypyridazine to a condensation reaction, thereby obtaining a compound of formula N-1; and (b) in inert solvent B, in the presence of a base, subjecting the compound of formula N-1 to a ring-closing reaction, thereby obtaining a compound of formula N;

in each formula, R is $C_{1-6}$ alkyl, and $R_1$ is —$NO_2$ or —$NHCONHOCH_3$.

In another preferred embodiment, in step (a), the organic base is an organic compound containing 1-3 nitrogens and 3-20 carbons.

In another preferred embodiment, in step (a), the organic base is a compound selected from the group consisting of $R_2NH_2$, $(R_2)_2NH$, $(R_2)_3N$, 4 to 7 membered heterocyclic alkyl containing N heteroatom, 5 to 6 membered heteroaryl containing N heteroatom, or a combinations thereof; wherein $R_2$ is $C_{1-6}$ alkyl.

In another preferred embodiment, in step (a), the organic base is selected from the group consisting of triethylamine, pyridine, or a combination thereof.

In another preferred embodiment, in step (a), the acyl chloride is selected from: phosphorus oxychloride, thionyl chloride, $C_{1-8}$ alkyl sulfonyl chloride, $C_{4-20}$ aromatic sulfonyl chloride, $C_{1-8}$ alkyl acyl chloride, $C_{4-20}$ aromatic acyl chloride.

In another preferred embodiment, the $C_{4-20}$ aromatic group refers to an aryl or heteroaryl group containing 4 to 20 carbon atoms and 0 to 3 heteroatoms (preferably, the heteroatom is selected from O, N, or S).

In another preferred embodiment, the $C_{4-20}$ aromatic group is $C_{6-10}$ aryl group or 5 to 10 membered heteroaryl group; and the abovementionedaryl or heteroaryl group may also be optionally substituted by halogen, $C_{1-4}$ alkyl, or halogenated $C_{1-4}$ alkyl.

In another preferred embodiment, in step (a), the acyl chloride is selected from benzenesulfonyl chloride, methanesulfonyl chloride, thionyl chloride, or a combination thereof.

In another preferred embodiment, in step (a), the inert solvent A is selected from the group consisting of N,N-dimethylformamide (DMF), N-methylpyrrolidone, N,N-dimethylacetamide, tetrahydrofuran, dichloromethane (DCM), acetone, or a combination thereof.

In another preferred embodiment, in step (b), the base is an inorganic base.

In another preferred embodiment, in step (b), the inorganic base is selected from the group consisting of carbonate, phosphate, bicarbonate, hydrophosphate, or a combination thereof; preferably, is selected from the group consisting of potassium carbonate, sodium carbonate, caesium carbonate, tripotassium phosphate, or a combination thereof.

In another preferred embodiment, in step (b), the base is selected from the group consisting of carbonate, phosphate, bicarbonate, hydrophosphate, or a combination thereof; more preferably, is selected from the group consisting of potassium carbonate, sodium carbonate, caesium carbonate, tripotassium phosphate, or a combination thereof.

In another preferred embodiment, in step (b), the inert solvent B is selected from the group consisting of N,N-dimethylformamide, dimethylsulfoxide, N-methylpyrrolidone, N,N-dimethylacetamide, or a combination thereof.

In another preferred embodiment, the inert solvent A and the inert solvent B may be the same or different.

In another preferred embodiment, in step (a), the molar ratio of the compound of formula N-2 to 3-amino-6-methoxypyridazine is 1:1 to 3; preferably, 1:1.1 to 2.0; more preferably, 1:1.4 to 1.6.

In another preferred embodiment, in step (a), the molar ratio of the compound of formula N-2 to the organic base is 1:1.5 to 5; preferably, 1:1.1 to 2.5; more preferably, 1:1.4 to 2.1.

In another preferred embodiment, in step (a), the molar ratio of the compound of formula N-2 to the acyl chloride is 1:1 to 3; preferably, 1:1.1 to 2.0; more preferably, 1:1.4 to 1.6.

In another preferred embodiment, in step (a), the molar ratio of acyl chloride to the organic base is 1:0.5 to 2; preferably, 1:0.5 to 1.4.

In another preferred embodiment, in step (a), the weight to volume (g:mL) ratio of the compound of formula N-2 to the inert solvent A is 1:3 to 20; preferably, is 1:3 to 10.

In another preferred embodiment, in step (a), the reaction temperature of the reaction is −10 to 20° C., preferably-10 to 0° C. or 0 to 10° C.

In another preferred embodiment, step (a) further includes a post-processing step for separating and/or purifying the compound of formula N-1. In another preferred embodiment, the post-processing step for separating and/or purifying the compound of formula N-1 does not include chromatographic separation.

In another preferred embodiment, in step (b), the molar ratio of the compound of formula N-1 to the inorganic base is 1:0.5 to 3; preferably, 1:0.5 to 2.0; more preferably, 1:0.7 to 1.1.

In another preferred embodiment, in step (b), the weight to volume (g:mL) ratio of the compound of formula N-1 to the inert solvent B is 1:1 to 20; preferably, 1:2.5 to 10.

In another preferred embodiment, in step (b), the reaction temperature of the reaction is 0 to 80° C.; preferably, 20 to 60° C.; more preferably, 40 to 50° C.

In another preferred embodiment, step (b) further includes a post-processing step for separating and/or purifying the compound of formula N.

In another preferred embodiment, the post-processing step for separating and/or purifying the compound of formula N does not include chromatographic separation.

In another preferred embodiment, the post-processing step for separating and/or purifying the compound of formula N comprises: optionally cooling to 0-10° C., adding water, filtering to obtain solids, and optionally undergoing recrystallization.

In another preferred embodiment, the recrystallization comprises steps of dissolving the solids in organic solvent 1, adding organic solvent 2, optionally stirring (such as stirring for 1-3 hours), and subjecting to cooling crystallization (preferably cooling to 0-5° C.).

In another preferred embodiment, the organic solvent 1 is DMSO, and the organic solvent 2 is an alcohols solvent (preferably ethanol).

In another preferred embodiment, the volume ratio of organic solvent 1 to organic solvent 2 is 1:0.5 to 5 (preferably 1:0.5 to 3).

In another preferred embodiment, the compound of formula N is a compound of formula (N-a)

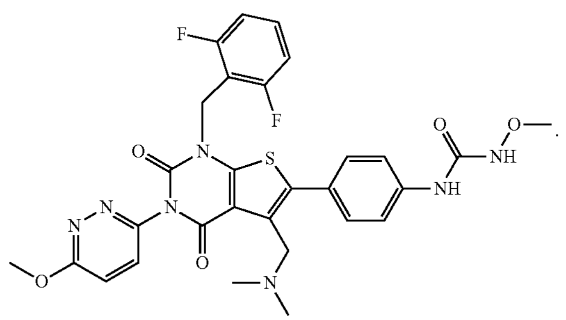

In another preferred embodiment, the compound of formula N is a compound of formula N-b, (N-b)

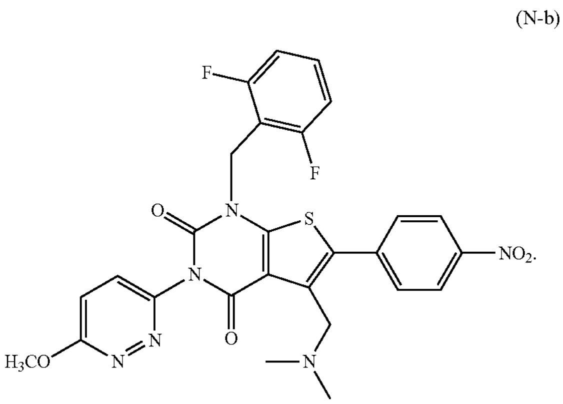 [SMILES: COc1ccc(-n2c(=O)c3c(CN(C)C)c(-c4ccc([N+](=O)[O-])cc4)sc3n(Cc3c(F)cccc3F)c2=O)nn1]

In the second aspect of the present invention, provided is a compound of formula N or a salt thereof prepared by the method according to the first aspect,

N

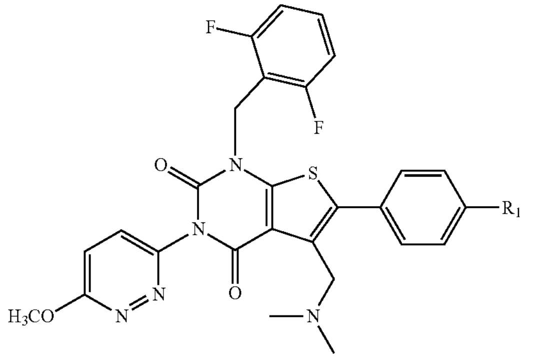

wherein the purity of the compound of formula N is ≥99.5%.

In another preferred embodiment, the content of any single impurity of the compound of formula N is ≤0.15% (preferably, ≤0.10%).

In another preferred embodiment, the single impurity refers to any one of impurity N-b1, impurity i (including impurity i-a or i-b), impurity N-b3, impurity N-b4, impurity e (including impurity e-a or e-b), RS-1, RS-2, RS-3, impurity e-a, impurity f, impurity g, impurity h, impurity i-a, impurity j, and impurity k.

In another preferred embodiment, the content of impurity i and/or impurity f in the compound of formula N is ≤0.15 (preferably, ≤0.10%).

In another preferred embodiment, the compound of formula N is the compound of formula N-a; and wherein the content of impurity k (the compound of formula k) is ≤0.15%; preferably, ≤0.10%.

In another preferred embodiment, the compound of formula N is the compound of formula N-a; and wherein the content of impurity g (the compound of formula g) is ≤0.15%; preferably, ≤0.10%.

In another preferred embodiment, the compound of formula N is the compound of formula N-a; and wherein the content of both impurities k and g is ≤0.15%; preferably, ≤0.10%.

In the third aspect of the present invention, provided is a compound of formula e, which is shown as follows (e)

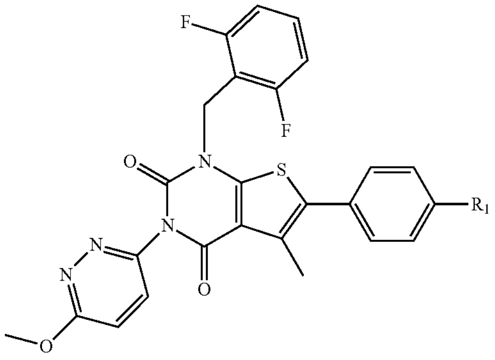

wherein $R_1$ is —$NO_2$ or —$NHCONHOCH_3$.

In another preferred embodiment, the purity of the compound is 90% or more; preferably, is 95% or more; more preferably, is 99% or more.

In another preferred embodiment, the compound is a compound that can be used as reference for quality control of the compound of formula N as defined in the first aspect.

In the fourth aspect of the present invention, provided is a compound of formula f, which is shown as follows:

(f)

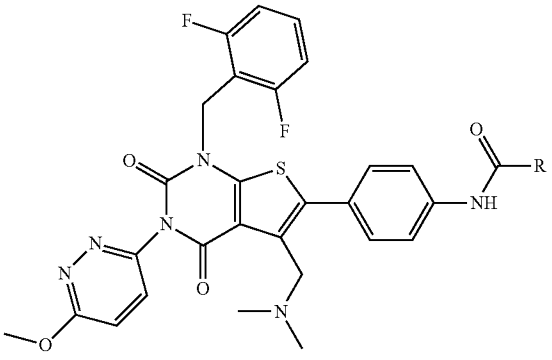

wherein R is $NH_2$ or $C_{1-6}$ alkoxy.

In another preferred embodiment, the purity of the compound is 90% or more; preferably, is 95% or more; more preferably, is 99% or more.

In another preferred embodiment, the compound is a compound that can be used as reference for quality control of the compound of formula N as defined in the first aspect.

In the fifth aspect of the present invention, provided is a compound of formula h, which is shown as follows:

(h)

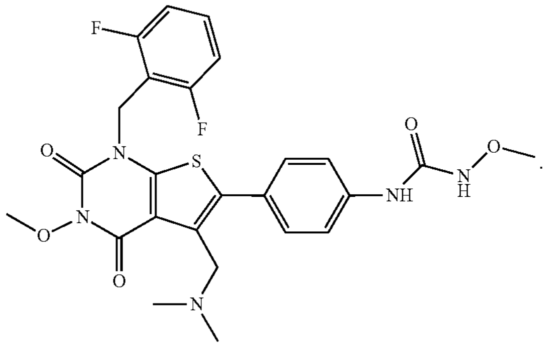

In another preferred embodiment, the purity of the compound is 90% or more; preferably, is 95% or more; more preferably, is 99% or more.

In another preferred embodiment, the compound is a compound that can be used as reference for quality control of the compound of formula N as defined in the first aspect.

In the sixth aspect of the present invention, provided is a compound of formula i, which is shown as follows:

(i)

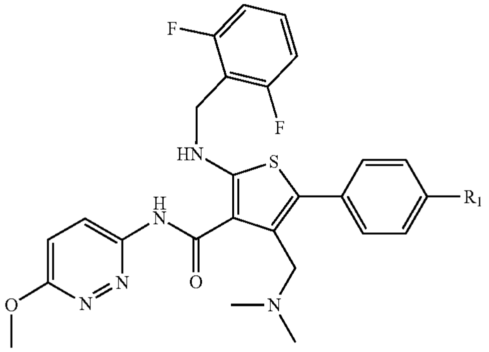

wherein $R_1$ is $—NO_2$ or $—NHCONHOCH_3$.

In another preferred embodiment, the purity of the compound is 90% or more; preferably, is 95% or more; more preferably, is 99% or more.

In another preferred embodiment, the compound is a compound that can be used as reference for quality control of the compound of formula N as defined in the first aspect.

In the seventh aspect of the present invention, provided is a compound of formula j, which is shown as follows:

(j)

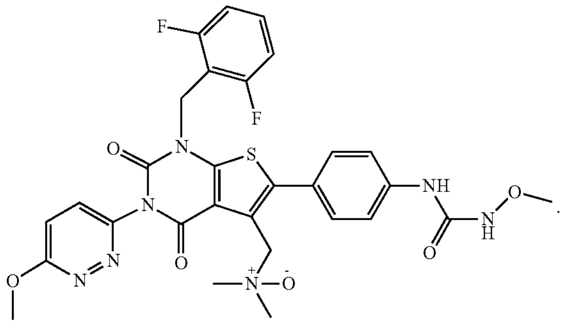

In the eighth aspect of the present invention, provided is a use of the compound according to any one of the third to the seventh, the thirteenth to the fifteenth aspects, the compound is used as an impurity reference substance in the analysis of the compound of formula N as defined in the first aspect.

In another preferred embodiment, the impurity reference substance is used as an impurity reference substance in the impurity detection for active pharmaceutical ingredients or pharmaceutical compositions or pharmaceutical preparations of the compound of formula N.

In another preferred embodiment, the compound of formula N is Relugolix (i.e., the compound of formula N-a).

In the ninth aspect of the present invention, provided is a use of the compound according to any one of the third to the seventh, the thirteenth to the fifteenth aspects as an impurity reference substance in the impurity detection for the active pharmaceutical ingredient of Relugolix (formula N-a) or the pharmaceutical preparation.

In the tenth aspect of the present invention, provided is a preparation method for the compound of formula g,

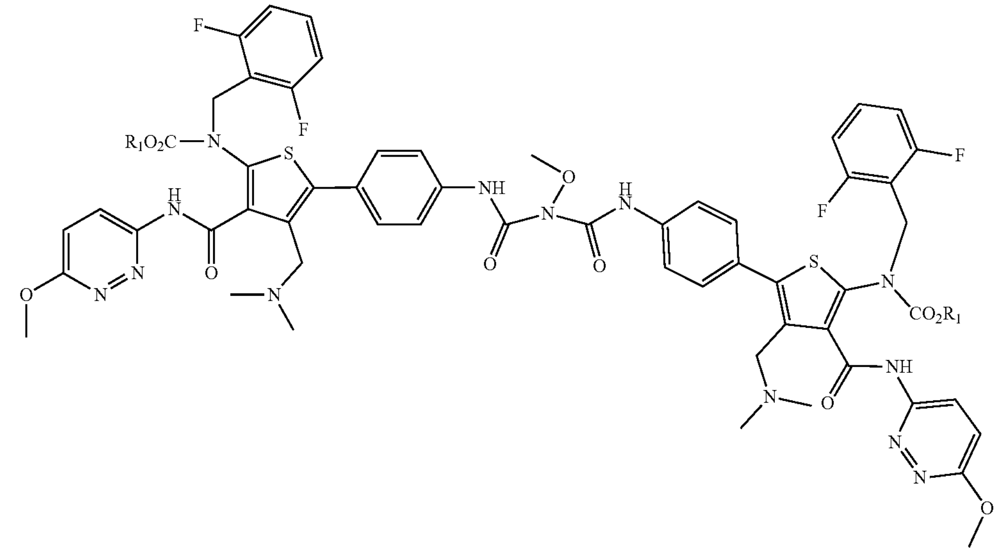
g-1
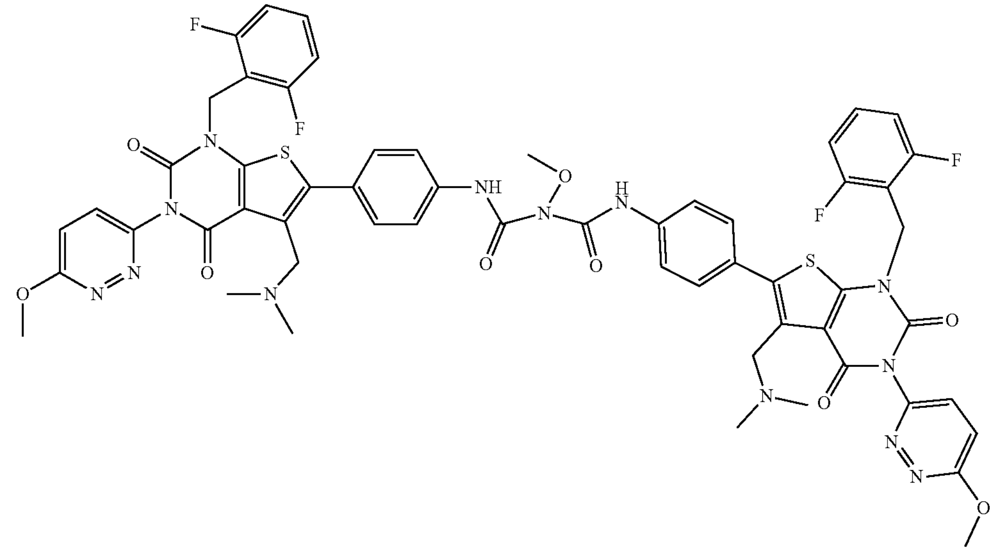
g

-continued

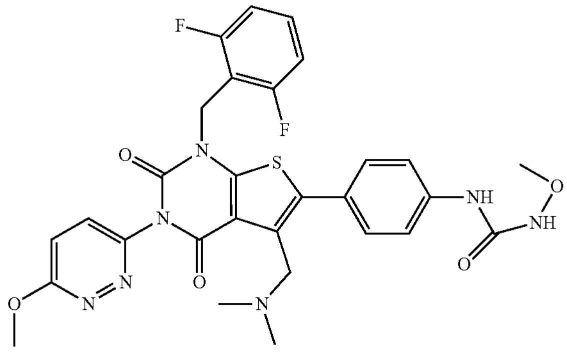

N-a

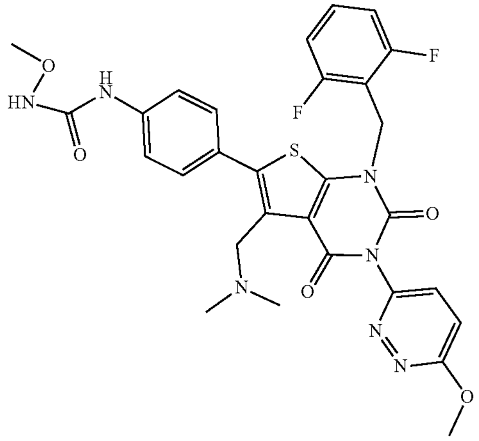

N-a in each formula, $R_1$ is $C_{1-6}$ alkyl;

the method comprises a step of closing the ring of the compound of formula g-1 under basic conditions to obtain the compound of formula g;

or, the method comprises a step of subjecting two molecules of the compound of formula N-a to an intermolecular substitution reaction under basic conditions, thereby obtaining the compound of formula g, In another preferred example, the base is an inorganic base, preferably, the inorganic base is as defined in the first aspect.

In the eleventh aspect of the present invention, provided is a preparation method for the compound of formula k,

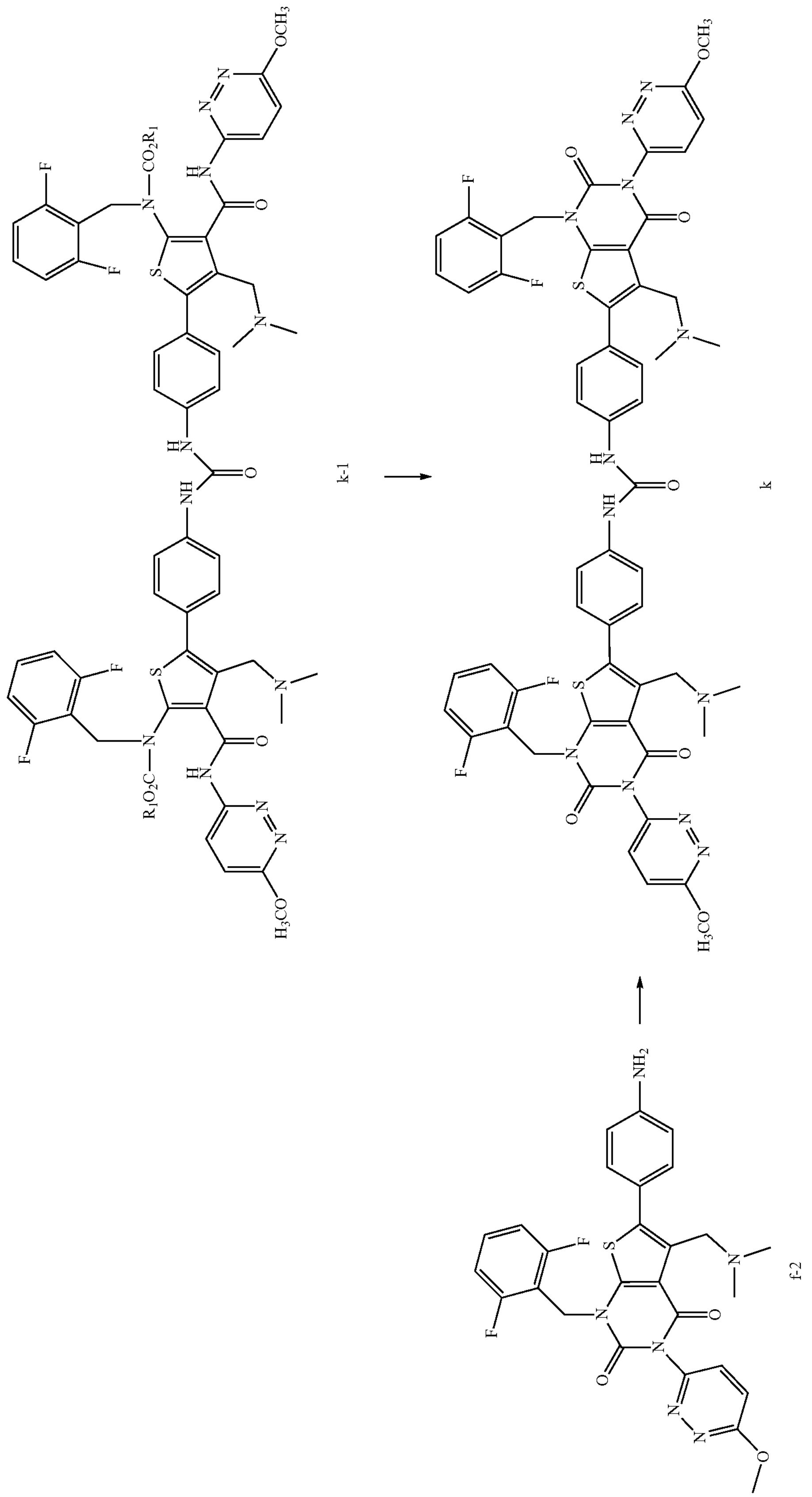
k-1
k
f-2 comprising a step of subjecting the compound of formula k-1 to a cyclization reaction under basic conditions, thereby obtaining the compound of formula k; or comprising a step of subjecting two molecules of the compound of formula f-2 to a condensation reaction under the action of CDI triphosgene, thereby obtaining the compound of formula k.

In the twelfth aspect of the present invention, provided is a compound used as a reference substance for impurity detection, wherein, the compound is as shown in any one of formula N-b1, formula i-b, formula N-b3, formula N-b4, formula e-b, formula e-a, formula f, formula g, formula h, formula i-a, formula j, formula k, formula 1;

N-b1

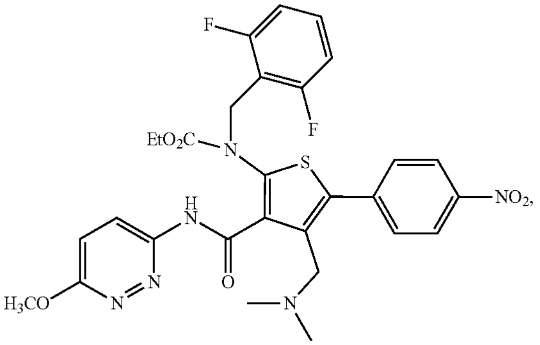

j-b

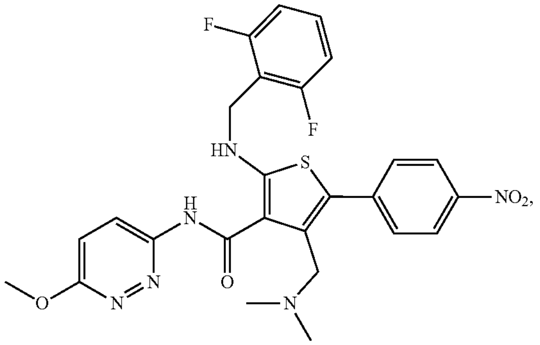

N-b3

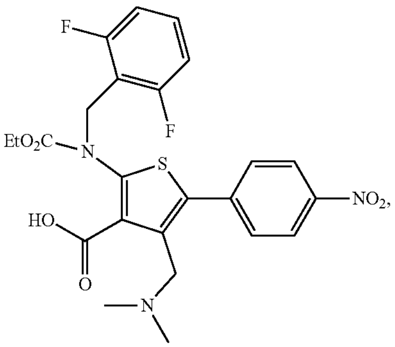

N-b4

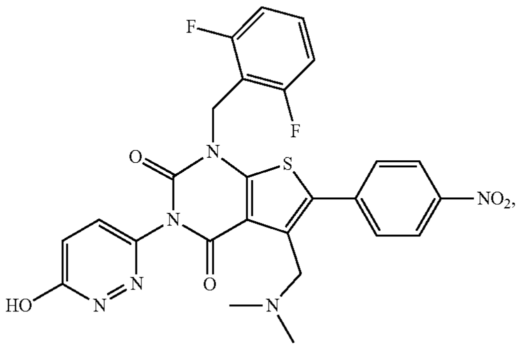

e-b

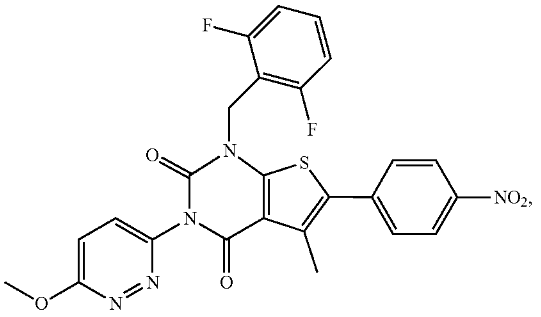

e-a

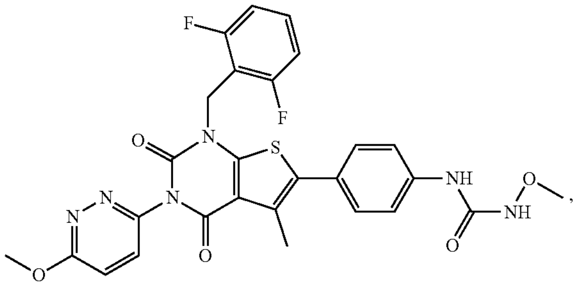

f

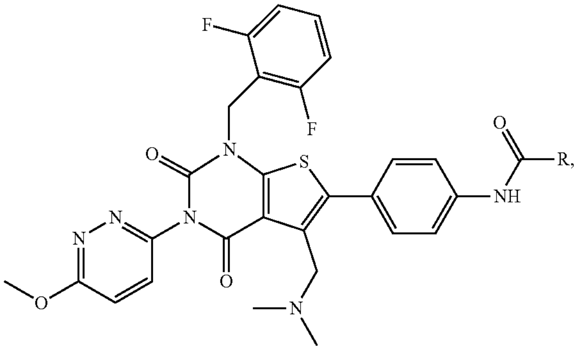

-continued
g
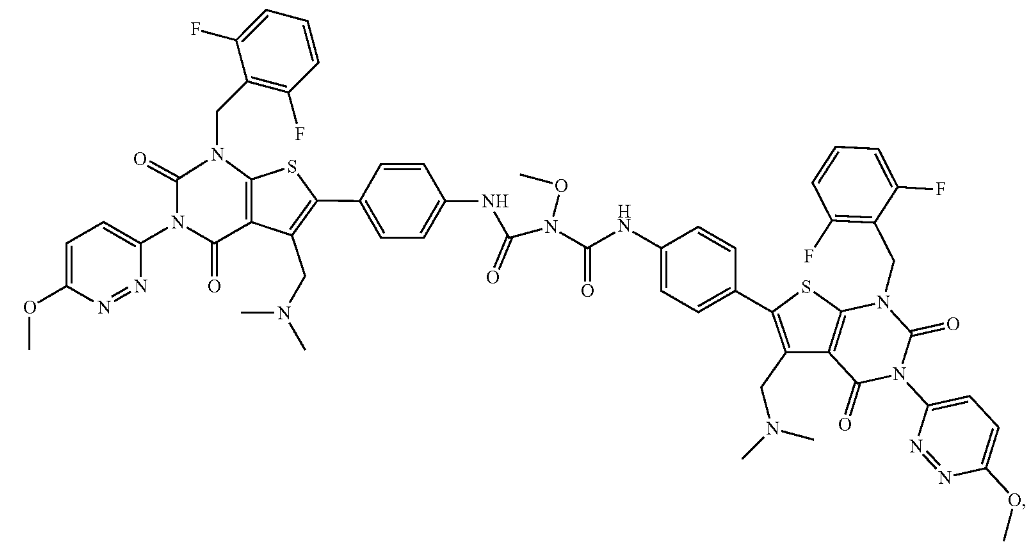
h
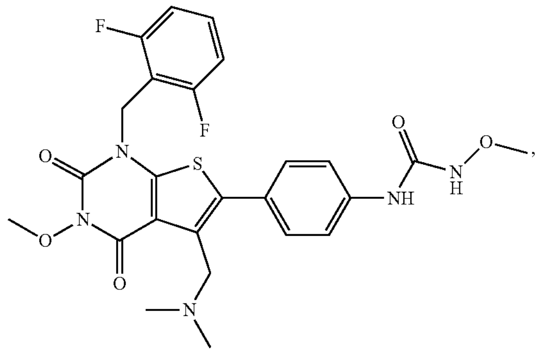
i
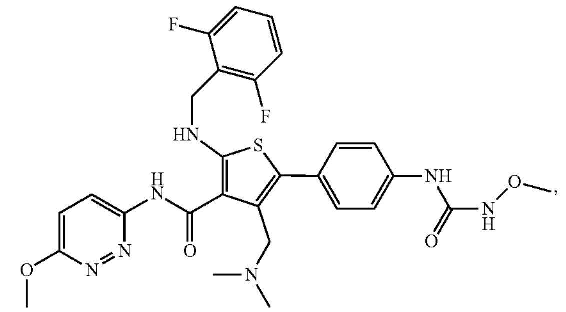
j
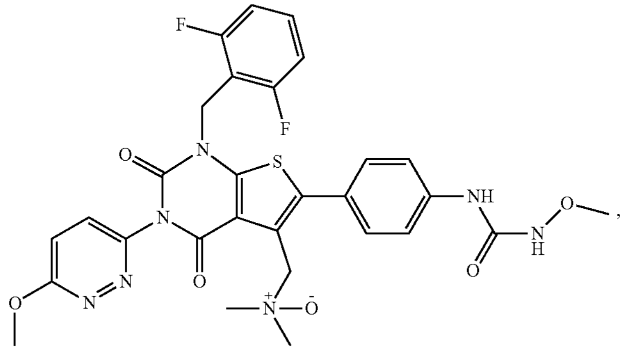
k
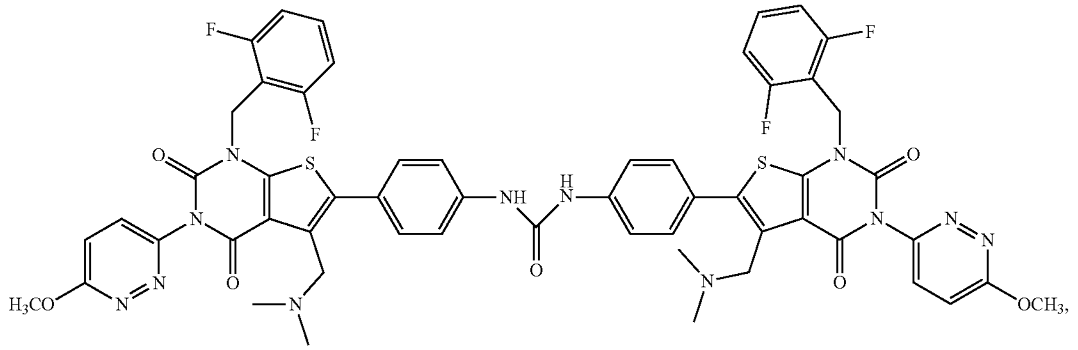

-continued l

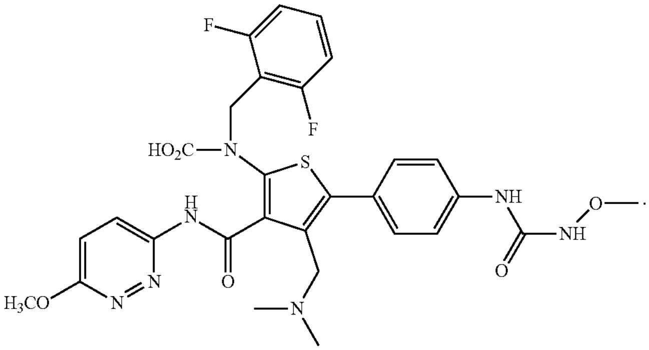

In the thirteenth aspect of the present invention, provided is a compound of formula g (g)

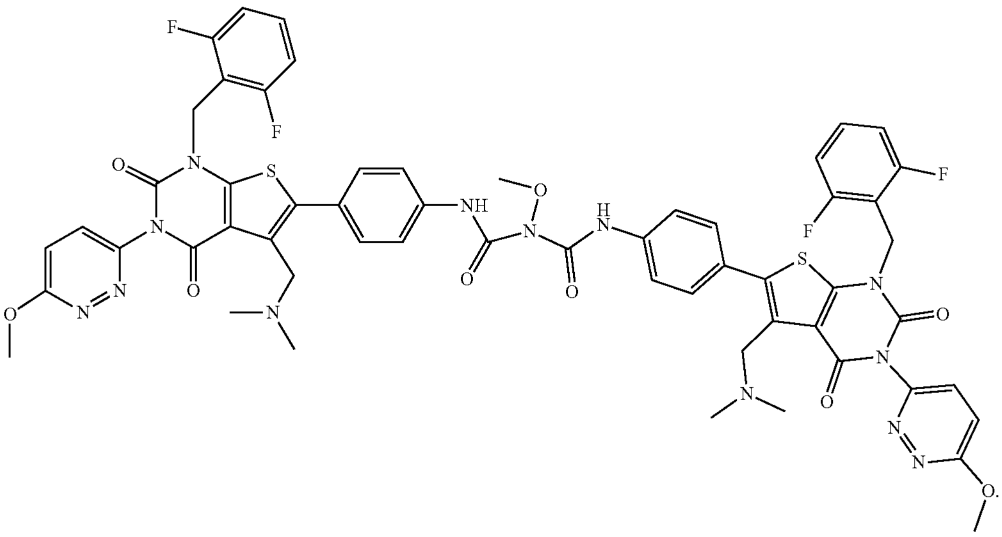

In another preferred embodiment, the compound is a compound that can be used as reference for quality control of the compound of formula N as defined in the first aspect.

In the fourteenth aspect of the present invention, provided is a compound of formula k In another preferred embodiment, the compound is a compound that can be used as reference for quality control of the compound of formula N as defined in the first aspect.

In the fifteenth aspect of the present invention, provided is a compound of formula 1

(k)

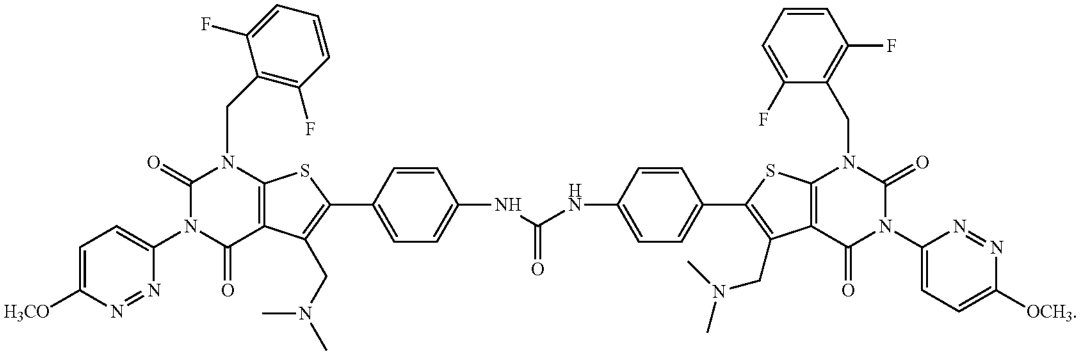

(I)

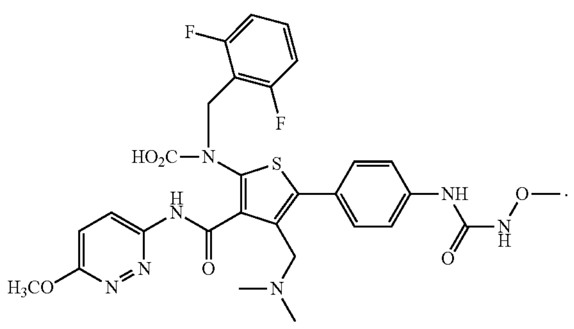

In another preferred embodiment, the compound is a compound that can be used as reference for quality control of the compound of formula N as defined in the first aspect.

It should be understood that within the scope of the present invention, the above technical features of the present invention and the technical features specifically described in the following (eg, embodiments) can be combined with each other, thereby forming a new or preferred technical solution. Due to space limitations, it will not be repeated herein.

EMBODIMENTS FOR CARRYING OUT THE INVENTION

Figure 1:
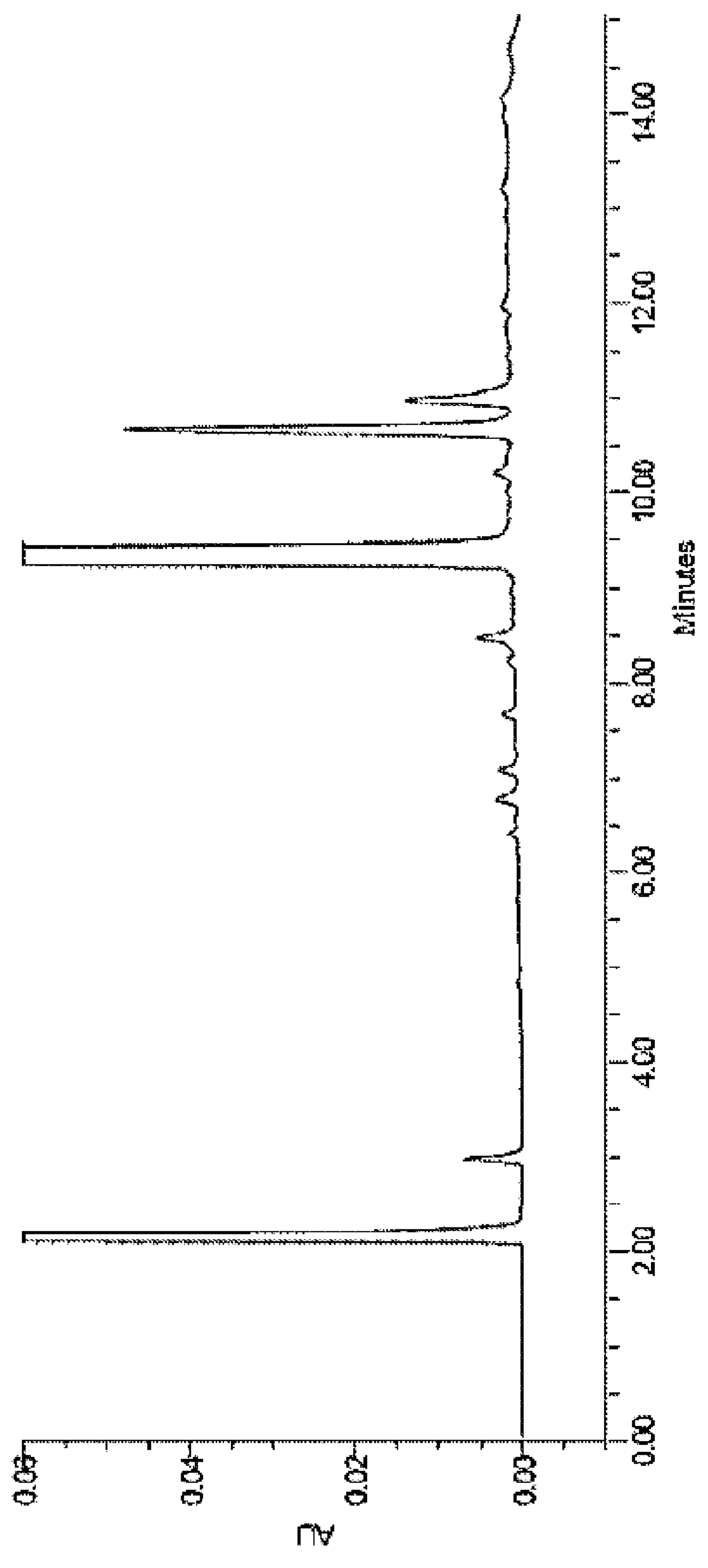
FIG. 1 shows the HPLC detection and analysis graph after reacting for 10 hours in step a of example 9.

After extensive and in-depth research, the inventors unexpectedly found that the condensation reaction in the presence of acyl chloride can achieve similar or even better technical effect such as yield and purity, compared to condensation reactions in the prior art using the condensation agent diethyl cyanophosphate (DEPC) or propylphosphonic anhydride solution (T3P) which is expensive and highly toxic, thereby providing a novel, and environmentally friendly preparation method for thienopyrimidine compound (as shown in formula N) with lower cost. Based on this, the inventors completed the present invention.

In addition, after long-term and in-depth research, the inventors also determined for the first time multiple impurities and structures thereof that affect the purity of the desired product thienopyrimidine compound (as shown in formula N), and the inventors further analyzed the causes of impurities, thereby also providing a preferred method for preparing thienopyrimidine compound with higher purity and less single impurity content. The method of the present invention, by analyzing the causes of impurities on the basis of impurity studies, avoids reaction reagents and conditions and the like that are prone to producing impurities, and effectively controls the content of various impurities in the product, thereby obtaining thienopyrimidine compound with high purity without the use of chromatographic separation. Based on this, the inventors completed the present invention.

Terms

As used herein, the term "alkyl" refers to a saturated straight or branched chain hydrocarbon group, containing a specified number of carbon atoms, e.g., $C_{1-6}$ alkyl refers to a saturated straight or branched chain hydrocarbon group containing 1 to 6 carbon atoms. Examples of alkyl include, but are not limited to, methyl, ethyl, propyl (including n-propyl or isopropyl), butyl (including n-butyl, isobutyl, tert-butyl) and the like.

As used herein, the term "alkoxy" refers to an alkyl group (wherein the alkyl is as defined above) attached to the rest of the molecule through an oxygen atom, for example, $C_{1-6}$ alkoxy is $C_{1-6}$ alkyl-O—. Examples of alkoxy include, but are not limited to, methoxy, ethoxy, and the like.

Unless otherwise defined, as used herein, aromatic group refers to an aromatic group containing a specified number of carbon atoms, for example, $C_{4-20}$ refers to an aromatic group containing 4-20 carbon atoms. Specific examples of aromatic group include substituted or unsubstituted aryl and heteroaryl. The term "aryl" means a polyunsaturated (typically aromatic) hydrocarbon group which can be a single ring or multiple rings which are fused together or linked covalently. The term "heteroaryl" refers to an aryl group (or ring) containing 1 to 5 heteroatoms selected from N, O and S. A heteroaryl group can be attached to the rest of the molecule through heteroatom. Non-limiting examples of aryl include phenyl, and naphthyl, and non-limiting examples of heteroaryl include pyridinyl and the like. The above aryl and heteroaryl can further be substituted by one or more (such as 1, 2 or 3) halogen, $C_{1-4}$ alkyl or halogenated $C_{1-4}$ alkyl.

As used herein, "compound of formula g" and "impurity g" can be used interchangeably and refer to the compound represented by formula g herein. Similarly, "compound of formula i" and "impurity i", or "compound of formula h" and "impurity h" and the like can be used interchangeably, and refer to the compound shown in the corresponding structural formula.

High-Purity Thienopyrimidine Compound and Preparation Method Therefor

Aim at the above-mentioned problems existing in the prior art, the purpose of the present invention is to provide a new method for preparing the compound of formula N such as Relugolix, without requirement for toxic and expensive reagents. The method is carried out under mild reaction conditions with high product purity and is suitable for industrial production.

One of the purposes of the present application is to provide a method for preparing a compound of formula N, comprising the following steps:

a) in solvent A, in the presence of an organic base and a condensating agent acyl chloride, reacting a compound of formula N-2 with 3-amino-6-methoxypyridazine to obtain a compound of formula N-1;
b) in solvent B, in the presence of a base (such as an inorganic base), subjecting the compound of formula N-1 to a ring-closing reaction to obtain a compound of formula N.

The reaction formula is as follows:

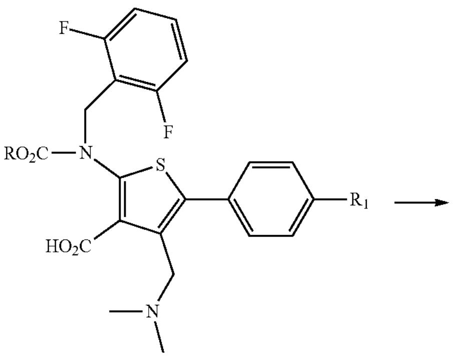

N-2

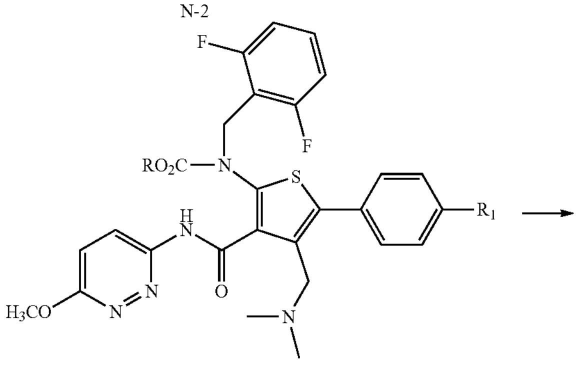

N-1

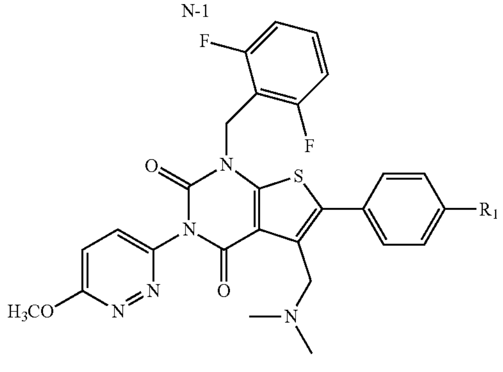

N wherein, R is $C_{1-6}$ alkyl (such as methyl, ethyl, propyl, and the like), and $R_1$ is $NO_2$, $NH_2$ or $NHCONHOCH_3$.

Preferably, the organic base is selected from an organic compound containing 1-3 nitrogens and 3-20 carbons, preferably triethylamine, pyridine.

Preferably, the acyl chloride is selected from phosphorus oxychloride, thionyl chloride, $C_{1-8}$ straight or branched alkyl sulfonyl chloride, $C_{4-20}$ aromatic sulfonyl chloride, $C_{1-8}$ straight or branched alkyl acyl chloride, $C_{4-20}$ aromatic acyl chloride, preferably benzenesulfonyl chloride, methanesulfonyl chloride, thionyl chloride.

Preferably, the inert solvent A is selected from one or more combinations of N,N-dimethylformamide, N-methylpyrrolidone, N,N-dimethylacetamide, tetrahydrofuran, dichloromethane (DCM), acetone.

Preferably, the inorganic base is selected from one or more combinations of carbonate, phosphate, bicarbonate, hydrophosphate; preferably, potassium carbonate, sodium carbonate, caesium carbonate, tripotassium phosphate.

Preferably, the solvent B is selected from one or more combinations of N,N-dimethylformamide, dimethylsulfoxide, N-methylpyrrolidone, N,N-dimethylacetamide.

Preferably, the inert solvent A and the inert solvent B may be the same or different.

When $R_1$ is $NHCONHOCH_3$, it is the compound of formula N-a, i.e., Relugolix.

In step a, the molar ratio of the compound of formula N-2 to 3-amino-6-methoxypyridazine is 1:1 to 3; preferably, 1:1.1 to −1.5; and/or the molar ratio of the compound of formula N-2 to the organic base is 1:1.5 to 5; preferably, 1:2 to 3; the molar ratio of the compound of formula N-2 to the acyl chlorides is 1:1.5 to 5; preferably, 1:2 to 3; and/or the weight to volume ratio of the compound of formula N-2 to the solvent A is 1:3 to 20; preferably, 1:3 to 10; and/or the reaction temperature is −10 to 20° C., preferably 0 to 10° C.

In step b, the molar ratio of the compound of formula N-1 to the inorganic base is 1:3 to 20, preferably 1:3 to 5; and/or the weight to volume ratio of the compound of formula N-1 to the solvent B is 1:3 to 20, preferably 1:3 to 10.

Another purpose of the present invention is to provide a compound of formula N-a or a salt thereof, (N-a)

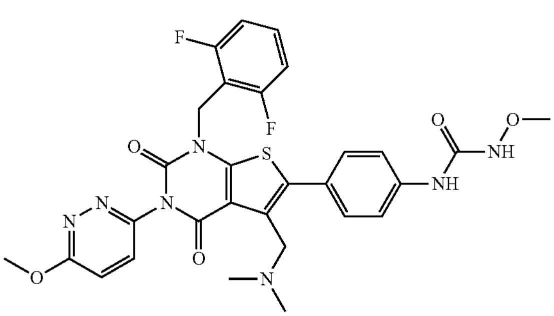

the compound of formula N-a contains no more than 0.15% of the compound of formula g.

(g)
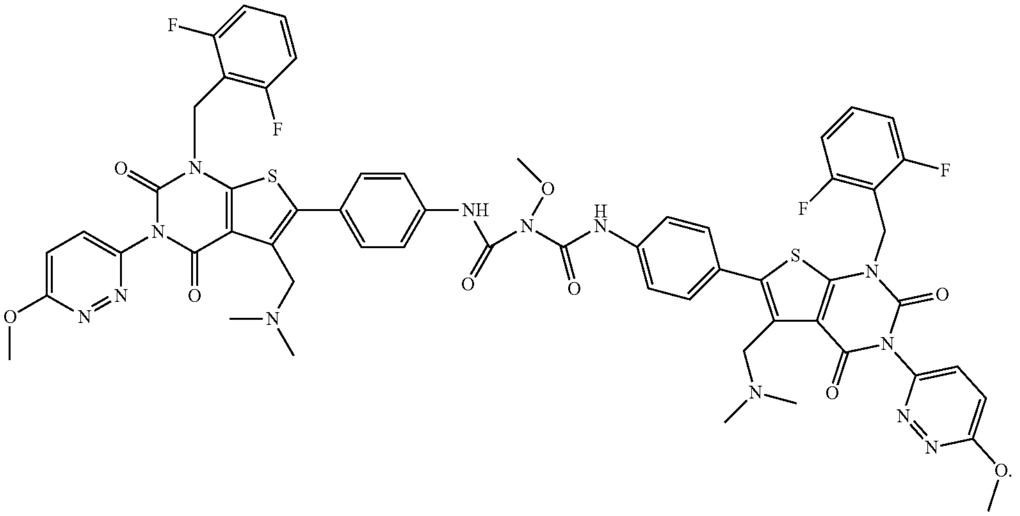
Another purpose of the present invention is to provide a compound of formula N-a or a salt thereof,
(N-a)
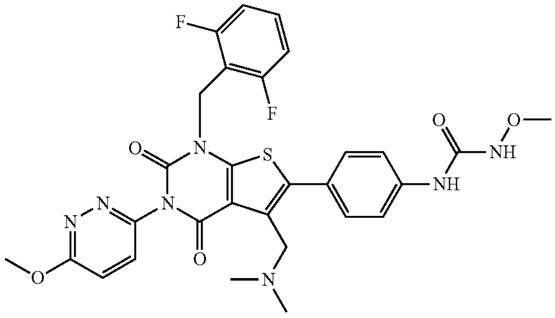
the compound contains no more than 0.15% of the compound of formula k.
(k)
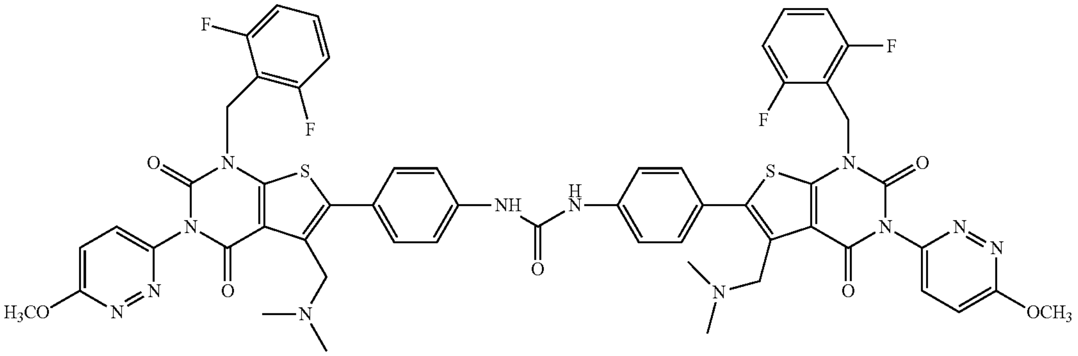

Another purpose of the present invention is to provide a compound of formula N-a or a salt thereof, (N-a)

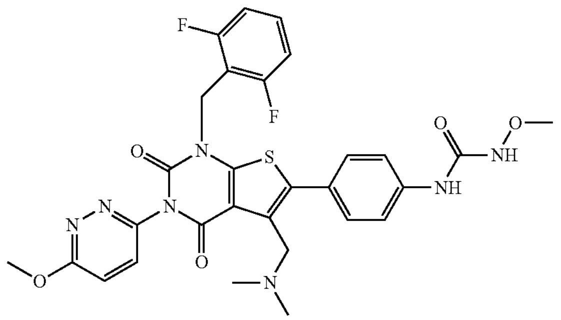

the compound contains no more than 0.15% of the compound of formula g and the compound of formula k.

Impurities of Thienopyrimidine Compound and the Preparation Method Therefor and the Use Thereof as Assay Reference Substance The study of impurities is an extremely important part of drug research. At present, only WO2014051164 reported three impurities RS-1, RS-2, and RS-3 (as shown in the following formula) of Relugolix, and in fact, only analyzing and detecting the three impurities is far from achieving the quality control of the product of APIs and the preparations thereof. There is a need for a systematic study on impurities of intermediates and APIs from the process, including impurities resulting from reactions, oxidation impurities and degradation impurities of products.

(g)

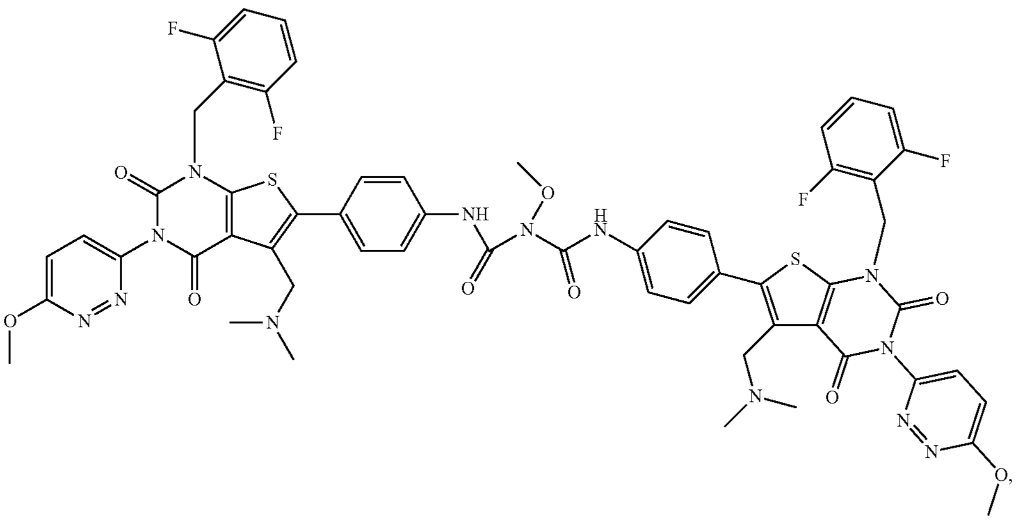

(k)

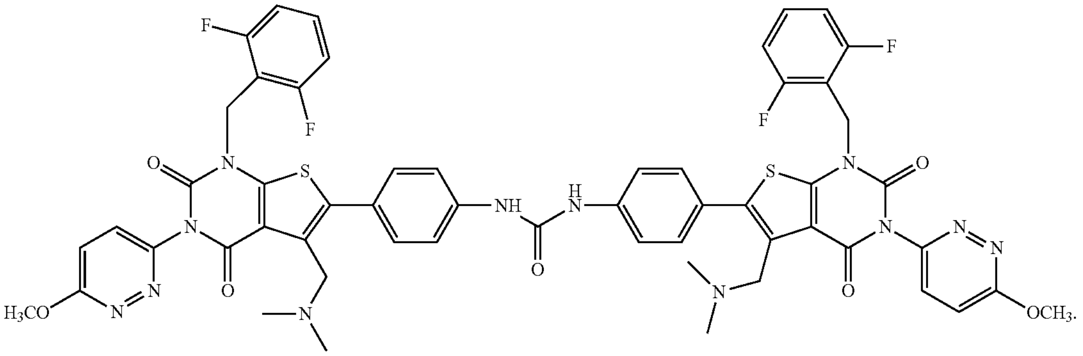

RS-1

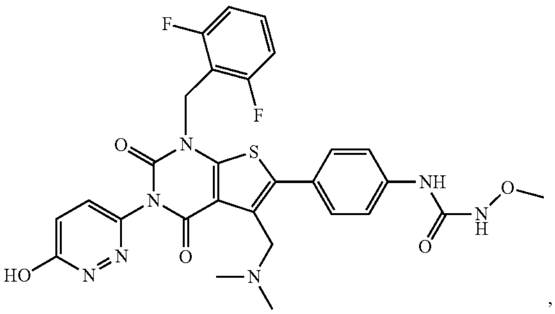

,

RS-2

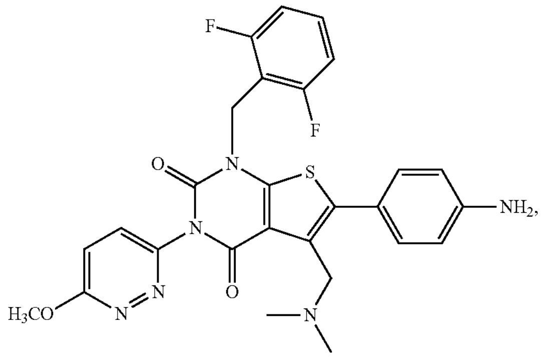

RS-3

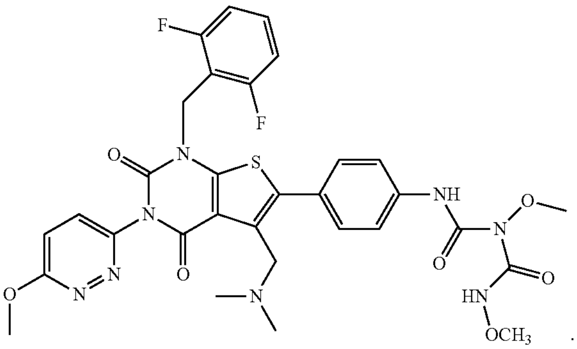

.

When repeating the method in CN111333633A, the inventors found that the chemical purities of the condensation reaction product and the ring-closing product were not as high as reported. The condensation reaction was carried out using the feedstock with the same purity (97.77%), the condensation product system had a purity of less than 90%, and the post-treatment required column chromatography. It is not suitable for industrial scale-up.

In addition, the inventors also found that the use of strong alkaline sodium alcohol in the ring-closing reaction can easily lead to the content of impurity i exceeding the standard, and due to high content of impurities i and 1 converted, the yield decreased.

Figure 14:
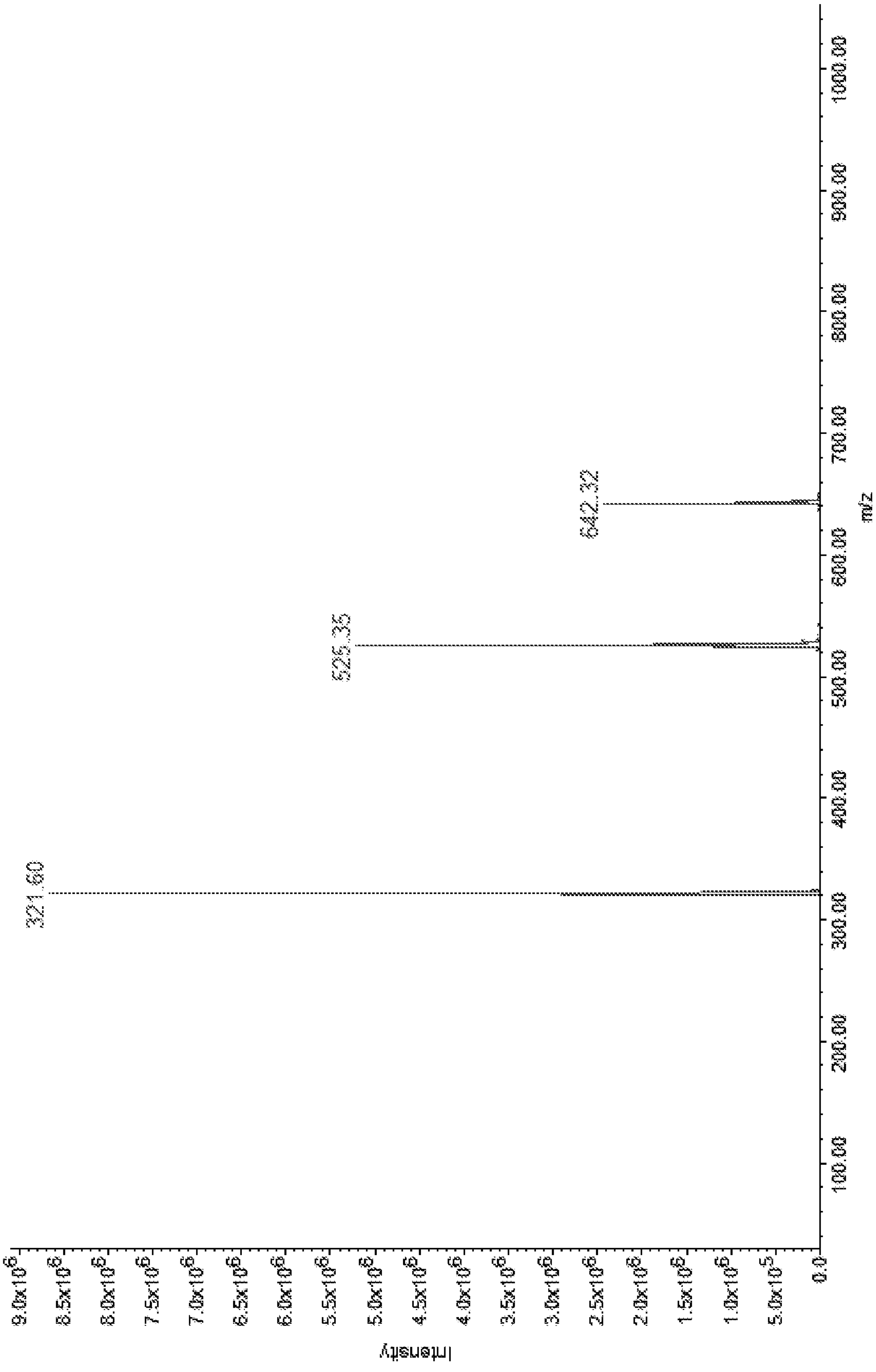
FIG. 14 shows the mass spectral result of impurity 1, the $[M+H]^+$ of impurity 1 is 642.32.

In addition, when the condensation and ring-closing reaction were carried out in the presence of side chain methoxy urea group, more side reactions occurred. The ring-closing reaction using the feedstock with the same purity (97.77%) resulted in only a small amount of product, and most of which were converted to the two degradation impurities i and 1. Only about 82% of the feedstock converted to the target product even under optimized conditions (impurity 1 is a presumed structure based on the mass spectral information, and the mass spectral result is shown in FIG. 14 with $[M+H]^+$ of 642.32).

In order to overcome the general inadequacy of the prior art in the study of the thienopyrimidine compound (e.g., Relugolix) processes and impurities in the processes, the present invention also provides a plurality of impurity structures of the thienopyrimidine compound (e.g., Relugolix) and methods of preparation therefor, which can provide better quality control for APIs and preparations of thienopyrimidine compounds, and provide more comprehensive and intuitive quality control standards for the production of APIs and preparations thereof.

In one specific embodiment, the present invention provides a new impurity e of API of the thienopyrimidine compound (such as Relugolix).

e

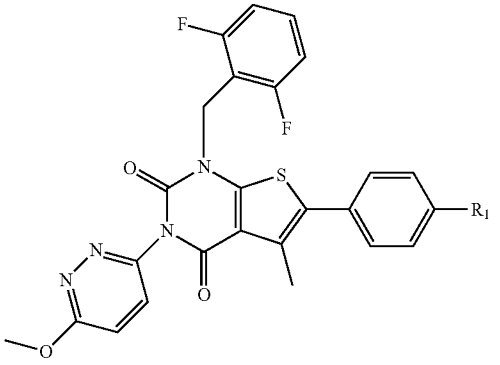

The source of impurity e contains the following two routes and most of them come from the intermediate residues of the previous steps, such as the incomplete bromination reaction of the first step in WO2014051164 or CN111333633A, or the derivatives of the demethylamine removal by-products of the subsequent catalytic hydrogenation reduction of nitro step.

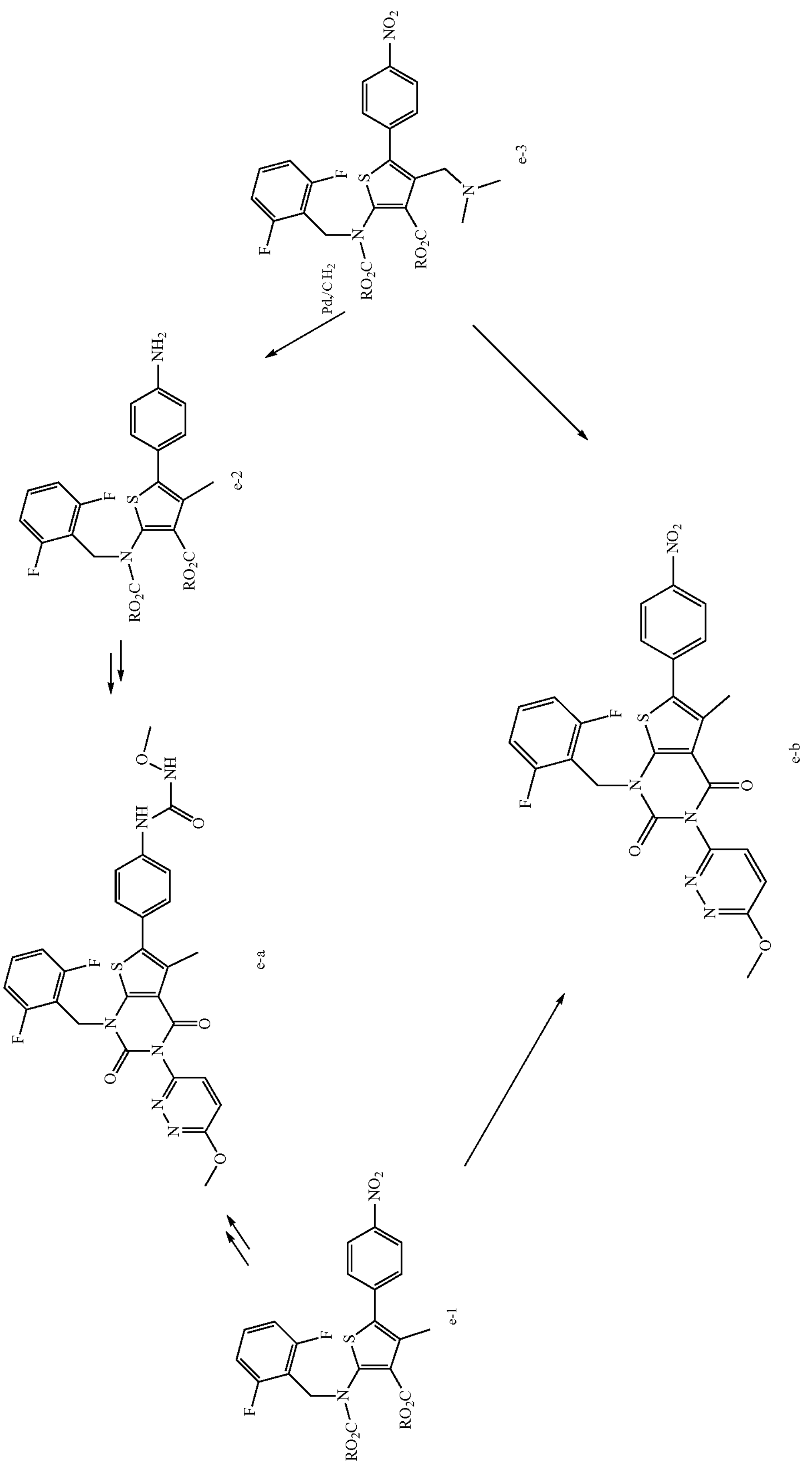
e-3
Pd/CH2
e-2
e-a
e-b
e-1 wherein R is $C_{1-6}$ straight or branched alkyl, and $R_1$ is $NO_2$ or $NHCONHOCH_3$.

In one specific embodiment, the present invention provides a new impurity f of API of the thienopyrimidine compound (such as Relugolix).

f

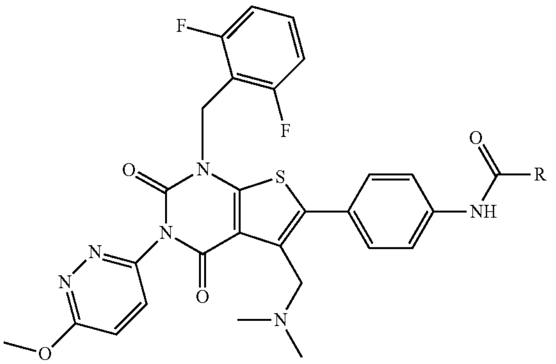

wherein R is $NH_2$ or $C_{1-6}$ straight or branched alkoxy.

The impurity f originates from the ammonolysis or alcoholysis of urea side chain groups, the source of ammonia or alcohol can be the ammonium salts left over from the post-reaction treatment, such as ammonium chloride, ammonium acetate, or reaction solvents, residual solvents, etc., which are generated under alkaline cyclization conditions, or ammonia from the decomposition of the unstable product during the reaction process. This impurity is difficult to purify, and strict control is required over the raw material sourced-ammonium salt and the remaining ammonium salt post-reaction treatment. Under optimized conditions for the ring-closing reaction, the generation of this impurity during the reaction can be confined toless than 0.1%, or even less than 0.05% in the reaction system.

In another specific embodiment, the present invention provides a preparation method for impurity f.

Typically, when R is $C_{1-6}$ straight or branched alkoxy in impurity f, the impurity f can be obtained by the following two reaction routes.

Route 1: closing the ring of the compound of formula f-1 under basic conditions to give the compound of formula f.

Route 2: making the compound of formula N-a to attack the side chain urea carbonyl carbon in the presence of sodium alkoxide, and undergoing a substitution reaction to give the compound of formula f.

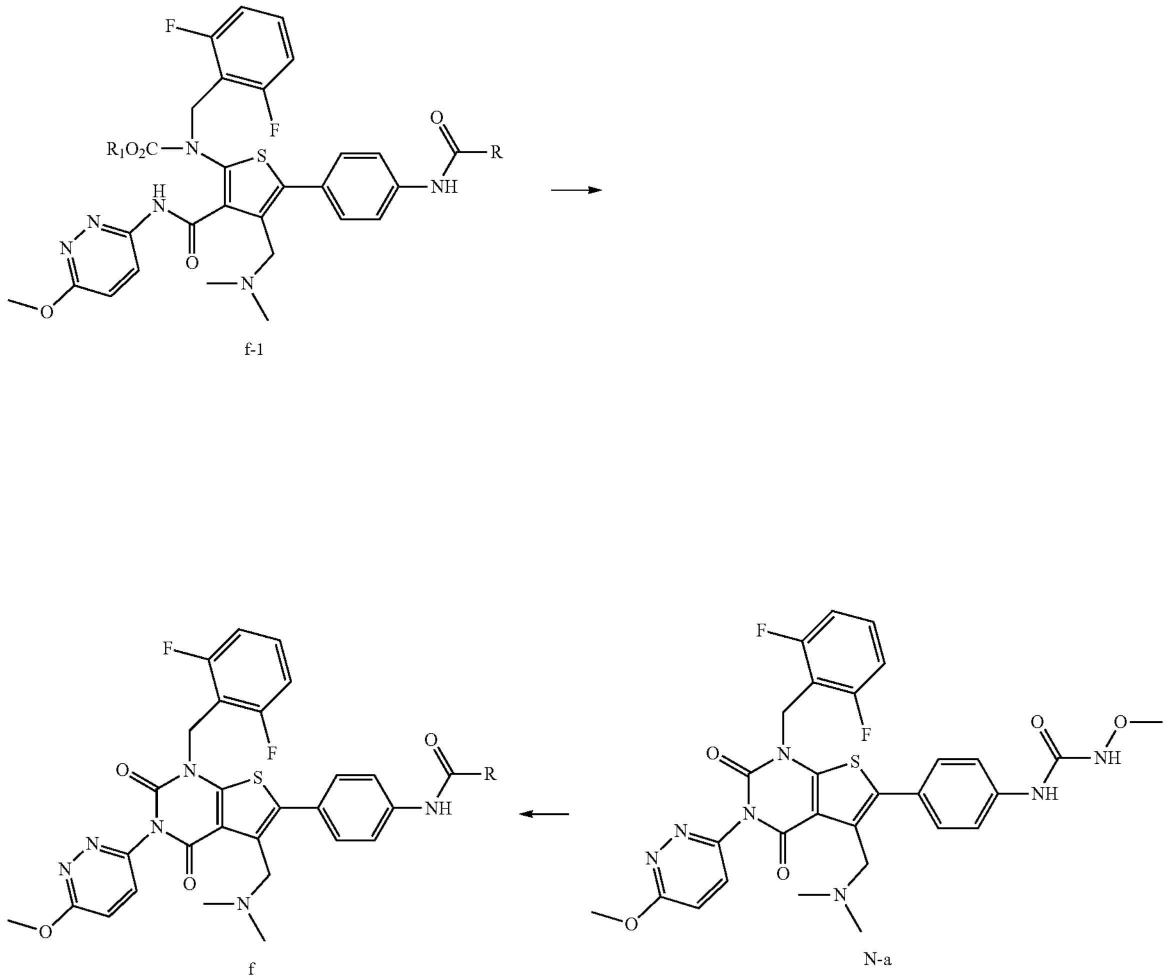

f-1 f

N-a wherein $R_1$ is $C_{1-6}$ straight or branched alkyl.

Typically, when R in impurity f is $NH_2$, impurity f can be obtained by the following two routes.

Route 1: subjecting the compound of formula f-2 to a condensation reaction with CDI and amine water/ammonia to give the compound of formula f.

Route 2: making the compound of formula N-a to attack the side chain urea carbonyl carbon in the presence of amine water/ammonia, and undergoing a substitution reaction to give the compound of formula f.

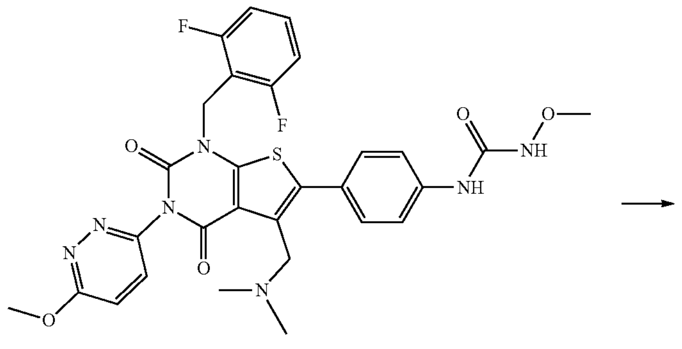

N-a

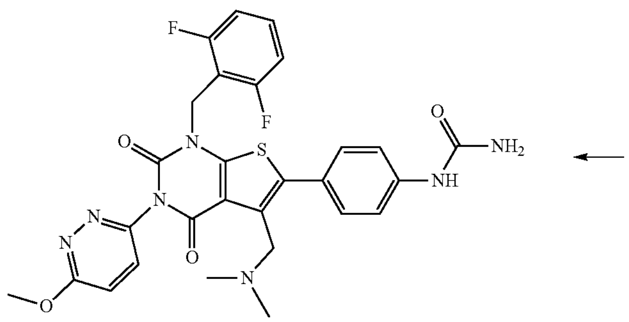

f

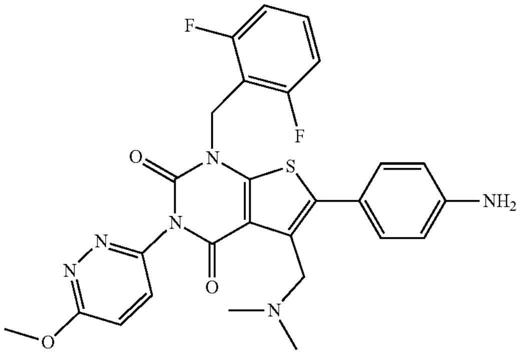

f-2

In one specific embodiment, the present invention provides a new impurity g of API of the thienopyrimidine compound (such as Relugolix).

g

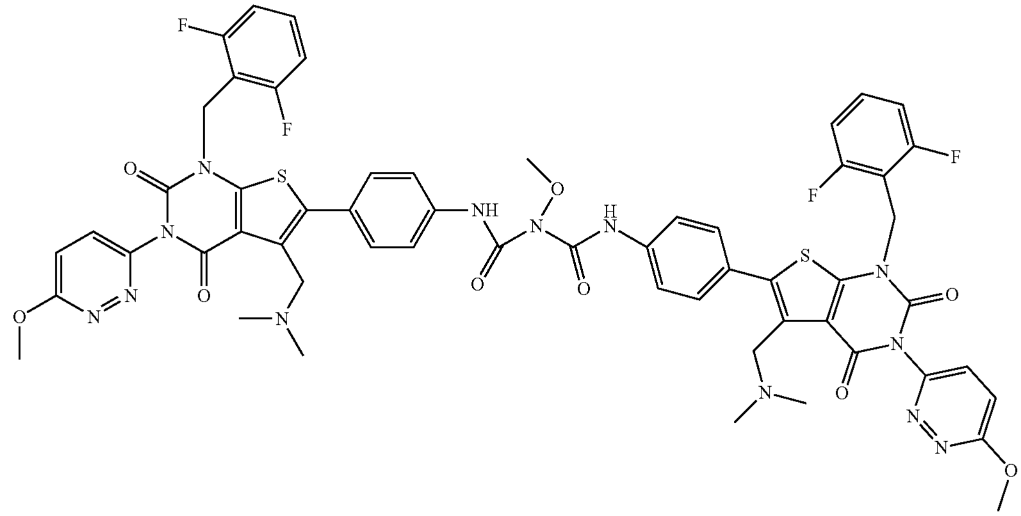

Impurity g is produced when the ring is closed under basic conditions, and the amount produced is positively correlated with the basicity. Impurity g generated from substitution derivatization reaction of two urea groups. This impurity is not easy to purify, and needs to be precisely controlled during reaction process. The amount of generation of this impurity varies greatly depending on the reaction conditions. The generation of impurity g can be confined to less than 0.1%, or even less than 0.05% in the product obtained by the method of the present invention. The source is shown below:

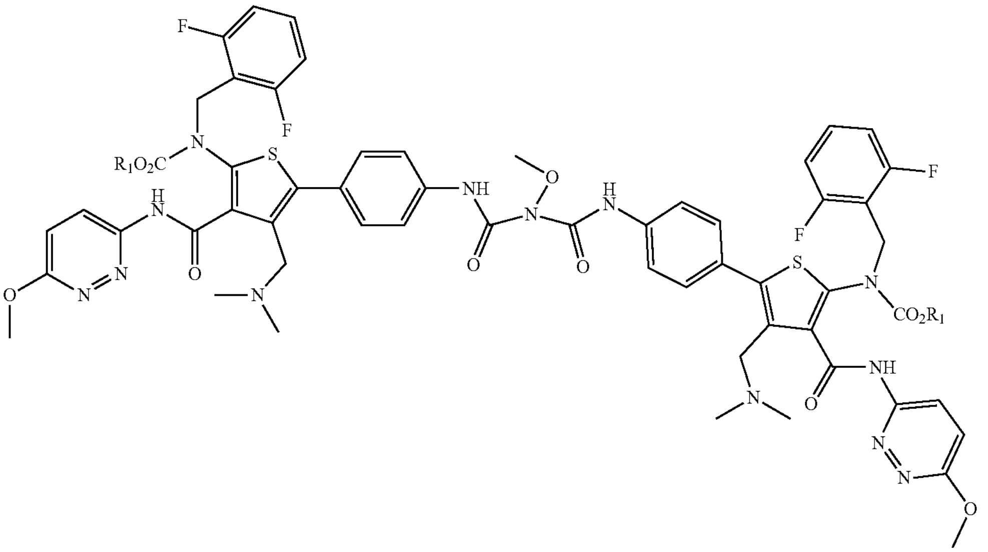

g-1

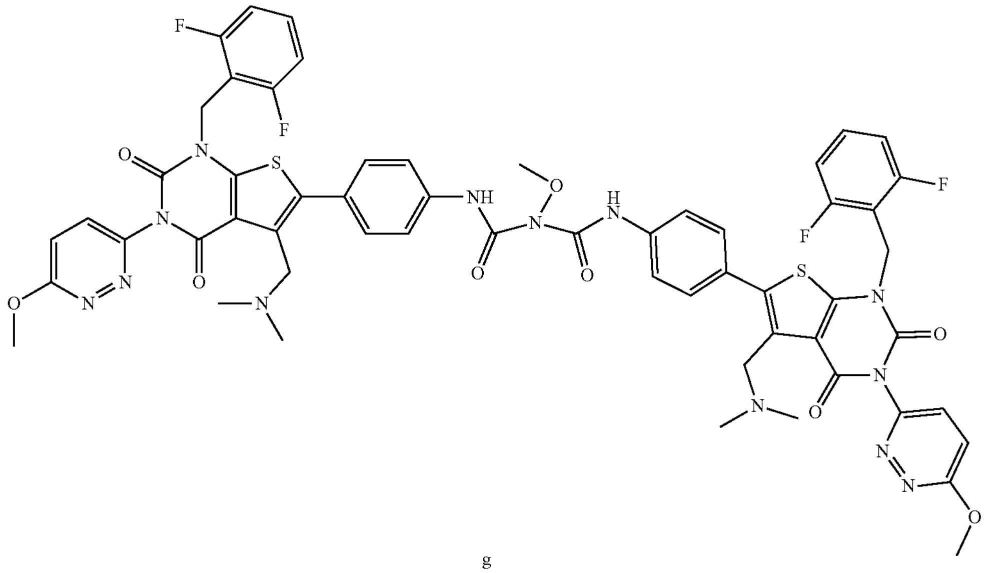

g

-continued

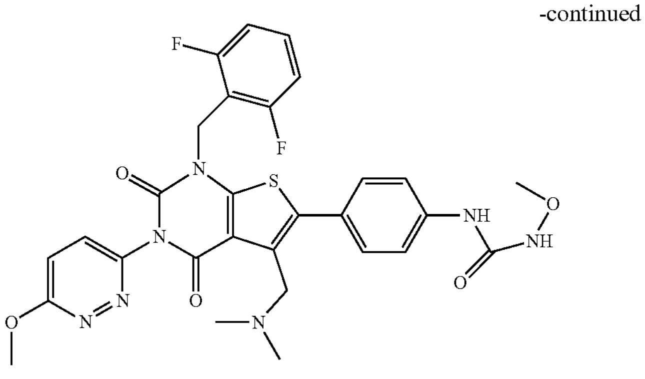

N-a

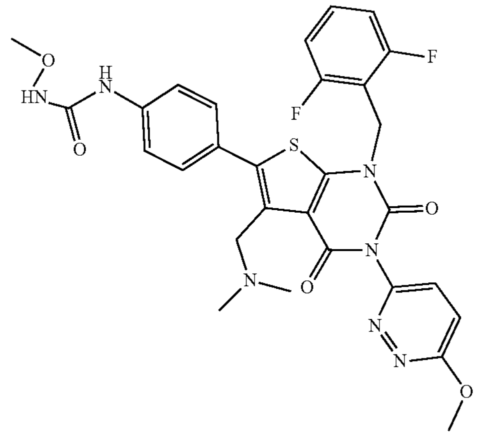

N-a

In one specific embodiment, the present invention provides a new impurity h of API of the thienopyrimidine compound (such as Relugolix).

h

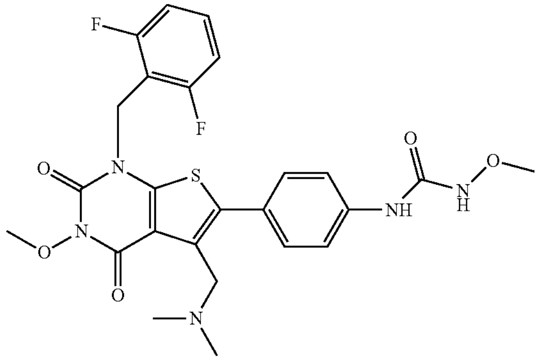

Impurity h is a derivative of the condensation reaction of methoxyamine, residue from previous step or produced by degradation, with intermediate h-2. This impurity requires the control of the residue of methoxyamine prior to the two steps, as well as the well-controlled of the reaction conditions to prevent degradation of the side chain urea to produce methoxyamine. As shown below:

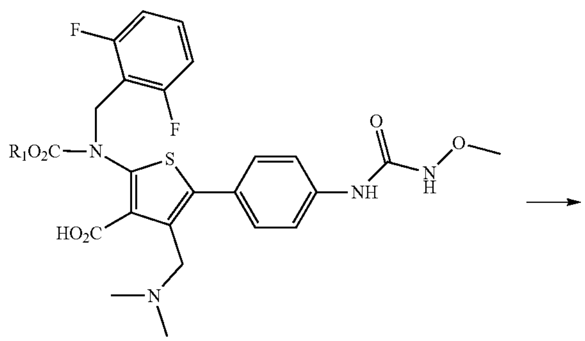

h-2

-continued

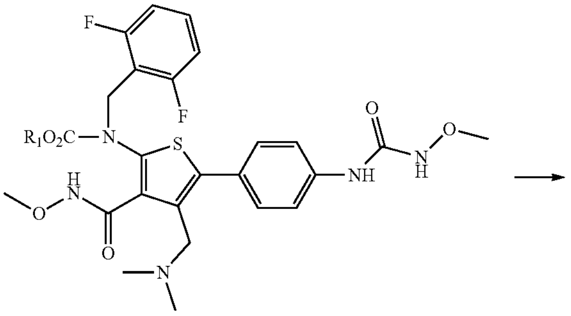

h-1

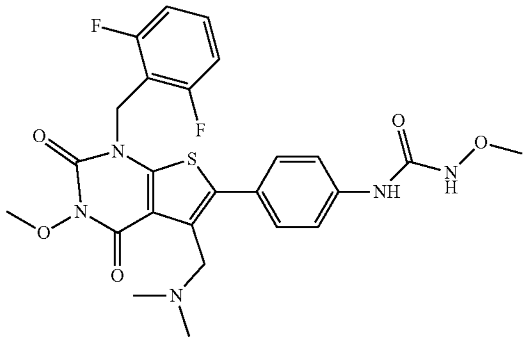

h

In one specific embodiment, the fifth aspect of the impurity study section of the present invention provides a new impurity i of API of the thienopyrimidine compound (such as Relugolix).

i

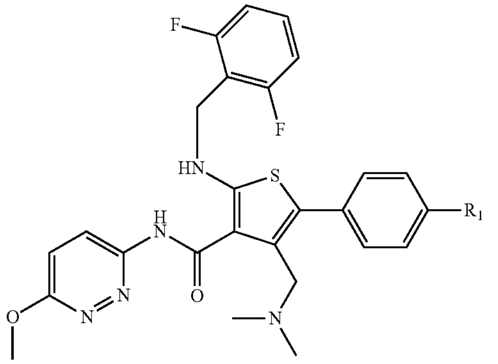

Impurity i originates from the degradation of the six-membered ring structure of uracil under alkaline conditions; the stronger the alkalinity of the alkali used in the reaction, the greater the amount of impurity i produced. In the two routes as shown below:

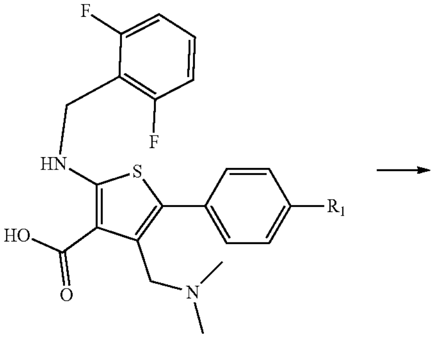

d

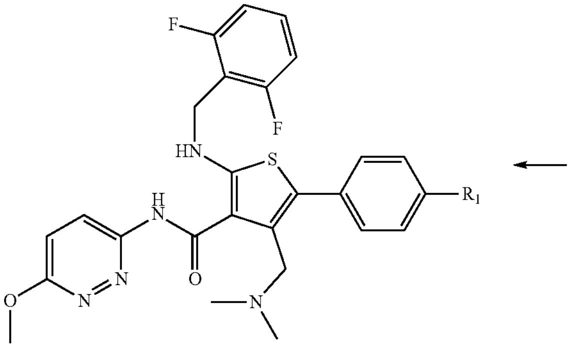

i

-continued

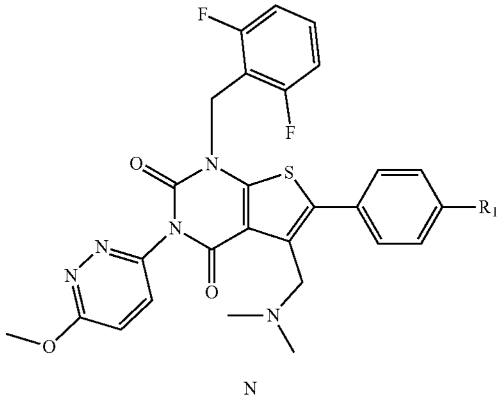

N wherein, $R_1$ is $NO_2$ or $NHCONHOCH_3$.

In one specific embodiment, the present invention provides a new impurity j of API of the thienopyrimidine compound (such as Relugolix).

j

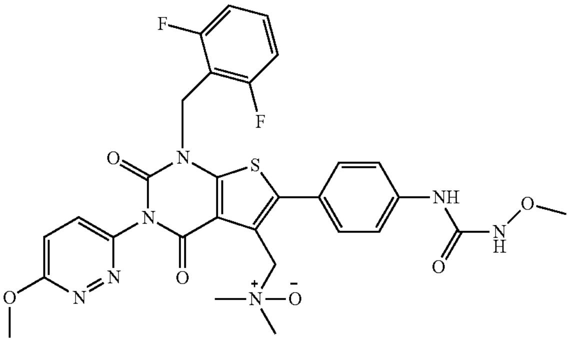

Impurity j is an oxidative degradation impurity of the thienopyrimidine compound (e.g., Relugolix). Impurity j is easily generated in the presence of an oxidizing agent, as shown below:

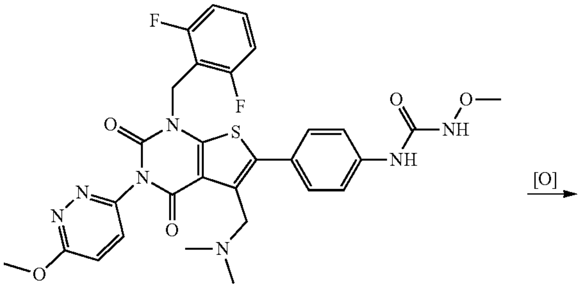

N-a

-continued

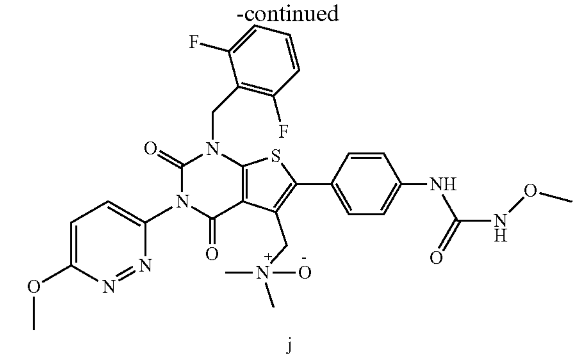

j

In one specific embodiment, the present invention provides a new impurity k of API of the thienopyrimidine compound (such as Relugolix).

k

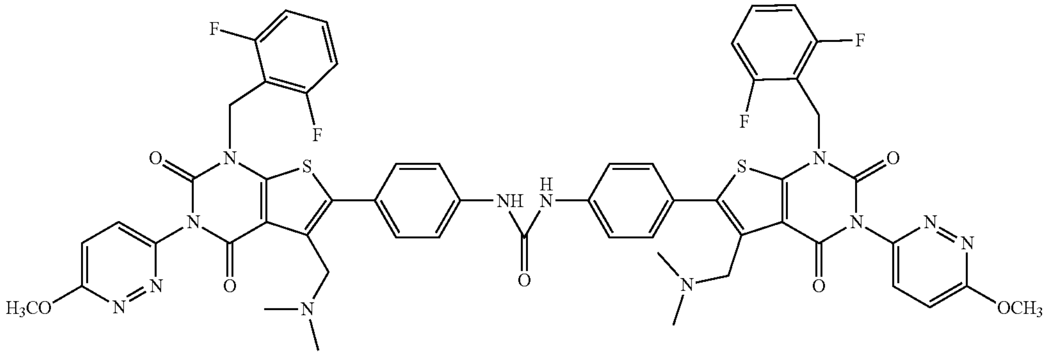

Impurity k is a degradation impurity of the thienopyrimidine compound (e.g., Relugolix), which partly results from the substitution reaction of the urea side chain of two molecules of the thienopyrimidine compound (e.g., Relugolix) or from poor control of the material when generating the side chain in the preceding step. As shown below:

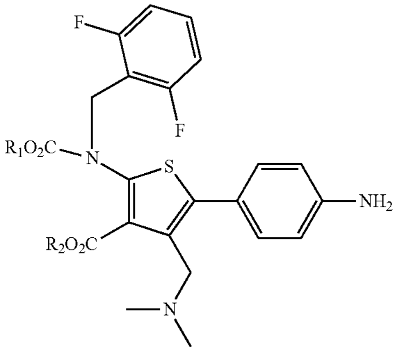

k-3

-continued

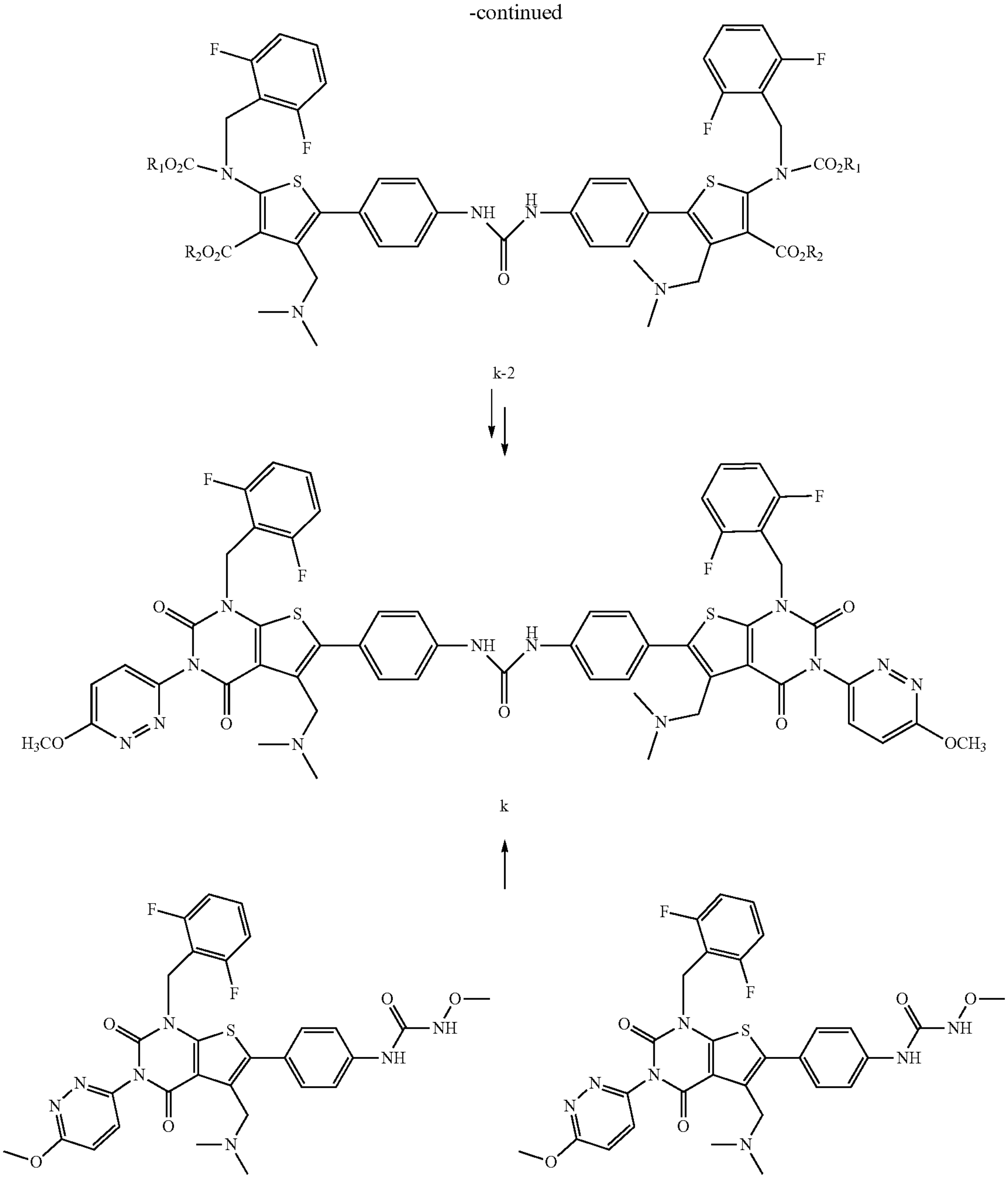

N-a N-a

The Main Advantages of the Present Invention Include (1) There is no need for toxic and expensive reagents (e.g., T3P, etc.), and the reagents used are inexpensive and readily available, which greatly reduces the production cost and is suitable for industrialized mass production.

(2) The method of the present invention has fewer reaction by-products, thus avoiding a variety of impurities that are difficult to separate.

(3) By using the method of the present invention, the chemical purity of the product the compound of formula N-a (e.g., the compound of formula N-a) can be up to 99.7% and a plurality of impurities can be easily controlled to be less than 0.1% upon conducting a single refinement (e.g., recrystallization), without the use of purification methods such as chromatography.

The present invention was further described hereafter in combination with specific embodiments. It should be understood that these examples are only used to illustrate the present invention and not to limit the scope of the invention. The experimental methods without specific conditions in the following examples generally follow the conventional conditions or the conditions suggested by the manufacturer. Unless otherwise stated, percentages and parts are percentages by weight and parts by weight.

Materials and General Methods

1. The raw materials used in the examples were prepared with reference to WO2004067535, WO2014051164, and CN111333633A.
2. Determination method for nuclear magnetic resonance $^1$H-NMR 300 MHz, Bruker AV III 300 spectrometer.

Example 1: Preparation of Impurity e-a Reference Substance

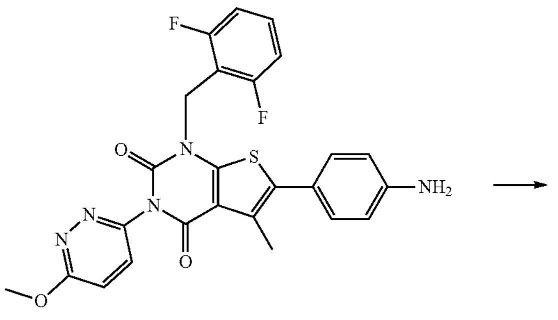

e-2

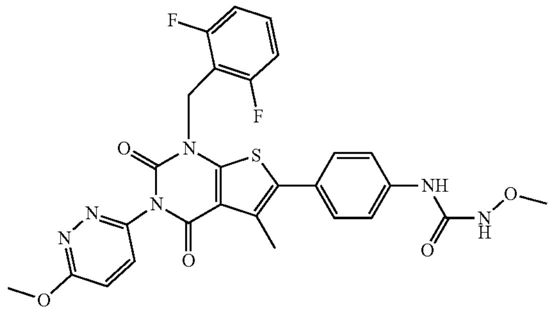

e-a 0.52 g of N,N'-carbonyldiimidazole was dissolved in 3 ml acetonitrile, 0.2 g of triethylamine and 0.3 g of methoxyamine hydrochloride were added. The mixture was stirred for 10 minutes. The mixture was added with 1.0 g of the compound of formula e-2, and warmed to 45-55° C. TLC tracked until the complete conversion of the raw material, and the mixture was cooled to 15-25° C. The solution was added dropwise with 4 ml of water, and after dripping, continued to stir for 2 hours. The mixture was filtered and dried to obtain 1.05 g of impurity e, with an HPLC purity of 98.8%. $^1$H-NMR (300 MHz, $CDCl_3$) δ: 2.46 (3H, s), 3.82 (3H, s), 4.19 (3H, s), 5.33 (2H, s), 6.92 (2H, t, J=8.1 Hz), 7.14 (1H, d, J=9.1 Hz), 7.33 (2H, d, J=8.5 Hz), 7.40 (1H, d, J=9.1 Hz), 7.55 (2H, d, J=8.5 Hz), 7.67 (1H, s).

Example 2: Preparation of Impurity f (R=OMe) Reference Substance

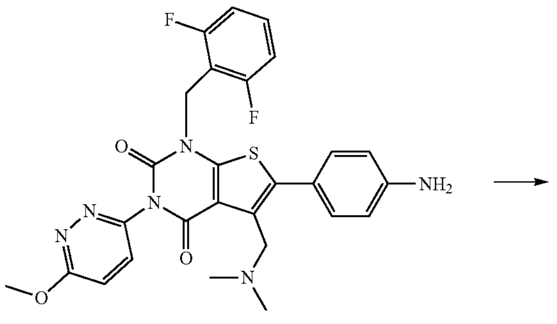

f-2

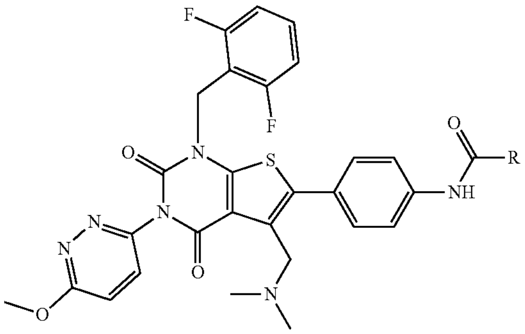

f 5.0 g of Relugolix intermediate f-2 was taken and dissolved in 50 ml of dichloromethane, and 1.3 g of triphosgene was added. The mixture was cooled to 0 to 10° C., and added dropwise with 2.2 g of pyridine. After reacting for 1 hour, 5 ml of methanol was added. The mixture was warmed to 15 to 25° C. and reacted until the raw material being completely converted. The reaction mixture was concentrated under reduced pressure, purified through column chromatography to obtain 3.90 g of compound f with a HPLC purity of 98.5%, 1H-NMR (300 MHz, DMSO-d6) δ: 2.58 (6H, s), 3.69 (3H, s), 4.09 (3H, s), 4.38 (2H, s), 5.35 (2H, d, J=55.1 Hz), 7.16 (2H, t, J=8.2 Hz), 7.42-7.51 (4H, m), 7.64 (2H, d, J=8.6 Hz), 7.82 (1H, d, J=9.2 Hz), 9.10 (1H, s), 10.01 (1H, s).

Example 3: Preparation of Impurity f (R=$NH_2$) Reference Substance

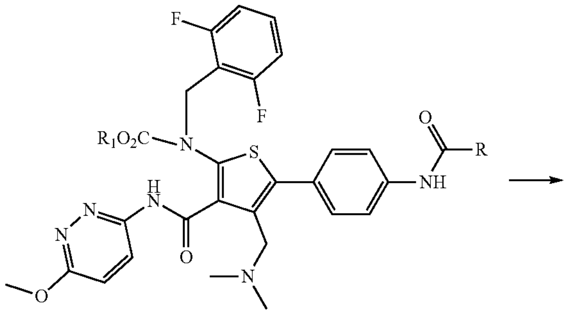

f-3

-continued

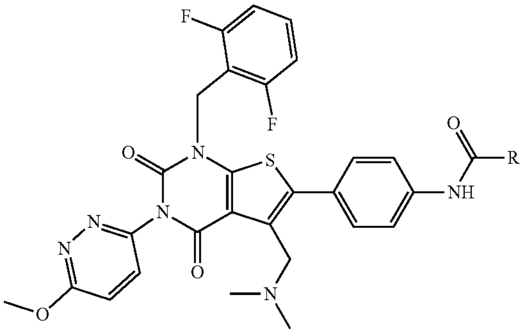

f 5.0 g of Relugolix intermediate f-1 was taken and dissolved in 50 ml of dichloromethane, and 1.3 g of triphosgene was added. The mixture was cooled to 0 to 10° C., and added dropwise with 2.2 g of pyridine. After reacting for 1 hour, 5 ml of ammonia was added. The mixture was warmed to 15 to 25° C. and reacted until the raw material being completely converted. The reaction mixture was concentrated under reduced pressure, purified through column chromatography to obtain 2.60 g of compound f with a HPLC purity of 97.5%, 1H-NMR (300 MHz, DMSO-d6) δ: 2.03 (6H, s), 3.57 (2H, d, J=35.2 Hz), 4.09 (3H, s), 5.30 (2H, d, J=45.3 Hz), 5.95 (2H, s), 7.15 (2H, t, J=8.2 Hz), 7.41-7.53 (6H, m), 7.75 (1H, d, J=9.2 Hz), 8.75 (1H, s).

Example 4: Preparation of Impurity g Reference Substance

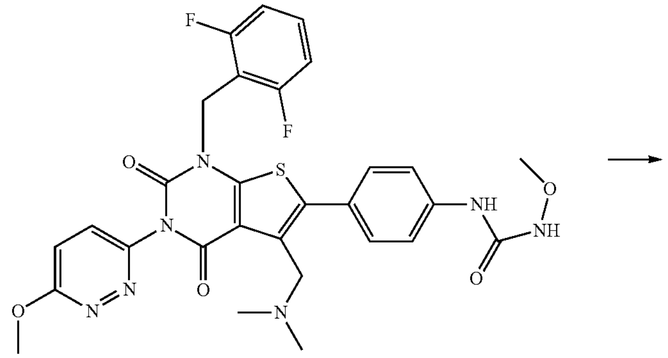

N-a

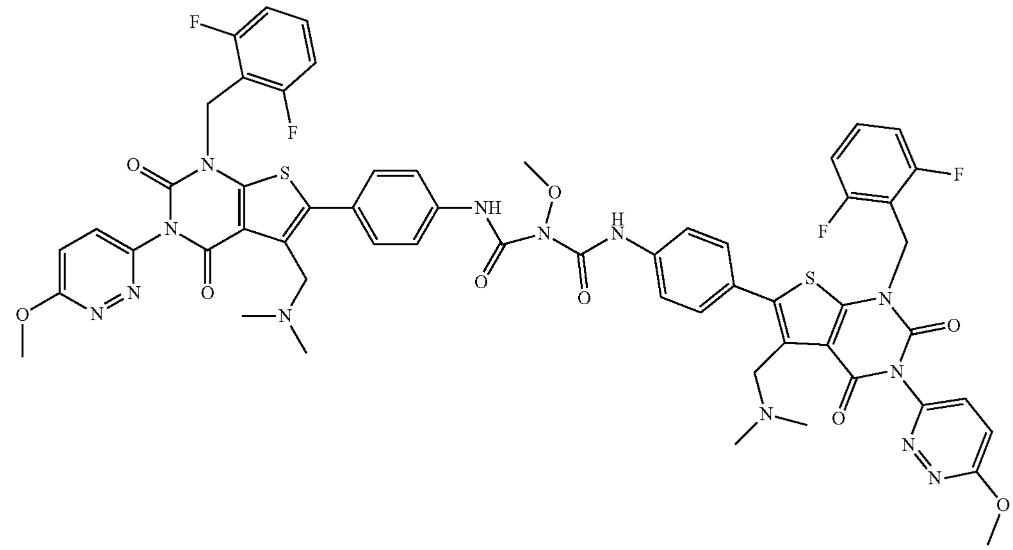

g 10.0 g of Relugolix was taken and dissolved in 500 ml of dimethyl sulfoxide, and 2.2 g of anhydrous potassium carbonate was added. The mixture was warmed to 30 to 40° C. and reacted until most of the raw material being completely converted. The reaction solution was added dropwise to 500 ml of water. Upon addition, the mixture was stirred for 2 hours, filtered to obtain 9 g of crude product. The crude product was purified by column chromatography to obtain 0.60 g of compound g with a HPLC purity of 95.8%, 1H-NMR (300 MHz, DMSO-d6) δ: 2.03 (12H, s), 3.58 (4H, d, J=33.1 Hz), 3.85 (3H, s), 4.06 (6H, s), 5.27 (4H, d, J=43.1 Hz), 7.12 (4H, t, J=8.1 Hz), 7.43 (4H, d, J=9.0 Hz), 7.58-7.75 (10H, m), 10.33 (2H, s).

Example 5: Preparation of Impurity h ($R_1$=iPr) Reference Substance

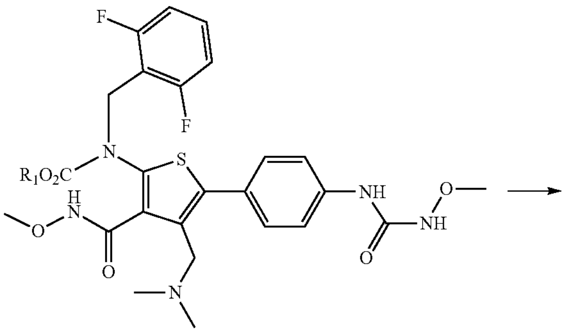

h-1

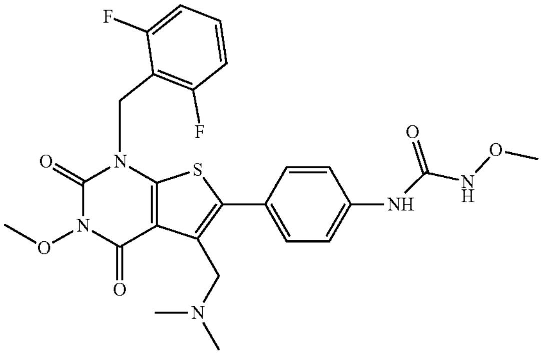

h 10.0 g of Relugolix intermediate h-1 was taken and dissolved in 50 ml of dimethyl sulfoxide, and 2.4 g of anhydrous potassium carbonate was added. The mixture was warmed to 40 to 50° C. and reacted until most of the raw material being completely converted. The reaction solution was cooled to 15 to 25° C. and added dropwise with 100 ml of water. Oily substance was precipitated and the mixture was liquid separated. The crude oily substance was purified by column chromatography to obtain 5.20 g of compound h with a HPLC purity of 97.5%, 1H-NMR (300 MHz, DMSO-d6) δ: 2.08 (6H, s), 3.63 (5H, s), 3.87 (3H, s), 5.30 (2H, s), 7.14 (2H, t, J=8.3 Hz), 7.41-7.53 (3H, m), 7.69 (2H, d, J=8.6 Hz), 9.06 (1H, s), 9.62 (1H, s).

Example 6: Preparation of Impurity i (Formula i-a, $R_1$=$NHCONHOCH_3$) Reference Substance

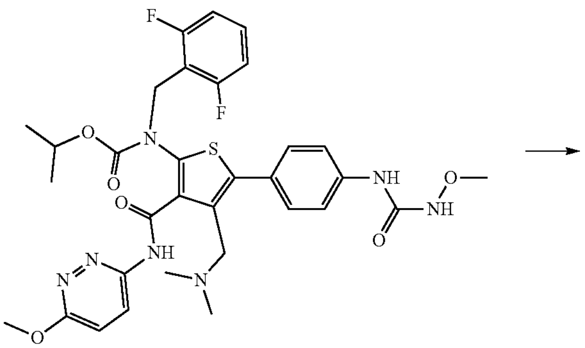

i-1

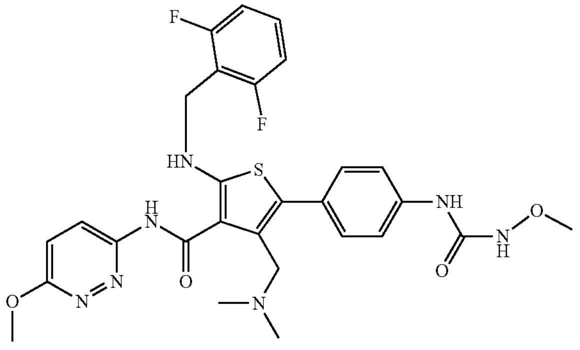

i 1.0 g of Relugolix intermediate i-1 was taken and dissolved in 20 ml of methanol, and 0.82 g of anhydrous potassium carbonate was added. The mixture was warmed to 30 to 40° C., reacted until most of the raw material being completely converted, and concentrated under reduced pressure. The crude oily substance was purified by column chromatography to obtain 0.50 g of compound i with a HPLC purity of 96.7%, 1H-NMR (300 MHz, $CDCl_3$) δ: 2.30 (6H, s), 3.47 (2H, s), 3.83 (3H, s), 4.08 (3H, s), 4.50 (2H, d, J=5.9 Hz), 6.86-6.99 (3H, m), 7.21-7.31 (3H, m), 7.53 (2H, d, J=8.6 Hz), 7.63 (1H, s), 7.40 (1H, d, J=9.5 Hz), 8.90 (1H, t, J=6.0 Hz), 14.45 (1H, s).

Example 7: Preparation of Impurity j Reference Substance

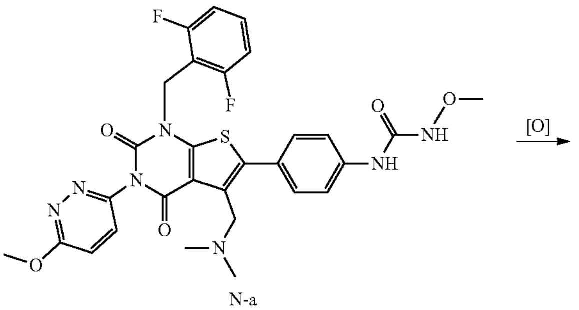

N-a

-continued

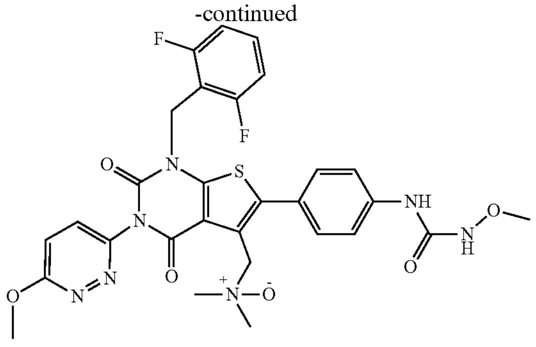

j 4.0 g of Relugolix was taken and dissolved in 80 ml acetonitrile, and 4.0 g of 30% hydrogen peroxide was added. The mixture was warmed to 15 to 25° C., reacted until most of the raw material being completely converted, and concentrated under reduced pressure. The residue was purified by column chromatography to obtain 2.20 g of compound j with a HPLC purity of 98.5%, 1H-NMR (300 MHz, DMSO-d6) δ: 2.82 (6H, s), 3.62 (3H, s), 4.09 (3H, s), 4.72 (2H, s), 5.32 (2H, d, J=36.6 Hz), 7.15 (2H, t, J=8.2 Hz), 7.42-7.51 (2H, m), 7.70 (2H, d, J=8.7 Hz), 7.73-7.82 (3H, m), 9.25 (1H, s), 9.89 (1H, s).

Example 8: Preparation of Impurity k Reference Substance

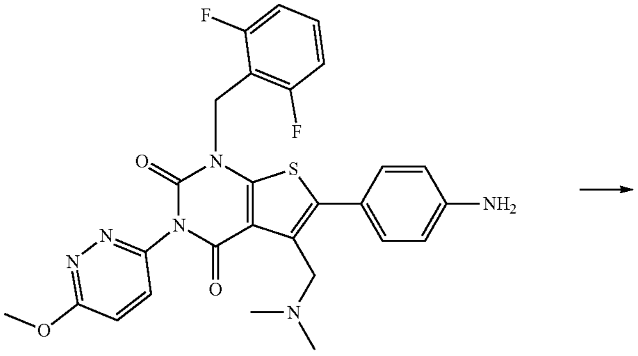

f-2

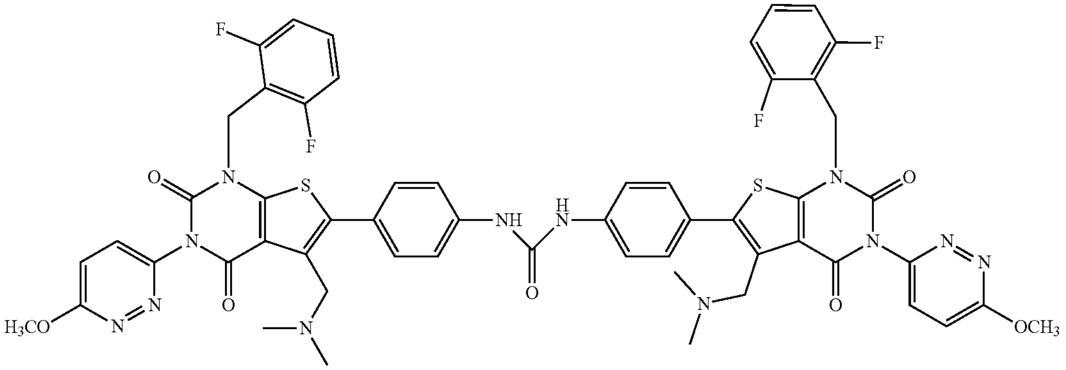

k 5.0 g of Relugolix intermediate f-2 was taken and dissolved in 50 ml of dichloromethane, and 0.5 g of triphosgene was added. The mixture was cooled to 0 to 10° C., and added dropwise with 1.1 g of pyridine. After dripping, the mixture was allowed to warm to room temperature and reacted until most of the raw material being completely converted. The reaction mixture was filtered and the filter cake was purified through column chromatography to obtain 1.60 g of compound f with a HPLC purity of 97.8%, $^1$H-NMR (300 MHz, DMSO-d6) δ: 2.62 (12H, s), 4.10 (6H, s), 4.42 (4H, s), 5.35 (4H, d, J=53.9 Hz), 7.18 (4H, t, J=8.2 Hz), 7.44-7.56 (8H, m), 7.67 (4H, d, J=8.6 Hz), 7.21 (2H, m), 10.18 (2H, s).

Example 9: Preparation of Compound of Formula N-a

Step a: Preparation of Compound of Formula N-la

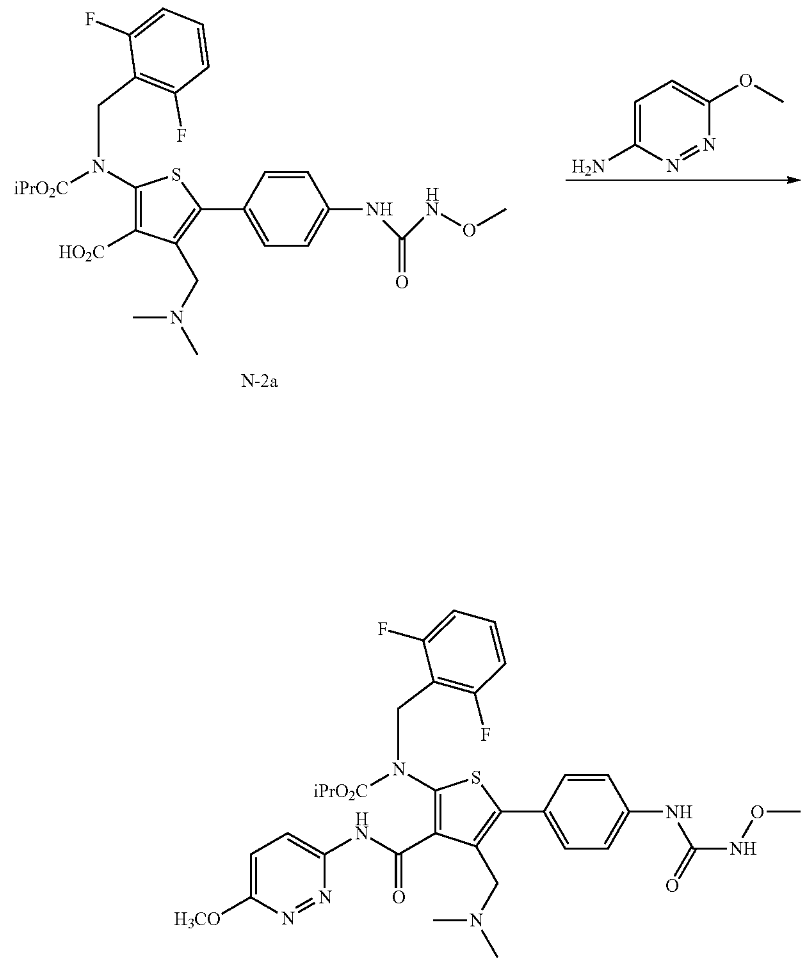

N-2a

N-1a

The compound of formula N-2a (10.5 g, 18.2 mmol, HPLC purity 97.77%) was added to 50 ml DMF and the mixture was cooled to −10 to 0° C. Triethylamine (3.8 g, 37.5 mmol) was added, and sulfoxide dichloride (3.40 g, 28.6 mmol) was added dropwise. 6-methoxy-3-amidopyridaazine (3.58 g, 28.6 mmol) was added in batch after dripping, and the mixture was reacted while keeping the temperature for 10 hours. The HPLC detection and analysis pattern is shown in FIG. 1 (the purity of the product in the reaction solution is 93.56%, and the yield is 93.5%).

Figure 2:
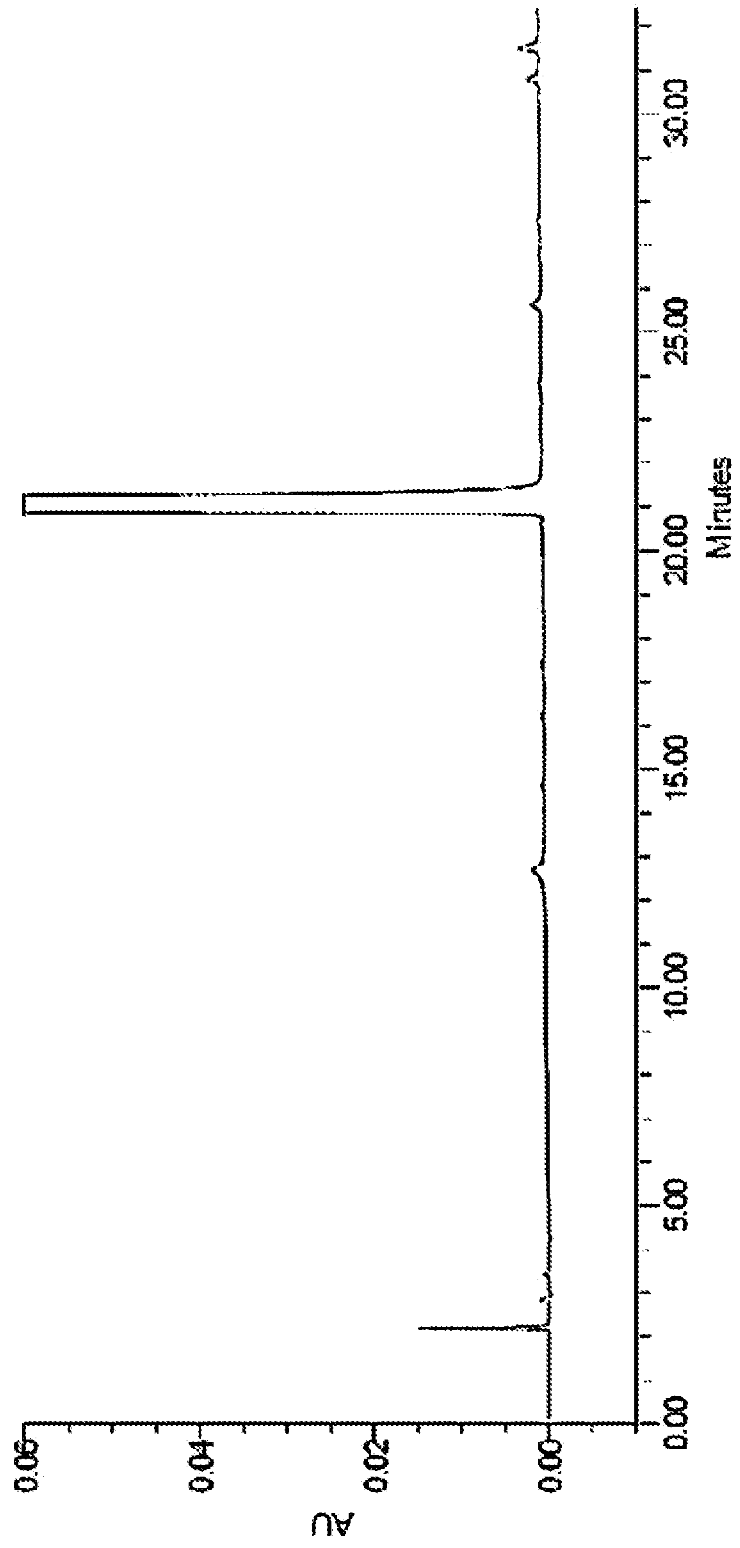
FIG. 2 shows the HPLC detection and analysis graph of purified product in step a of example 9.

The solid was precipitated by dripping with 50 ml of saturated sodium bicarbonate solution at 0 to 10° C. The mixture was filtrated, washed with water, concentrated, and recrystallized with 50 ml ethyl acetate to obtain 11.25 g of yellow solid, with a molar yield of 90.0% and a HPLC purity of 99.11%. The HPLC detection and analysis pattern is shown in FIG. 2. $^1$H-NMR (300 MHz, DMSO-d6) δ: 0.9~1.44 (6H, br.), 2.1 (6H, s), 3.56 (2H, s), 3.64 (3H, s), 4.00 (3H, s), 4.70~5.10 (3H, br.), 6.90~7.10 (2H, t, J=8.5 Hz), 7.10-7.40 (4H, m), 7.60~7.80 (2H, d, J=8.5 Hz), 8.30~8.50 (2H, d, J=9.5 Hz), 9.11 (1H, s), 9.65 (1H, s).

Step b: Preparation of the Compound of Formula N a

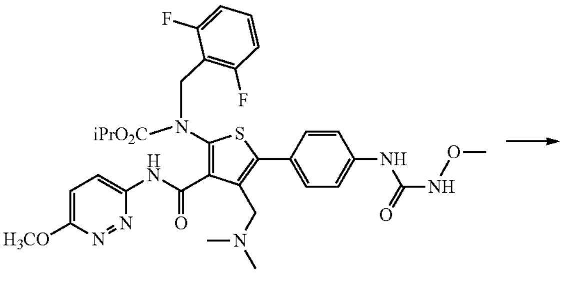

N-1a

-continued

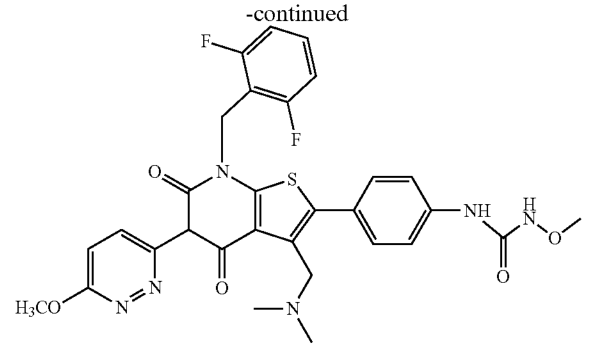

N-a

Figure 6:
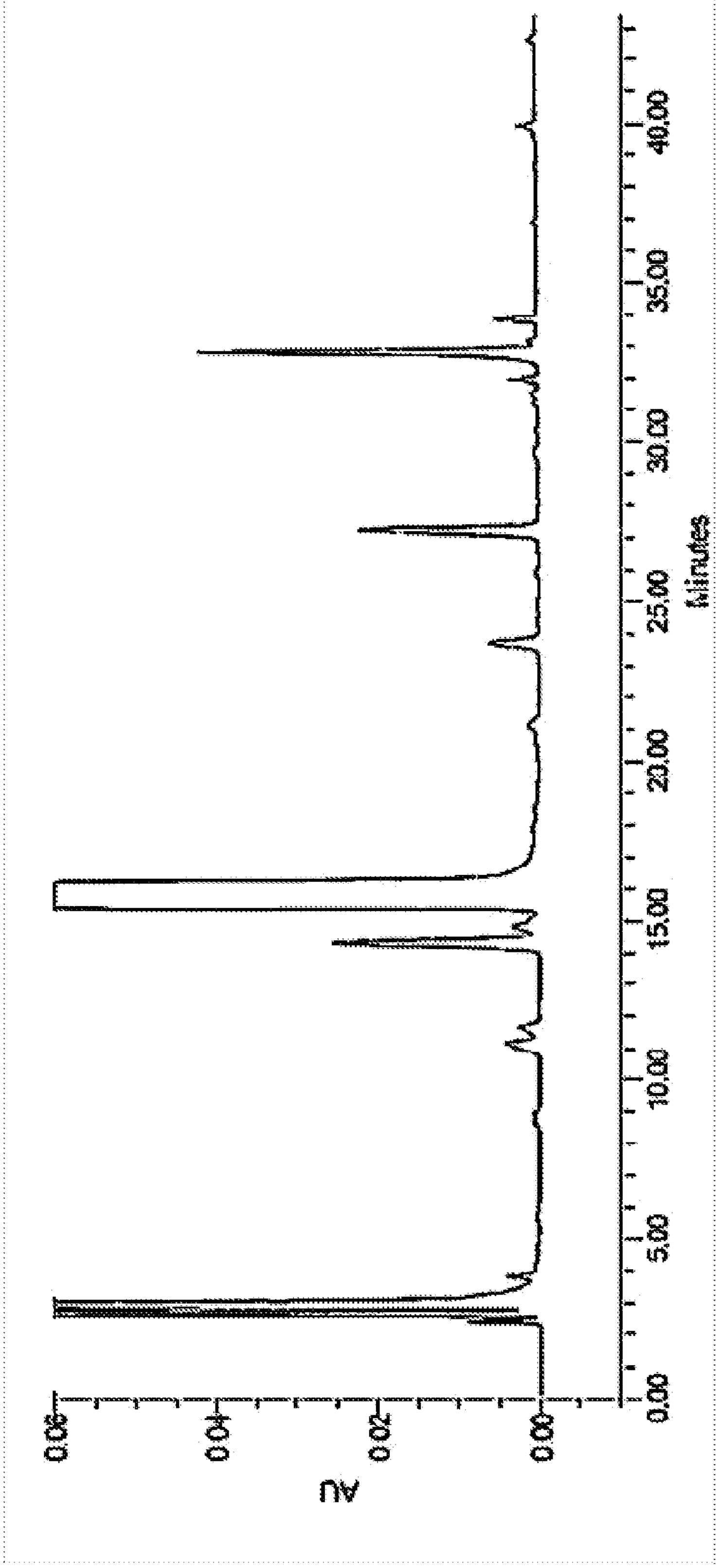
FIG. 6 shows the HPLC detection and analysis graph of the crude product in step b of example 9.

The compound of formula N-la (5.0 g, 7.3 mmol) obtained in step a and potassium carbonate (0.8 g, 5.8 mmol) was added to 50 ml of DMF and the mixture was warmed to 40 to 50° C. and continued to stir for 6 hours. The mixture was cooled to 0 to 10° C., and 100 ml of water was added. The mixture was filtrated and dried to obtain 4.4 g of white solid, with a yield of 96.5% and a purity of 97.58%. The HPLC detection and analysis pattern is shown in FIG. 6.

Figure 7:
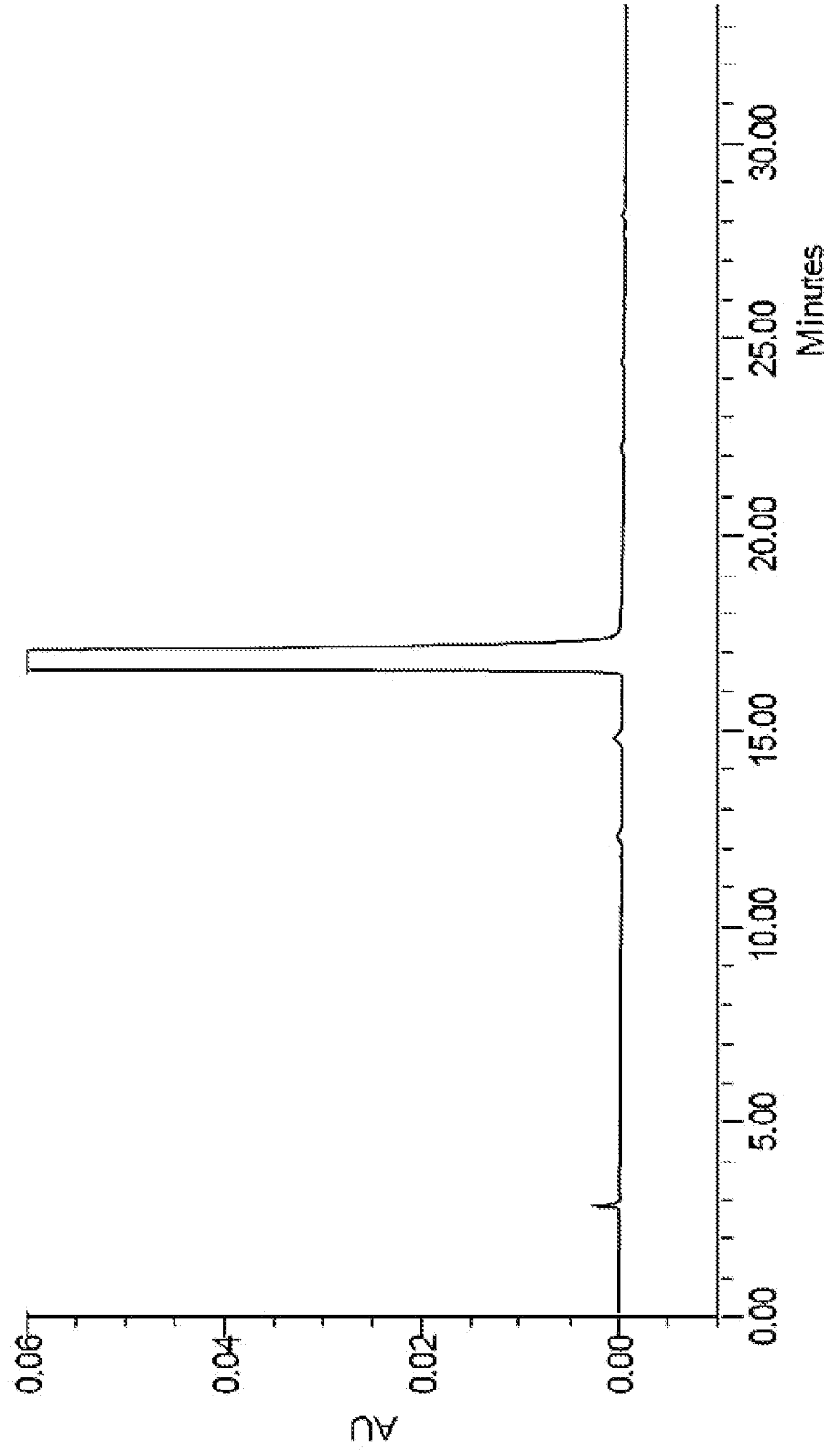
FIG. 7 shows the HPLC detection and analysis graph of purified product in step b of example 9.

The crude product was added with 8.8 ml DMSO, and heated to 40° C. to dissolve. The temperature was controlled at 35 to 45° C., 22 ml of ethanol was added, and the mixture was kept at 35 to 45° C. for 2 hours. The mixture was cooled to 0 to 5° C., and stirred for 2 hours. The mixture was filtrated and dried to obtain 4.1 g of compound of formula N-a, with a yield of 93.2%. The HPLC detection and analysis pattern is shown in FIG. 7 (purity 99.75). $[M+H]^+$: 624.31; 1H-NMR (300 MHz, DMSO-d6) δ: 2.04 (6H, s), 3.40~3.70 (2H, br.), 3.64 (3H, s), 4.09 (3H, s), 5.10~5.50 (2H, br.), 7.10~7.20 (2H, t, J=8.2 Hz), 7.40-7.60 (4H, m), 7.80~7.92 (3H, m), 9.10 (1H, s), 9.63 (1H, s).

Purity and impurities detected by HPLC were as follows (%):

| Formula N-a | RS-1 | RS-2 | RS-3 | Impurity e-a | Impurity f | Impurity g | Impurity h | Impurity i-a | Impurity j | Impurity k | Impurity l |
|---|---|---|---|---|---|---|---|---|---|---|---|
| 97.58 | N.D. | 0.57 | N.D. | 0.52 | 0.15 | 0.08 | 0.10 | 0.30 | N.D. | 0.05 | 0.02 |
| 99.75 | N.D. | 0.09 | N.D. | N.D. | 0.03 | 0.03 | N.D. | N.D. | N.D. | 0.02 | N.D. |

N.D.: not detected (<0.01%)

Comparative Example 1: Condensation Step

Comparative Example 1.1

Figure 3:
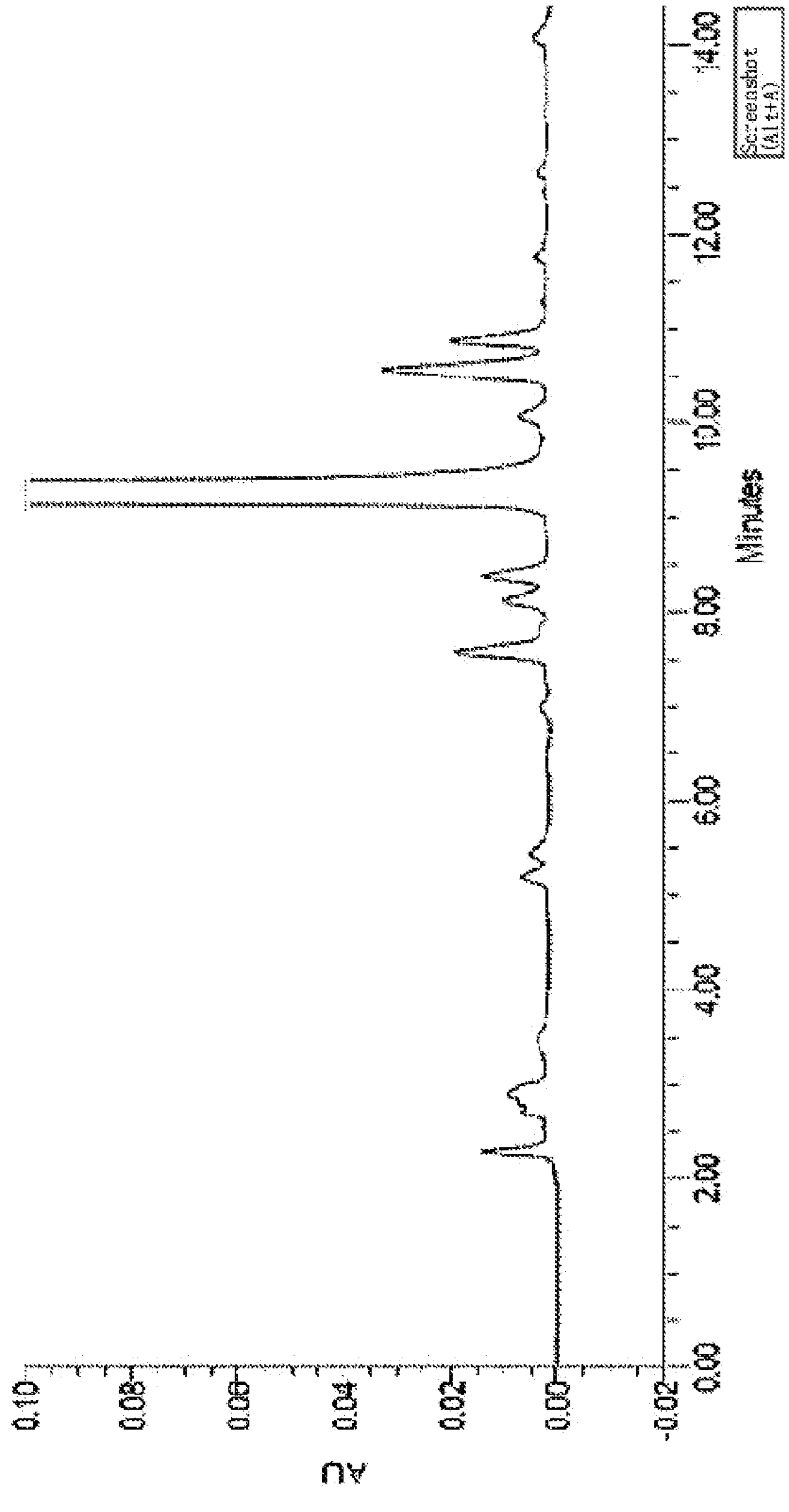
FIG. 3 shows the HPLC detection and analysis graph after heating to 60° C. and reacting for 0.5 hour in comparative example 1.1.

To a 100 mL reaction flask were successively added: N-2a (2.50 g, 4.34 mmol, purity 97.77%), N, N-dimethylacetamide (25 ml), 3-amino-6-methoxypyridazine (0.79 g, 6.34 mmol), N, N-diisopropylethyl amine (0.77 g, 5.95 mmol), 50% propyl phosphoric anhydride ethyl acetate solution (7.84 g, 12.33 mmol). The system was heated up to 60° C. and reacted while keeping the temperature for 0.5 hours. The system was sampled and sent to liquid phase for detection, and the liquid phase purity was 89.99% (HPLC detection and analysis pattern is shown in FIG. 3).

Comparative Example 1.2

The steps are the same as in Example 1.1, except that the reaction time is 1 hour.

Figure 4:
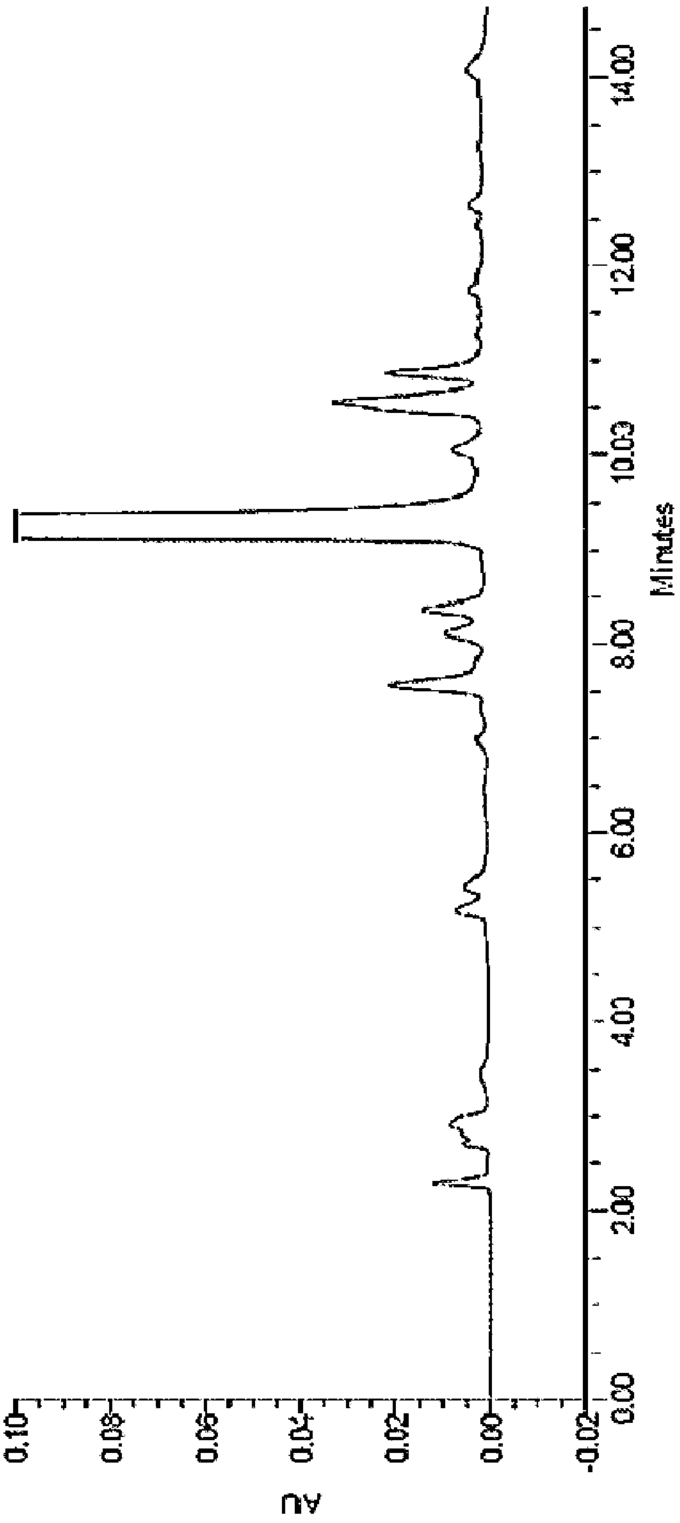
FIG. 4 shows the HPLC detection and analysis graph after heating to 60° C. and reacting for 1 hour in comparative example 1.2.

After sampling and testing, the reaction mixture contained 87.95% of the product after 1 hour (HPLC detection analysis pattern is as shown in FIG. 4), with a yield of 87.5%.

Comparative Example 1.3

The steps are the same as in Example 1.1, except that the reaction time is 2 hour.

Figure 5:
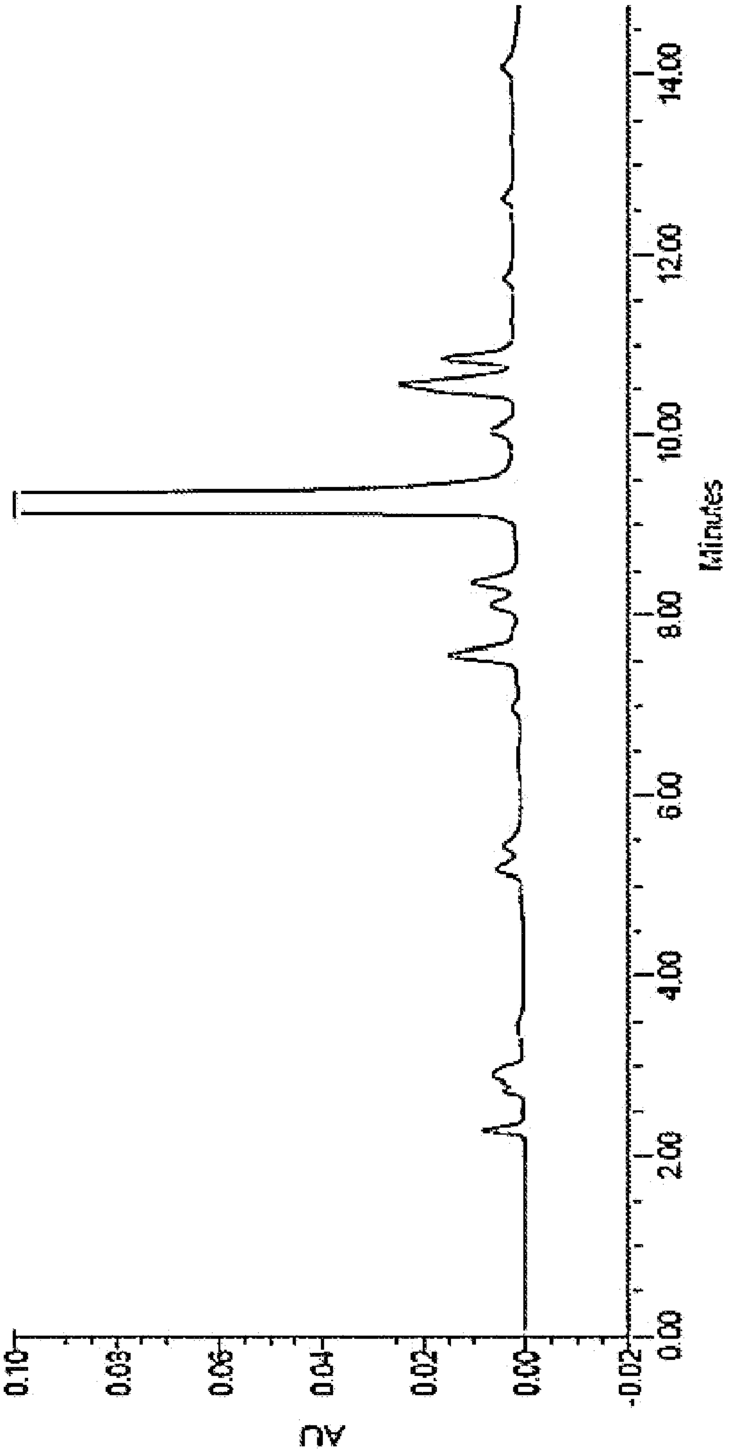
FIG. 5 shows the HPLC detection and analysis graph after heating to 60° C. and reacting for 2 hours in comparative example 1.3.

After sampling and testing, the reaction mixture contained 89.64% of the product after 2 hours (HPLC detection analysis pattern is as shown in FIG. 5), with a yield of 89.5%.

The content of the product in all three tracking experiments did not exceed 90%, thus the crude solid obtained from routine post-treatment after the reaction cannot be purified by crystallization and requires column chromatography purification. When attempting silica gel column chromatography, it was found that this product has poor stability during the column chromatography process, and the purity can not be improved after column chromatography purification.

In addition, the propyl phosphate anhydride (T3P) used in the comparative examples is expensive, and its molar price is much higher than that of the reagent of acyl chloride used in the present application, or even about 50 times the amount of that of the reagent thionyl chloride used. Moreover, T3P has a large molecular weight and low atomic utilization rate, and can only be transported and stored in solution. Post-treatment of 1 molecule of propyl phosphate anhydride will produce 3 molecules of phosphorus-containing waste water, which is harmful to the environment.

Comparative Example 1.4

To a 100 mL reaction flask were successively added: N-2a (2.50 g, 4.34 mmol, purity 97.77%), N, N-dimethylacetamide (25 ml), 3-amino-6-methoxypyridazine (0.79 g, 6.34 mmol), N, N-diisopropylethyl amine (0.77 g, 5.95 mmol), 1-(3-dimethoxypropyl)-ethylcarbodiimide hydrochloride (1.66 g, 8.68 mmol), and 4-dimethylaminopyridine (0.05 g, 0.41 mmol). The system was warmed to 60° C. and kept for 5 hours. The system was sampled and sent to the liquid phase for detection, and the purity was 50.88%.

Comparative Example 2: Ring-Closing Step

Comparative Example 2.1

Figure 8:
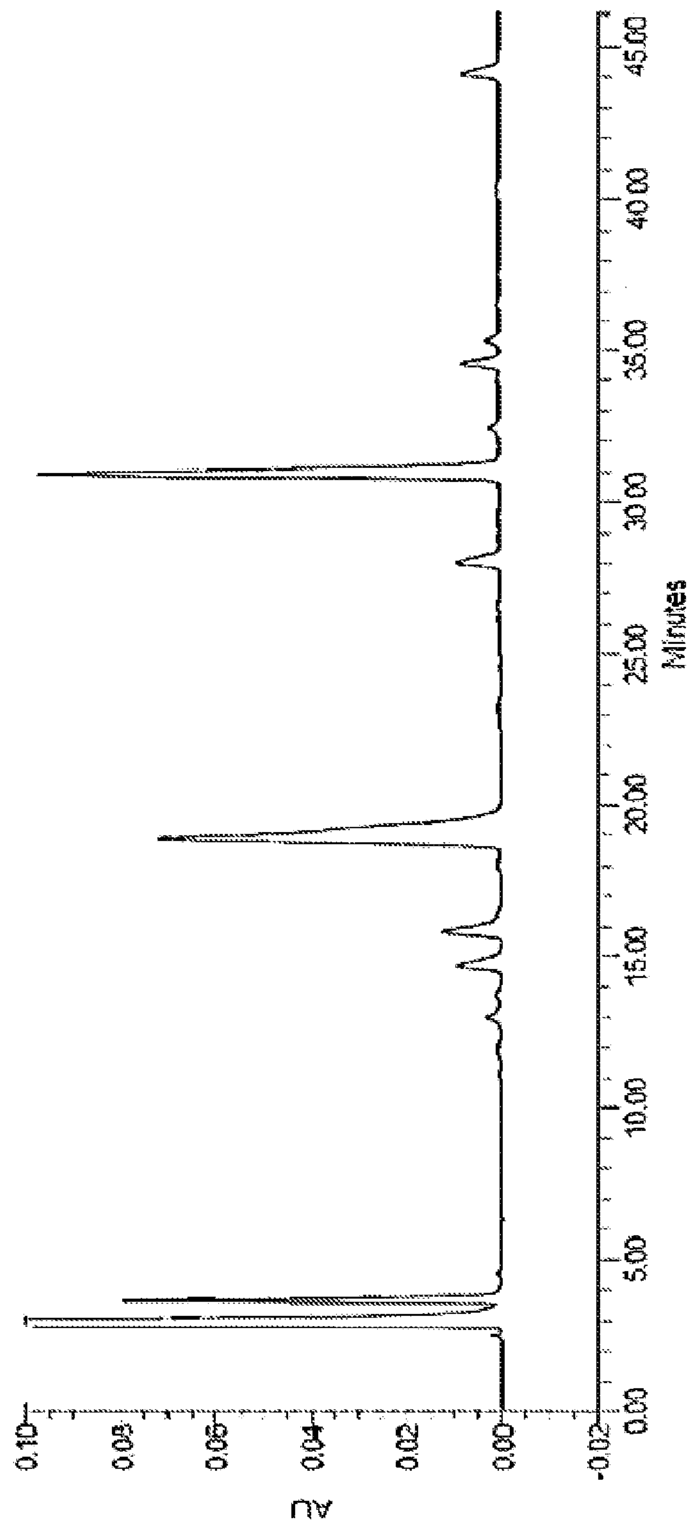
FIG. 8 shows the HPLC detection and analysis graph after heating to 60° C. and reacting for 0.5 hour in comparative example 2.1.

(1) To a 100 mL reaction flask were successively added: N-la (1.50 g, 2.19 mmol, purity 99.11%), isopropanol (35 ml), and sodium ethoxide solid (0.48 g, 7.05 mmol). The resulting system was heated to 70° C., and reacted while keeping the temperature for 0.5 hour before sampling and analysis. After detection, the content of formula N-a (retention time is 15.833 minutes) in the reaction mixture was only 5.08%. HPLC detection analysis pattern is shown in FIG. 8 and Table 1.

(2) To a 100 mL reaction flask were successively added: N-la (1.50 g, 2.19 mmol, purity 99.11%), methanol (35 ml), sodium methoxide solid (0.48 g, 7.05 mmol). The resulting system was heated to 60° C., and reacted while keeping the temperature for 0.5 hour before sampling and analysis. After detection, the content of formula N-a in the reaction mixture was 4.58%.

(3) To a 100 mL reaction flask were successively added: N-1a (1.50 g, 2.19 mmol, purity 99.11%), ethanol (35 ml), sodium ethoxide solid (0.48 g, 7.05 mmol). The resulting system was heated to 60° C., and reacted while keeping the temperature for 1.0 hour before sampling and analysis. After detection, the content of formula N-a in the reaction mixture was 6.26%.

Figure 9:
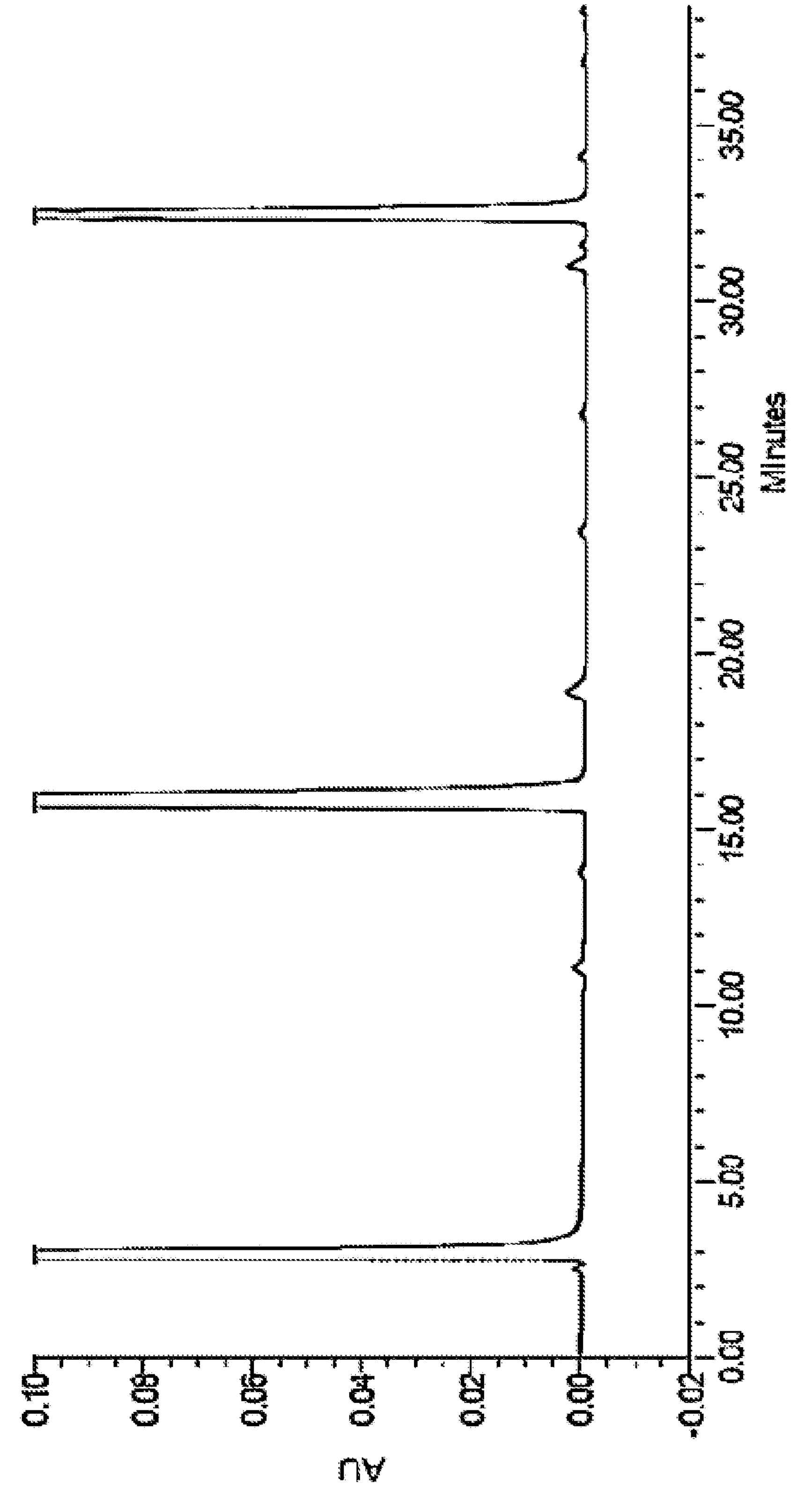
FIG. 9 shows the HPLC detection and analysis graph after heating to 60° C. and reacting for 0.5 hour in comparative example 2.2.

Comparative Example 2.2 (1) To a 100 mL reaction flask were successively added: N-1a (1.50 g, 2.19 mmol, purity 99.11%), ethanol (35 ml), sodium ethoxide solid (0.15 g, 2.19 mmol). The system was heated to 60° C. for 0.5 hour before sampling. The content of formula N-a in the reaction mixture was 63.08% (HPLC analysis pattern is shown in FIG. 9 and Table 1).

Figure 10:
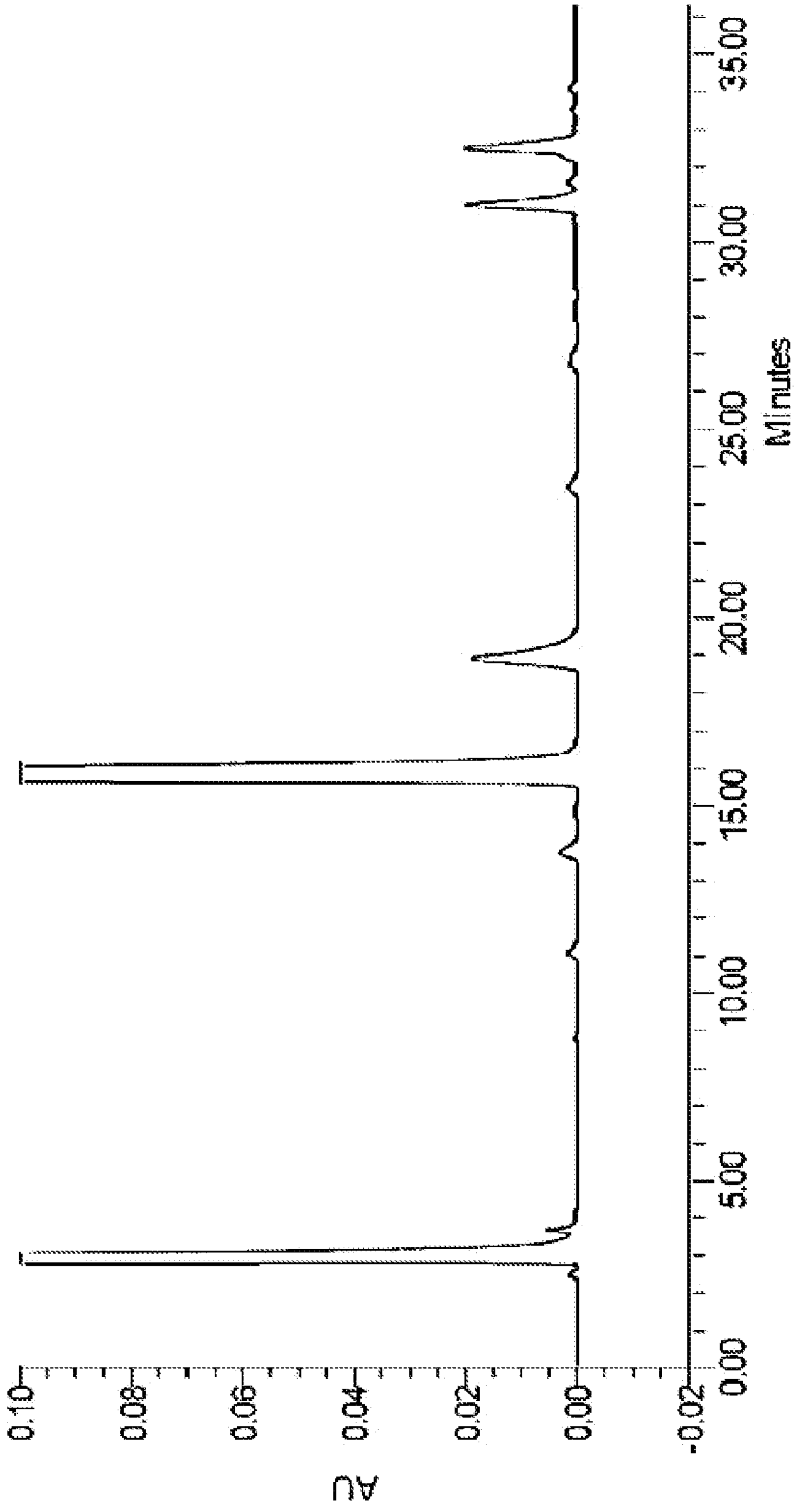
FIG. 10 shows the HPLC detection and analysis graph after heating to 60° C. and reacting for 1 hour in comparative example 2.2.

(2) After sampling at 0.5 hours, the remaining reaction mixture continued to react while keeping the temperature at 60° C., the reaction was sampled at 1 hour (i.e., when continued to react for 0.5 hours) (HPLC analysis results are shown in FIG. 10 and Table 1).

Figure 11:
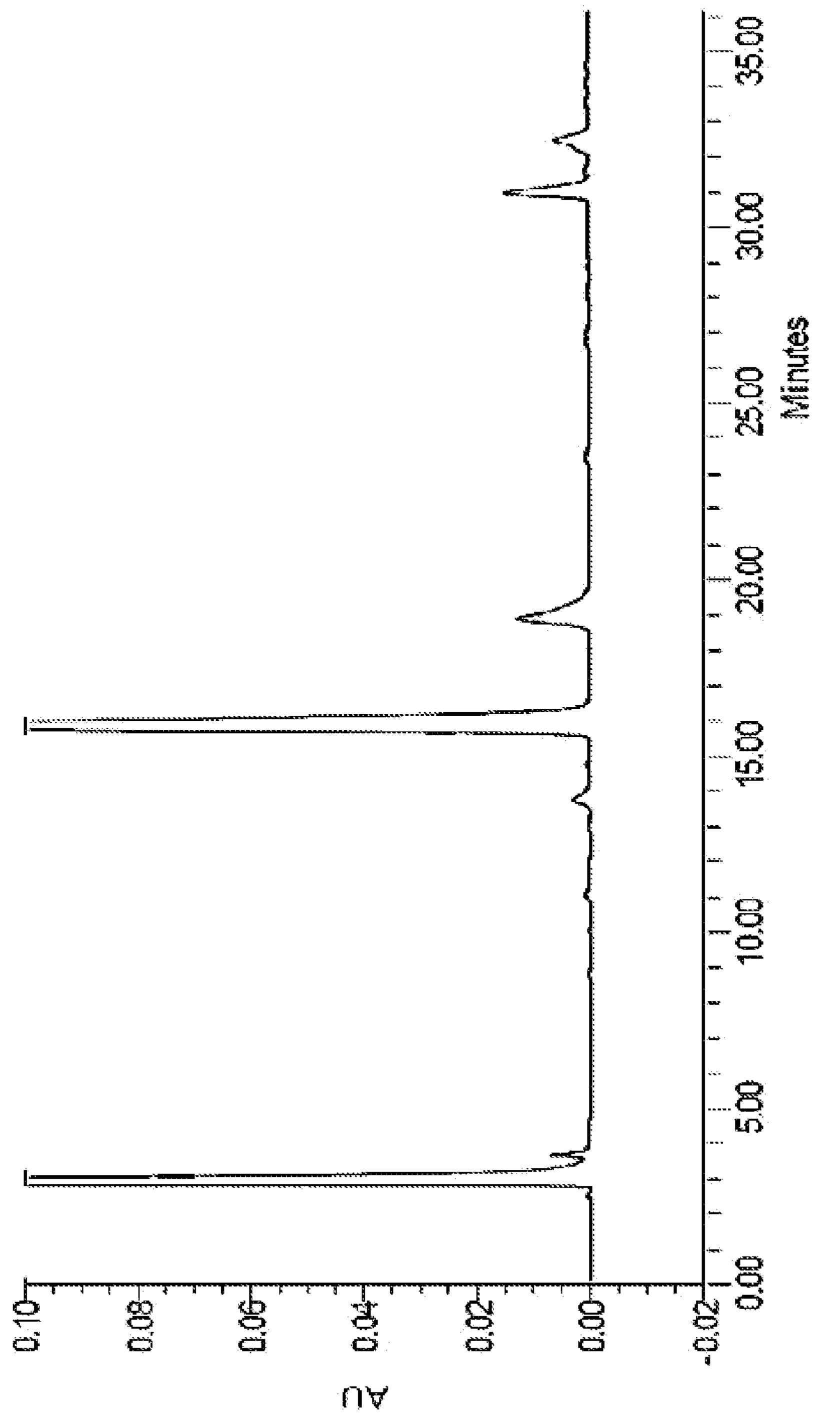
FIG. 11 shows the HPLC detection and analysis graph after heating to 60° C. and reacting for 1.5 hours in comparative example 2.2.

(3) After sampling at 1 hour, the remaining reaction mixture continued to react while keeping the temperature at 60° C., the reaction was sampled at 1.5 hour (i.e., when continued to react for 0.5 hours) (HPLC analysis results are shown in FIG. 11 and Table 1).

Figure 12:
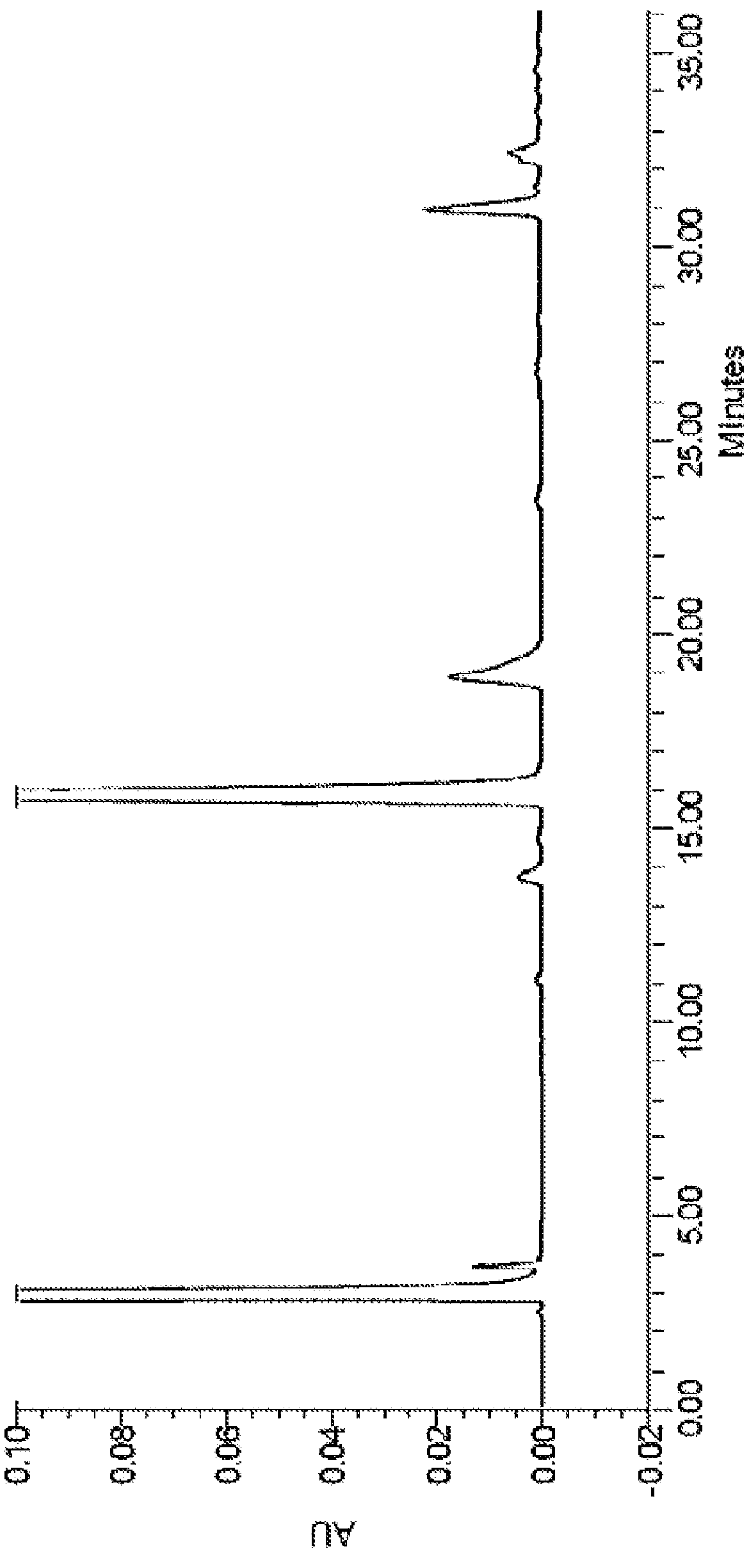
FIG. 12 shows the HPLC detection and analysis graph after heating to 60° C. and reacting for 2 hours in comparative example 2.2.
Figure 13:
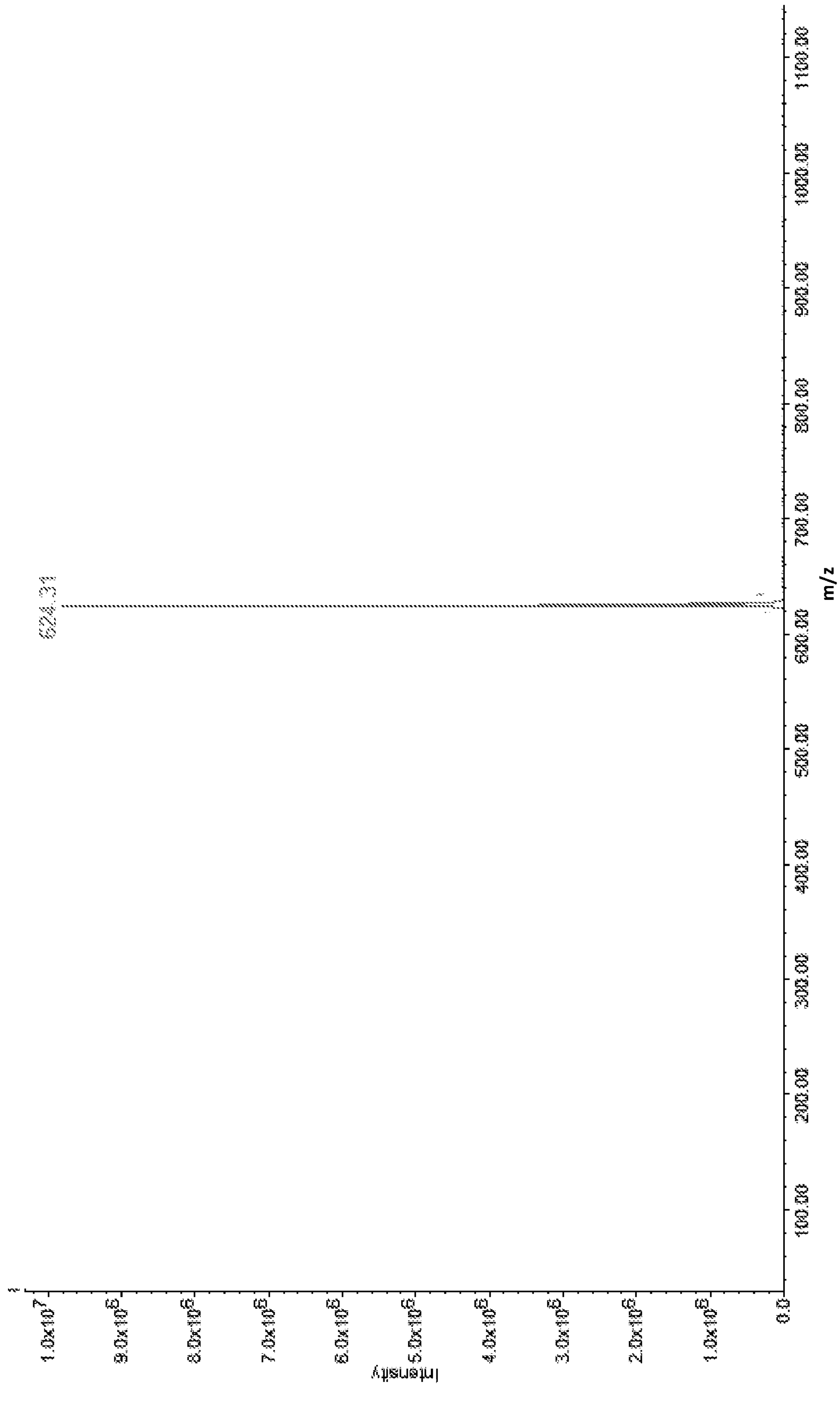
FIG. 13 shows the mass spectral result of formula N-a.

(4) After sampling at 1.5 hours, the remaining reaction mixture continued to react while keeping the temperature at 60° C., the reaction was sampled at 2 hour (i.e., when continued to react for 0.5 hours) (HPLC analysis results are shown in FIG. 12 and Table 1).

TABLE 1

| | HPLC Analysis Results (%) | | | | | | | | | | |
|---|---|---|---|---|---|---|---|---|---|---|---|
| Comparative Example | Formula N-a | N-1a | RS-2 | RS-3 | Impurity e-a | Impurity f | Impurity g | Impurity h | Impurity i-a | Impurity l | Impurity k |
| 2.1(1) | 5.08 | 0.72 | 3.57 | N.D. | 0.17 | 1.14 | 0.20 | 0.19 | 33.51 | 43.32 | 0.25 |
| 2.2(1) | 63.08 | 33.14 | 0.39 | N.D. | 0.13 | 0.22 | 0.20 | 0.10 | 0.70 | 0.97 | 0.10 |
| 2.2(2) | 82.30 | 4.35 | 0.78 | N.D. | 0.16 | 0.20 | 0.09 | 0.10 | 4.26 | 6.28 | 0.12 |
| 2.2(3) | 79.00 | 2.99 | 1.34 | N.D. | 0.06 | 0.32 | 0.12 | 0.10 | 6.06 | 8.63 | 0.13 |
| 2.2(4) | 76.13 | 1.86 | 1.76 | N.D. | 0.07 | 0.33 | 0.13 | 0.08 | 7.03 | 9.64 | 0.13 |

After calculation, the yield of comparative example 2.1 is about 5%, and the maximum yield of comparative example 2.2 is about 82%.

Note: RS-3 is an urea condensation by-product. The high content of impurities i and 1 in alkaline degradation is due to the use of strong alkaline sodium alcohol in the ring-closing reaction.

HPLC Detecting Conditions:

Instrument: Agilent 1260 series HPLC.

Chromatographic Column: Waters XSelect CSH C18, 4.6 mm×250 mm, 5 μm Column Temperature: 10° C.

Sample Room Temperature: 5° C.

Mobile phase A: phosphate buffer with pH=2

Mobile phase B: chromatographic pure acetonitrile

| Time (min) | % Mobile Phase A | % Mobile Phase B |
|---|---|---|
| 0 | 78 | 22 |
| 20 | 76 | 24 |

-continued

| Time (min) | % Mobile Phase A | % Mobile Phase B |
|---|---|---|
| 49 | 58 | 42 |
| 55 | 30 | 70 |
| 58.5 | 30 | 70 |
| 58.6 | 78 | 22 |
| 68 | 78 | 22 |

Flow rate: 1.0 ml/min

Measurement time: 68 minutes

Detection wavelength: 230 nanometers

Example 10: Preparation of Compound of Formula N-b

Step a: Preparation of the Compound of Formula N-1b

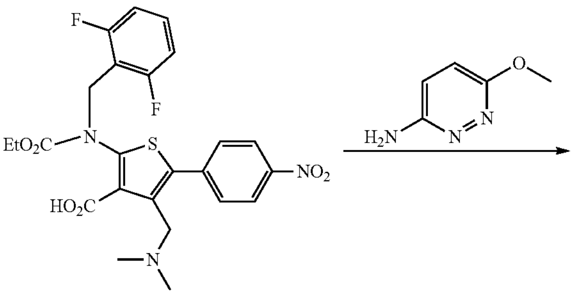

N-2b

-continued

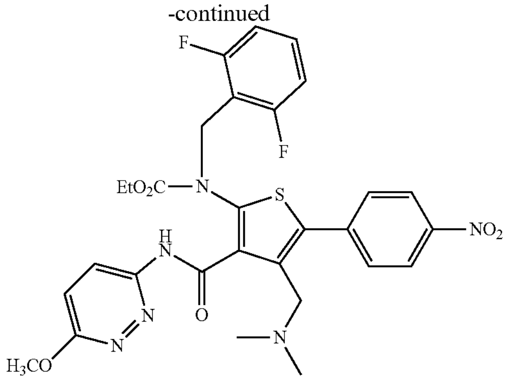

N-1b

The compound of formula N-2b (20 g, 38.5 mmol) was added to 100 ml DCM and the mixture was cooled to 0 to 10° C. Triethylamine (5.84 g, 57.7 mmol) was added, and benzenesulfonyl chloride (11.1 g, 57.7 mmol) was added dropwise. 6-methoxy-3-amidopyridaazine (7.2 g, 57.7 mmol) was added after dripping, and the mixture was reacted while keeping the temperature for 10 hours.

150 ml of saturated sodium bicarbonate solution at 0-10° C. was added dropwise, the mixture was separated, washed with 50 ml of water. The solvent was concentrated and replaced with 100 ml of ethyl acetate. The product was precipitated, and the mixture was filtered and dried to obtain 23.2 g of yellow solid N-1b, with a molar yield of 96.0%, $^1$H-NMR ($CDCl_3$) δ: 1.10~1.40 (3H, m), 2.20 (6H, s), 3.51 (2H, s), 4.10 (3H, s), 4.20~4.35 (2H, m), 5.06 (2H, s), 6.70~6.80 (2H, m), 6.99 (1H, d, J=9.5 Hz), 7.10~7.20 (1H, m), 7.45~7.55 (2H, m), 8.25~ 8.35 (2H, m), 8.54 (1H, d, J=9.5 Hz).

Step b: Preparation of Compound of Formula N-b

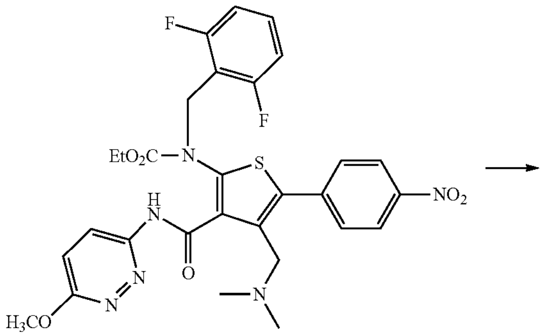

N-1b

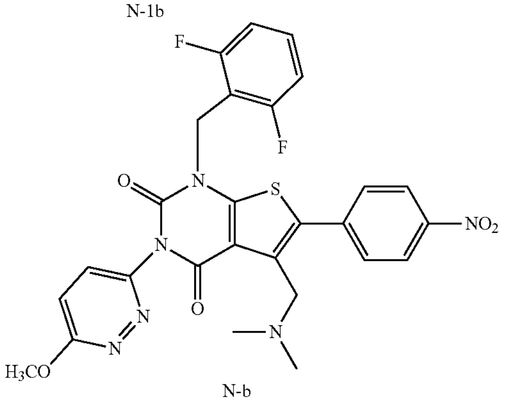

N-b

The compound of formula N-1b (20 g, 31.9 mmol) and potassium carbonate (4.4 g, 31.9 mmol) was added to 50 ml of DMF and the mixture was warmed to 40 to 50° C. and continued to stir for 6 hours. The mixture was cooled to 0 to 10° C., and 100 ml of water was added dropwise. The mixture was filtrated and dried to obtain 17.9 g of white solid, with a yield of 97.0% and a purity of 98.6%.

The crude product was added to 38 ml of DMSO, and heated to 40° C. to dissolve. The temperature was controlled at 35 to 45° C., 100 ml ethanol was added, and the mixture was kept at 35 to 45° C. for 2 hours. The mixture was cooled to 0 to 5° C., and stirred for 2 hours. After filtration and drying, 17.0 g of compound of formula N-b was obtained with a purity of 99.60% and a yield of 97.0%, 1H-NMR ($CDCl_3$) δ: 2.20 (6H, s), 3.72 (2H, s), 4.19 (3H, s), 5.38 (2H, brs), 6.95 (2H, t, J=8.2 Hz), 7.14 (1H, d, J=9.0 Hz), 7.20~7.35 (1H, m), 7.42 (1H, d, J=9.0 Hz), 7.89 (2H, d, J=8.8 Hz), 8.28 (2H, d, J=8.8 Hz).

Example 11 The compound of formula N-1b (2.0 g, 3.19 mmol) obtained in step a of Example 10 and potassium carbonate (0.52 g, 1.59 mmol) was added to 5 ml of DMSO. The mixture was warmed to 40 to 50° C. and continued to stir for 6 hours. The mixture was cooled to 0 to 10° C., and 10 ml of water was added dropwise. The mixture was filtrated and dried to obtain 1.70 g of white solid, with a yield of 91.9% and a purity of 98.5%.

After drying, the crude product was added with 3.5 ml of DMSO, and heated to 40° C. to dissolve. The temperature was controlled at 35 to 45° C., 12 ml ethanol was added, and the mixture was kept at 35 to 45° C. for 2 hours. The mixture was cooled to 0 to 5° C., and stirred for 2 hours. After filtration and drying, 1.65 g of the compound of formula N-b was obtained with a purity of 99.68% and a yield 97.0%.

Purity and impurities detected by HPLC were as follows:

| Formula N-b | Impurity N-b1 | Impurity i-b | Impurity N-b3 | Impurity N-b4 | Impurity e-b |
|---|---|---|---|---|---|
| 99.60% | 0.03% | N.D. | N.D. | N.D. | 0.08% |
| 99.68% | 0.02% | N.D. | N.D. | N.D. | 0.05% |

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

The invention claimed is:

1. A method for preparing a compound of formula N, wherein the method comprises the following steps:

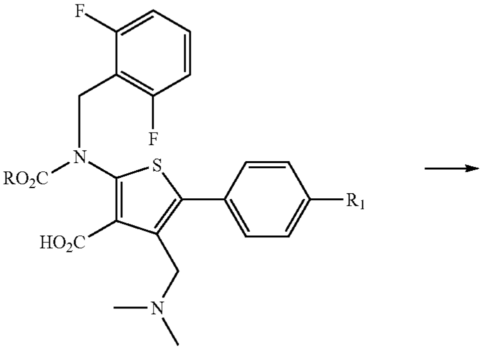

N-2

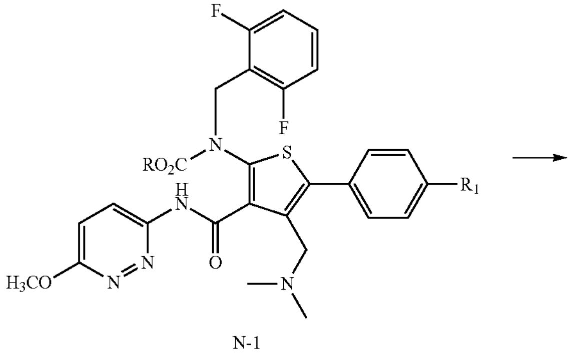

N-1

-continued

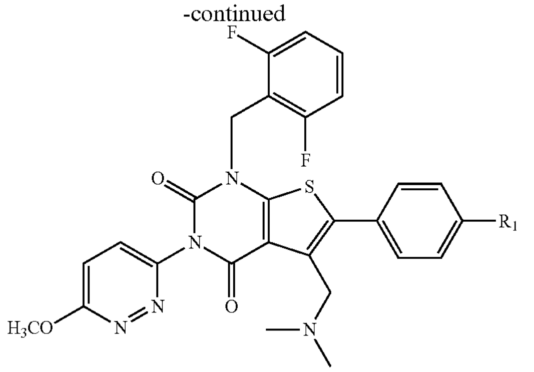

N (a) in inert solvent A, in the presence of an organic base and an acyl chloride, subjecting a compound of formula N-2 and 3-amino-6-methoxypyridazine to a condensation reaction, thereby obtaining a compound of formula N-1; and (b) in inert solvent B, in the presence of a base, subjecting the compound of formula N-1 to a ring-closing reaction, thereby obtaining a compound of formula N;

in each formula, R is $C_{1-6}$ alkyl, and $R_1$ is $—NO_2$ or $—NHCONHOCH_3$.

2. The method according to claim 1, wherein in step (b), the base is an inorganic base.

3. The method according to claim 1, wherein in step (b), the base is selected from the group consisting of carbonate, phosphate, bicarbonate, hydrophosphate, or a combination thereof.

4. The method according to claim 1, wherein in step (b), the base is selected from the group consisting of potassium carbonate, sodium carbonate, caesium carbonate, tripotassium phosphate, or a combination thereof.

5. The method according to claim 1, wherein the method comprises one or more features selected from the group consisting of:

a. the organic base is an organic compound containing 1-3 nitrogens and 3-20 carbons;

b. the acyl chloride is selected from phosphorus oxychloride, thionyl chloride, $C_{1-8}$ alkyl sulfonyl chloride, $C_{4-20}$ aromatic sulfonyl chloride, $C_{1-8}$ alkyl acyl chloride, $C_{4-20}$ aromatic acyl chloride.

6. The method according to claim 1, wherein the organic base is a compound selected from the group consisting of $R_2NH_2$, $(R_2)_2NH$, $(R_2)_3N$, 4 to 7 membered heterocyclic alkyl containing N heteroatom, 5 to 6 membered heteroaryl containing N heteroatom, or a combinations thereof, wherein $R_2$ is $C_{1-6}$ alkyl.

7. The method according to claim 1, wherein the method comprises one or more features selected from the group consisting of:

a. the organic base is selected from the group consisting of triethylamine, pyridine, or a combination thereof;

b. the acyl chloride is selected from benzenesulfonyl chloride, methanesulfonyl chloride, thionyl chloride, or a combination thereof.

8. The method according to claim 1, wherein step (a) comprises one or more features selected from the group consisting of:

a. the molar ratio of the compound of formula N-2 to 3-amino-6-methoxypyridazine is 1:1 to 3;

b. the molar ratio of the compound of formula N-2 to the organic base is 1:1.5 to 5;

c. the molar ratio of the compound of formula N-2 to the acyl chloride is 1:1 to 3.

9. The method according to claim 1, wherein step (a) comprises one or more features selected from the group consisting of:

a. the molar ratio of the compound of formula N-2 to 3-amino-6-methoxypyridazine is 1:1.4 to 1.6;

b. the molar ratio of the compound of formula N-2 to the organic base is 1:1.4 to 2.1;

c. the molar ratio of the compound of formula N-2 to the acyl chloride is 1:1.4 to 1.6.

10. The method according to claim 1, wherein in step (b), the molar ratio of the compound of formula N-1 to the base is 1:0.5 to 3.

11. The method according to claim 1, wherein in step (b), the molar ratio of the compound of formula N-1 to the base is 1:0.5 to 2.0.

12. The method according to claim 1, wherein in step (b), the molar ratio of the compound of formula N-1 to the base is 1:0.7 to 1.1.

13. The method according to claim 1, wherein the compound of formula N is a compound of formula N-a, (N-a)

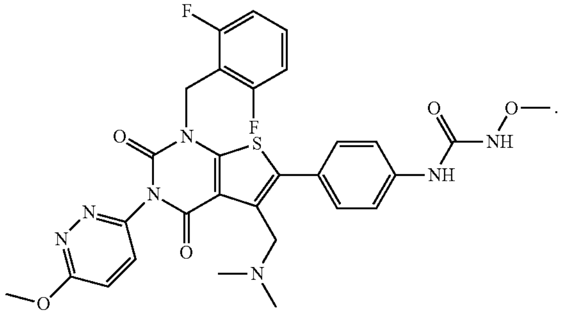

14. An API product comprising the compound of formula N or a salt thereof,

N

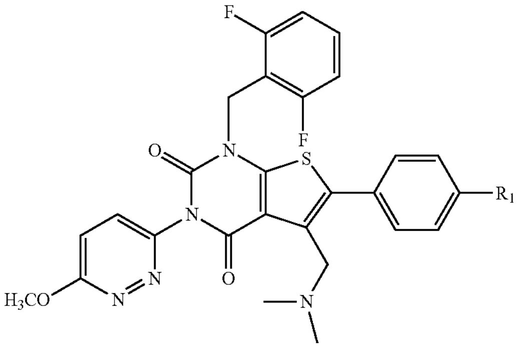

wherein the purity of the compound of formula N is ≥99.5%; and the content of both impurity i and impurity f in the API product are ≤0.15; wherein the impurity i is a compound of formula i, (i)

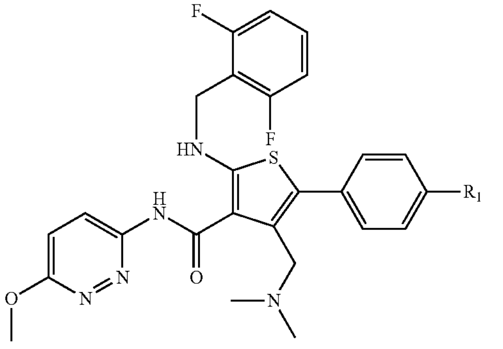

and impurity f is a compound of formula f (f)

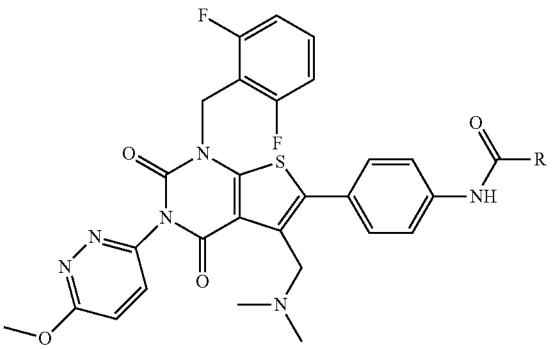

wherein R is $NH_2$ or $C_{1-6}$ alkoxy wherein the compound of formula N or a salt thereof is prepared by a method comprising the following steps:

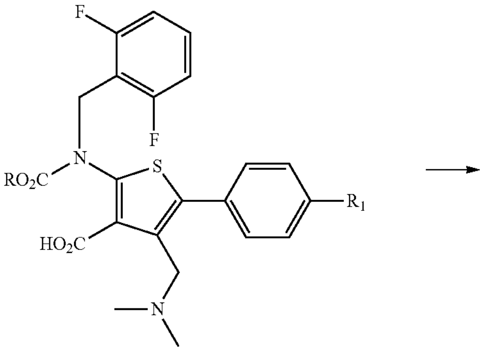

N-2

-continued

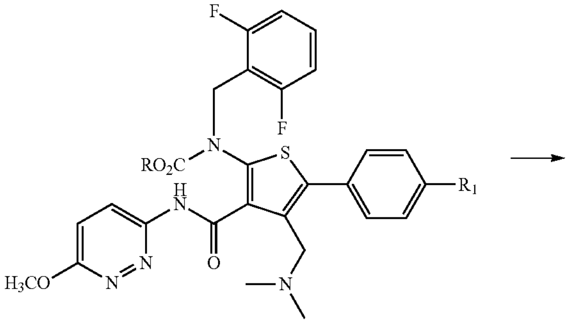

N-1

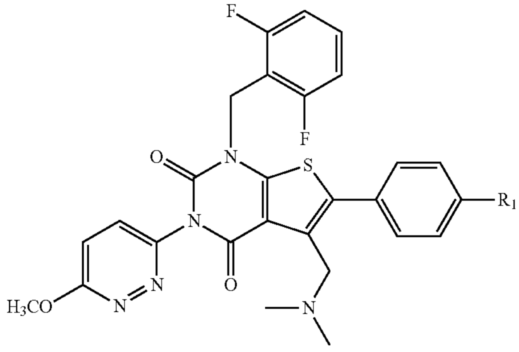

N (a) in inert solvent A, in the presence of an organic base and an acyl chloride, subjecting a compound of formula N-2 and 3-amino-6-methoxypyridazine to a condensation reaction, thereby obtaining a compound of formula N-1; and (b) in inert solvent B, in the presence of a base, subjecting the compound of formula N-1 to a ring-closing reaction, thereby obtaining a compound of formula N; in each formula, R is Ci-6 alkyl, and Ri is —N02 or —$NHCONHOCH_3$.

15. The API product of claim 14, wherein the purity of the compound of formula N is ≥99.6%, and/or the content of both impurity i and impurity f in the API product is ≤0.10%.

* * * * *